(12) United States Patent
Shi et al.

(10) Patent No.: US 8,313,749 B2
(45) Date of Patent: Nov. 20, 2012

(54) *P. GINGIVALIS* VACCINE

(76) Inventors: Xiaoju Shi, Kent (GB); Michael Anthony Curtis, London (GB)

( * ) Notice: Subject to any disclaimer, the term of this patent is extended or adjusted under 35 U.S.C. 154(b) by 1656 days.

(21) Appl. No.: 11/569,125

(22) PCT Filed: May 19, 2005

(86) PCT No.: PCT/GB2005/001976
§ 371 (c)(1),
(2), (4) Date: Nov. 15, 2006

(87) PCT Pub. No.: WO2005/112992
PCT Pub. Date: Dec. 1, 2005

(65) Prior Publication Data
US 2008/0057006 A1 Mar. 6, 2008

(30) Foreign Application Priority Data
May 19, 2004 (GB) .................................. 0411150.6

(51) Int. Cl.
*A61K 39/02* (2006.01)
*C07K 14/195* (2006.01)
*C07H 21/04* (2006.01)

(52) U.S. Cl. ................. 424/190.1; 536/23.7; 536/24.32; 530/350; 424/50

(58) Field of Classification Search ........................ None
See application file for complete search history.

(56) References Cited

OTHER PUBLICATIONS

Crystal RG. Science 270:404-410.1995.*
Verma and Somia (Verma IM and Somia N. Nature 389: 239-242. 1997.*
Anderson WF. Nature 392 (Supp):25-30, 1998.*
Kmiec EB. American Scientist 87:240-247, 1999.*
Romano et al. Stem Cells 2000; 18:19-39.*
Boehringer Mannheim Biochemicals (1991 Catalog p. 557) & Stratagene (1991 Product Catalog, p. 66).*

* cited by examiner

*Primary Examiner* — Padma Baskar

(57) ABSTRACT

A vaccine composition is provided which comprises a rag nucleic acid sequence for the prevention and/or treatment of infection by *P. gingivalis*. Uses of such nucleic acid sequences, proteins coded for by such sequences and antibodies raised against such proteins in medicine are also provided. Kits for the detection of *P. gingivalis* in a sample are also provided.

3 Claims, 34 Drawing Sheets

```
<QML>   6173bp DNA
tcgcgcaacc acaatgaatc cttattatgc caatccttat attctccatc attgatggcc        60
actcgcagtt ttttcgcaga gaaatcagtc acgagcttca tcattacgga atccaaaact       120
gtgccataag gcatatattt cttattaata attgtccctt ttgcatgatc gatagaaaaa       180
aatactttt  ccaaatccgg atttttctta ctggaaaggt agaaacggtg gatctgcaga       240
tcaaccacat tcacgtcttc gagatctaac ttggactctt tacaagagac cacagctatt       300
cctgagcaaa aagagaagaa agtccaaagg agatatcgga tgaaatgttt cttgcacata       360
cctatgataa tttagtgtac aaagataaga catctgctga cttatactac acttttcat        420
ccatcaaacc atggaggccg tatcaaatcc gggatatatt cgagatgtag tagtgcctga       480
tgatttccat cggcctgttt tcaatttata gtgtcatttc agcgtcagat agaaaaaagg       540
ggccatccgt tggacagccc ctttatttgt ttattgacta aaagtcagca gaaattacca       600
gttcttgatc aaatgaggat taacctgacg atctcggtta gggaactccc atgtaaatgc       660
atagtgaccg gccggaacag gttgctccaa tacgatctca cgagcataac cagtaagagc       720
aggttggatt tctgttttgt cgatattcgg aagattccaa cgaatcatat cgcgcaaacg       780
agcgccctca ccgataagct cacgagtacg ttcttcttga atagctttca ttacatcacc       840
ggtgtcaata ttgccaccac gagcagcact gagctttttg aggtatgcaa tcgccgtagc       900
atcgtctcct gtcatgtgag cacactcagc taccatcaga taagcttctg caatactgaa       960
catacgtacc cctattttca gaatggggat atcggctgtt tctctgtagg caggatcttc      1020
aaggaatttg ttcaccaaat atccctttc  actgccgtta ctaactgtct tatcaatata      1080
gactgacttg cgataatctg catcttcgta caaatcgact acccactgca agggaacgat      1140
aaacggcgca tatttaatct tcttattcac cacagatgcg ccattaagag aggttgcacc      1200
aacagcaccg gtcgtaggag atgcaaaagc acggaatacg atctcgggat tgttagcatc      1260
tgaacgatag attttagcaa aatcctctgc attgttagcg ttgatcaaag gatacttctc      1320
cacaatctgc ttagcatctg caagtgcatc ggcatagtta cccatagaaa ggtgtacacg      1380
tgctcgcaaa gcatgagcgt agtcacgtcc ggcatatgtg atgccgtcag ggttcttctc      1440
aggcaatacc gtaatagcag cctccaaagc cgagaggatg tgatcataac actccttctg      1500
agtagcacgg gggccgatat aagcgggatt gaattccttg atcaaaacaa tgccaaggtt      1560
ttgaggactt tgattggatg cggcatcata tttatatgca aaacgatcca tcaaacgcca      1620
attcgccaaa gcttgtacaa cacgtacctc tgcagatat  ctcttagcac gttccacttc      1680
ttcggaggaa atgaaaatgc tcatatcagt attattggca agagcttttt ccatatcttc      1740
gatataggag tttgcctgct gaatcagacg gctatactcg aagtaataac cggcaatacc      1800
atatacttga tcctcatcag cacgaccatg agtttccatg cttcctaact gccaagctac      1860
gaatggatag tactggttgc catcgttctt ggtagtagtg tacatatccg actgaacctc      1920
gtcataaaca tggaaagcta attgctccga ttcacgaagc agagaataca agccatctct      1980
gctctgacga gcctgagcta ttgttttgaa gggctctttc ttggccttat cttccggatc      2040
tctattcaga tcgcaggaaa cgagactcac agcaaaaaga gctgccgcag cccaatataa      2100
```

FIG. 1A

```
tatcttttc  atattctttc  ttctaaattt  ctagttaaaa  cgacagttgg  atacctccca   2160
tgaattgttt  cgtattgggg  aactggttta  gagcgacatt  gcctccagcc  tcagggtcaa   2220
agcctttgta  cttagtcact  gtgaagaggt  tacgagccat  taggtaaaca  cgcgcacctg   2280
aaagaacttt  ctgacctgca  aacaagctat  taggcaatgc  ataggaaagt  ttgaggttct   2340
tcaaacgcag  aaaagaagcg  ttttcaagca  aatgggtatc  gaactgagga  gtttgaccca   2400
aacgaggcac  atccgtatct  ttatttgtct  cagtccaagc  atccaaaagg  attttgctct   2460
tattagtttt  tactccggaa  ggtgcaccat  tttcaataaa  ataacggtcg  ttattaatca   2520
tccacttacc  tatgatatat  gcgaaatcag  catcaagtgc  cagcccttc   caagaggcac   2580
caagagagaa  acctccggtg  atatcggggg  taaccgattt  gcctacgttc  acctccagtt   2640
cagtagagta  tttgttcgtg  gtaactctgt  tgccatcagc  atcatacttt  ccgggaacat   2700
accacaacat  atctcctgtc  tcatgatcaa  tacctgcata  ttcggccatg  tagaaagagt   2760
tgggtttacc  cacctgccaa  attgtacctg  tattcggtaa  tacatattct  tcaagaccgt   2820
ggaatagctc  cgtaatcttt  tgcttgttga  aattgaagtt  tgccgaagca  tatacattcc   2880
aatctttggt  ttgatagatt  gtaccatcaa  gcttaatatc  tataccggta  tttctcattg   2940
agcccacatt  ctgatactga  gagaagaaac  cactcgcata  aggcatgggg  acgtcgatta   3000
gcatatcttt  cgtagagcga  acatagaagt  ctacctctgc  tctaagtcta  ttatcgaaca   3060
tcgcagaagc  aactccgaca  ttgaactgag  cctgtgtttc  ccaagacaaa  tcggggttac   3120
cggccgtatt  gataatgagg  cccaaatcgt  cgtcggtata  gttgtacgca  gaaacaaaag   3180
cctgatggcc  atagttaccg  atctcagagt  taccggtcgt  accatagctc  actttgagcc   3240
gaagatcatt  gagccaattg  cttttcctgaa  tgaacttatt  atagatgtcg  aacatagcac   3300
ctgccgagta  gaacatcgca  ctacgattgt  tctcaccgaa  gcgagaagag  cggtcattac   3360
gcagagatag  gtctacatac  atccacttgt  cgaaaccata  gctaccacga  ccaaagaaag   3420
agagataagc  ataagcttcc  ttctgctgag  caggaagaat  caaattatca  cccttctttc   3480
cctgagaaag  caacatcata  tcggcatttt  cataaccttt  ggcctgagca  cggaaccatt   3540
ccaactctgc  atcgataaac  tcatgaccca  gcaagagggt  aacatcatgc  ttgtcttcta   3600
cattaaactt  gtattcggca  gtattggtag  aagtgtaaac  acgtcttccg  tcaaaacgct   3660
ctgtacgtga  accaagatgg  gttccggcca  aggggttgtt  tggtaaactt  ttgcccgtat   3720
aacgtgtgtc  tttaatatca  gcacctacct  gagcctttaa  tgtcaggccc  ttgataggat   3780
tcaattggag  atagcctgtt  gtaatcgctt  ggaagaagt   atattccgca  ggataccatt   3840
tataatcacg  ctcagggctc  tggaacacac  gtgtagcacc  cgaaatgaaa  taagcctcag   3900
ccaattcatc  gctatgtttc  ccattagaga  tcaagaatgg  attgaaaaac  ttcggcatag   3960
acaacgctcc  aaacgtaccg  gtattatagt  aatttgtacc  actgaaagaa  gacgttttt   4020
gattagccat  tgaacctgaa  agattcatcc  caatcttcat  ccaatcattg  attcggctgt   4080
caagattgaa  tcgagtagtg  tagcgtttga  agagagaagg  ctcgcgagag  atacccctct   4140
gatcaaaata  gcctagtgac  acataataag  aagtaccggt  agaaccgccc  gaaaaagttg   4200
catccacttg  tgtggtagga  gctgttggac  ggataaagta  tttcagccag  tctgcatcct   4260
```

FIG. 1B

```
cagagaagtc aaccggacga agtgtattat tcttcagtcc atcggcaagc aagggatact   4320
gattgaacaa atcttcggcc tcttggatat acttcttcat cacggcgtcc acctgatcag   4380
gatcgttcgg attattgaga gcattaccat ggagaccaga gagcatctga tacttaagat   4440
gttccattcc cgtcatcata ttctctgtgg gtttcttgct aataatagaa gaaactccat   4500
agctggcact gaacgttaca cgaccggtct cactcatctt acctcttttc gtttggatca   4560
gaaccacacc gttagcagca cgtgcgccat agatggaggt agcagaagca tccttgagta   4620
cggtgactga ttcaaagtca ttcgggttca tcgcagccac aacagccaat gtagtcgcca   4680
ctccatccac gatgtacaga ggagctgtac cagcacccaa agaaccgaca ccgtgaatag   4740
tcacattggc tacctggttc gggtcaccgg atgtagtcat aacctgcata ccggctacct   4800
gaccttggag ggcatccatg atgttggcaa cgggcttttc cgcgagcttt tcgctggaca   4860
ctttggccac agaaccggaa acggtgctga gtttctgtcc cgtaccataa cccaatacaa   4920
ctacctgctc cagaaccttg agtccggat ccagtacgat cttcatcaca ttagcgatgg   4980
cgacctcttt ggtagtcata ccggaatatg acactctcaa cattttggca ttggcaggca   5040
cgctaagcgt gaagttgcca tccaagtcgg ttgcagcacc gatagtggtg tttccgacaa   5100
ccacgacatt cgcgccgatc agggctcat tatcctcgga ggagataact gtaccttca    5160
cggttctatt ctggccata gcccacccaa tgctcgtcag caagcaaagg aagaatagcg   5220
tcattctttt catagacttt tcttttgcgt taaacttaaa attattactg ttatgttgtt   5280
ttctttcttt ctccggtttt accctaacca agggaagtct caaaaagccg ctaccggcct   5340
tagacacaag tcacgaaact tccacaactg ccctatgata cggacagcca caaactaaa   5400
taaaaaatg caaccagact aatcctatta tccttttttt catctaagca atttgctcac   5460
catacgattt gtcaaatcca ctttgcaaaa ggagcagcaa taaaccgatg taaatttgaa   5520
ttttggaaga cagagtgttt cttttgaccg atcgaacact ctcaatattg agacaccttg   5580
attccacatc aatgctattc tcctgatgct tgtgaactac tgtctcggaa tacgagccta   5640
aaacacttcg atttcagttc gattttatgg aataaagtgg cgcaggattt ttttcgtttt   5700
ggctcgatat ttttcactt ctcgcgccaa aatgaaaaag tttacgcgcc acgttttag    5760
aaaccacaaa tgcagaaatt tctgcaacgt gacatgtgat gtaaggtcct aaagaggaag   5820
attgtaatgc cggcagactc gctataaatc gcaggtatta atccccggca atgagtaatg   5880
ttcttttctc ctcgggaact atgattcgga gggatcccca taagagcaaa agcgattcgt   5940
caattttcct taacccaaac gtctcattcg gggaacggat tcgggaaccc aaaaaagaaa   6000
accatggcat ctcgactcac ttcctgccac aagagaaaaa tcaaggggga gccgcaaatg   6060
aaatactcgc gactccccct tacttggttt gagagaaata tcagatgctg aaagctactg   6120
tatggaagaa caacagtcct atagtcgcaa tagcatcatc ttcttcacat tat           6173
```

FIG. 1C

<Thai rag> 7361 bp DNA

```
caaagtcctg ccacgagtag caatgtaagg aaagttgtag tcaactaata atgtgaagaa    60
gatgatgcta ttgcgactat aggactgttg ttcttccata cagtagcttt cagcatctga   120
tatttctctc aaaccaagta aggggagtc gcgagtattt catttgcggc tccccttga    180
tttttctctt gtggcaggaa gtgagtcgag atgccatggt tttctttttt gggttcccga   240
atccgttccc cgaatgagac gtttgggttg aggaaaattg acgaattgct tttgctctta   300
tggggatccc tccgaatcat agttcccgag gagaaaagaa cattactcat tgccggggat   360
taatacctgc gatttatagc gagtctgccg gcattacaat cttcctcttt aggaccttac   420
atcacacgtc agttcgacgt aagaaaaagc caatggattt gttttctgat tagtggtaaa   480
cgcccaaaga acgtgggcaa tatgcttgaa aaagtagcga attatttgta tcttagcagt   540
tgataatcaa taagatacga acaaacaaaa cgctactta tgaagacaaa tatagttgat    600
gttttttgca tcatagatga tttctccaag ctttttgatg aaacaatcaa gaaaaagacc   660
ctcgaagagg cagacaaaaa aggcaggaat agaaagttta agatgtcgga cagtgaggtc   720
atgaccatcc tgatcctgtt tcatctgtca agataccgag atttgaaagc ttttatctt   780
caatacatct cccattcttg tcgatccgag tttccacatc ttgtctctta taatcgcttt   840
gtggagctgc aaagcagggt aggtttcaag ctgatagcat ttctcaatat gtgttgtttg   900
ggtcaatgta caggcatctc tttcatcgat tccaccccat tgaaggcttg tcatatcaaa   960
cgagctcatg ggcataggac aatgagggga tgggctcaaa aaggcaaaag caccatgggt  1020
tggttttatg gattcaagct acatattgtt atcaacgaca ggggtgaaat catcaactat  1080
caaatcacac cgggcaattg tgatgacaga gaacctctga aagacggaac attcaccaag  1140
aatcttttg gcaaactcat tgccgataga ggctacattt cccaaaacct ttttgaccgg  1200
ctctttgtcg atgacatcca catgataacc aaaatcaaaa agaacatgaa gaactccctg  1260
atgcatctat atgacaaagt tttattgaga aagagagccc tgatcgaaac agtcaatgat  1320
atgctcaaaa atgtctgtca gatagagcac acgagacatc gcagtgtcaa caattttgtc  1380
accaacctga tctccggtat catcgcttac aacatcctgc taaaaagcc tgaactcaat  1440
attgaaatca tcagaaaccc taactttcct atttccgctt agatcgaact gacgttacat  1500
cacatgtcac gttgcagaaa tttctgcatt tgtggtttct aaaaacgtgg cgcgtaaact  1560
ttttcatttt ggcgcgagaa gtgaaaaaat atcgagccaa aacgaaaaaa atcctgcgcc  1620
actttattcc ataaaatcga actgaaatcg aagtgtttta ggctcgtatt ccgagacagt  1680
agttcacaag catcaggaga atagcattga tgtggaatca aggtgtctca atattgagag  1740
tgttcgatcg gtcaaaagaa acactctgtc ttccaaaatt caaatttaca tcggtttatt  1800
gctgctcctt ttgcaaagtg gatttgacaa atcgtatggt gagcaaattg cttagatgaa  1860
aaaaggata ataggattag tctggttgca ttttttatt tagttttgtg gctgtccgta   1920
tcatagggca gttgtggaag tttcgtgact tgtgtctaag gccggtagcg gcttttgag   1980
acttcccttg gttagggtaa aaccggagaa gaaagaaaa caacataaca gtaataattt  2040
taagtttaac gcaaaagaaa agtctatgaa aagaatgacg ctattcttcc tttgcttgct  2100
```

FIG. 2A

```
gacgagcatt gggtgggcta tggcccagaa tagaaccgtg aagggtacag ttatctcctc    2160
cgaggataat gagcccctga tcggcgcgaa tgtcgtggtt gtcggaaaca ccactatcgg    2220
tgctgcaacc gacttggatg gcaacttcac gcttagcgtg cctgccaatg ccaaaatgtt    2280
gagagtgtca tattccggta tgactaccaa agaggtcgcc atcgctaatg tgatgaagat    2340
cgtactggat ccggactcta aggttctgga gcaggtagtt gtattgggtt atggtacggg    2400
acagaaactc agcaccgttt ccggttctgt ggccaaagtg tccagcgaaa agctcgcgga    2460
aaagcctgtt gccaacatca tggatgccct ccaaggtcag gtagccggta tgcaggttat    2520
taccggttcc ggtgaccota ctgccgtcgc ttctgtgaag atccacggtt cagggtcttt    2580
gacttcaagt tcagcccctc tctacatcgt ggatggtgtg ccgactgatt tgggtgtagt    2640
tgccggtatg aaccctaatg acttcgaatc gtttacgatt cttaagacg cttcttctac     2700
ttctatctat ggtgcgcgtg cagccaatgg cgttattgtc attacgacca aacgcggaaa    2760
gatgggagag cgtggccgta ttacgttcaa cgccagctat ggagtgtctt ctattattaa    2820
taaaaaaccc ttcaagagca tgatgacggg agatgaattc gcccgttggc agtatggtgt    2880
cggctatgct gcagcagatc aatacagtac tttcgaggca tggaaagacc acattaaaga    2940
ggatgctaag caagcattga taaactactc accttatctt gaggatcaaa tcaagaaagg    3000
tatacttgat ccgataaact ttgataaaga tacggattgg ctgggatacc atttccgcac    3060
tgctcctacc actcaaggag atgtttctat ccagggaggt tcgcaaggca cttcttactt    3120
cttatctttg ggatattttg accaagaggg tatctctcgc tcggaatctc ttttgaagcg    3180
ttatacaggt cgtcttaact tggaaagccg tgtgaacgat tggttgaagg ttggagccaa    3240
tatgtcggca gctcttgcca aaagacgtgc ctctggtttt gcttcttctg cgtatatctc    3300
agaaggatca tttgctgctt tggttgctgc tccttatctg aatccctata caacatcagg    3360
cgattttgct gaagcgtatt acatggattt tcaagacaaa gtaatattcg gaattccgca    3420
ccgtgacagc tatcgtcctt ataatcgtga agcttatcaa gcaacgatga gtggatatgc    3480
acaactcaca ccgataaagg ggctgacgct caaggcacaa gccggcttcg acttttgca    3540
agaacgcact tcttctaaac tgcttcccaa taaccccttg gcattggacc cgttgggtac    3600
aagtcgggag cgtttttatc actatttgac caaaactttt accaacacgg cagagtataa    3660
gttctcggta gaagataagc atgacgtgac tcttttggca ggccatgagt ttatcgatta    3720
cgaatatgat atgtttggag ccttaggaaa gggttacgaa atccgaaat tcatgatgct     3780
tagccaagca aaaggtgata cttatttgac tttgcccgaa caggcaaaag ctgaatatgc    3840
ctatctctct ttcttcggcc gtggtagcta tggttttgac aagtggcttt atgtagacct    3900
ctctgttcgt aatgatagat cttctcgctt tggtgccaat aaacgtagtg cgatgtttgg    3960
atccggtggc gttatgatga tgttttcaa caaattcatt aaagaaagca cgtggctcag    4020
tgatctgcgc tttaagatga gctatggtac taccggtaac tccgaaatga gaaattacac    4080
aactggaaac cctgaatatt atgctcattt ggctttggtt ggtagcaatc catatacgga    4140
caacgctttg ggcctttcgg tggctacacc gggtaaccct aatctttcat gggaacaaca    4200
atctcagttc aatgtaggtg ttgcttcttc attctttgat ggtcgactca acgctgaatt    4260
```

FIG. 2B

```
ggatttctat gttcgtgcta cagacgatat gcttatcgag gtgcctctgc cttatttgag    4320
cggattcacg gctcagttgc agaatgtggg tgctatgaag aataccggtt tcgatattac    4380
tgttagtggg gatattgttc gaagcaagga cttcaaggtg tacggatcag ctacatttaa    4440
ctataaccgt gaagaaatta cacgtctatt ctccggtctc aaggagtacg ttcgtgatgg    4500
atatagctat tcatggattg ttggcaagcc tacagtattc tattgtgctg aatatgctgg    4560
cgtttataaa ggccaagccg gccccaatta tgtggatgct gaaggcaagc cctttaaggg    4620
tggagaccaa atgtggtatg tccccggaga atacaatgaa gatgggagtc gcaagcttac    4680
caataaatat tcttcttcat tggagcatgc tctgacagat aaggctctca ctcctcccgt    4740
tacaggagga ttttccttag gtgcttcatg gaaagacctt tctttggatg cagatttctc    4800
ttatattctg ggtaagtgga tgattaataa tgaccggtat tttacagaaa atacttcccc    4860
cggttttaac tttacaaata aagacaagat gatactgaat gcatggacgc agcagaattc    4920
tgattcggat gtgccccgta tcggtcagtc gatgcatttt gactctcgct tgttagaaaa    4980
cgcttctttc ttgcgtatga agaatctgaa attgacttac aacctgcccc aaaatctctt    5040
cgccggtcag aatgtcctct cgggagcgcg tgtctacttg atggctcgta acttgtttac    5100
aattacaaag ttcaaaggtt ttgaccctga agcaggagca aatctatcta tgaaccagta    5160
tcctaatact aaacagtacg tggctggtat tcagttgtct ttctaatgca attcactttt    5220
aagaaaaca atgaaaatga aaaaaataat taattatgct gtggccggat tgctactcgt    5280
ttcaagctttgccgcttgtg acttggatcg cactcctcac aattctgatg tccaaaagcc    5340
ttatgaagat atggccacca cagttcagta tagagatgga ttgtattctg ttcttcgtgg    5400
tgcagagaat gccggacggt atactttgtc agaatatatg tccgatatgt attgtgtaat    5460
gcaaggagat ggtggccatg ctacgcctta tgttacatgg acgattcctc gcattgagat    5520
tgctgaccac gcatcgaatt attactttgg ttttaatcgg ttaattcagc aagccaatgc    5580
ttttgtcgga aatgttaagc tggcaatcgc aaatggggtt tataagacag aagttgataa    5640
aaccaatgct caaatttatt tggctgaggc caagactttg caggctttag ctttgttccg    5700
tcttatggag cgctttgcct atccctatga tccaaacgaa accacttctc cgaaaaactt    5760
gggggtggtt ttgataaagg aatatgatcc ttgggctgtg ggtgcacgag ctacgcagac    5820
ggaaacgtat agctatatta tgagccttct tgatgaggcc atctctgttt tgcctgaaac    5880
gaatgcgaac aatatgtatg tgagtcggga ttatgcttta ggcttgcgtg ctcgcgtaca    5940
catggcgatg gataactatc tgaagccgc caatgatatc agagcttttt ataaaaagta    6000
caatctgatt tctgctgcta attccgatga atttgaggag gcttatagaa agatgagctc    6060
caatcctgag cttattttcc gcggatatgc ttccgttact aacggatacc ttgtgtatca    6120
ggatttgatg ggagcaacag cttctggaac taatgtgaag tacaaccctc gtgttacccc    6180
tctgcaatgg gttttgcgacc tttatgatgc ggctgattat cgtaagaaag tgtacattgt    6240
agacaaggtg aacggtgacg gtggcaaagg ttatgtcgta aataagttcc ttggagaccc    6300
tgaacttcgt gaagaccccta agaaggaaaa tttcaaaacc ggttgtcgtt tcttctctct    6360
cgcagaagcc tatcttatct tggcagaagc agatattatg actggtaata cagccgaggc    6420
```

FIG. 2C

```
tatggaagtt ctgaaagagc tgagtaagtc tcgtggagca gaggtttccg gtgcagatta    6480
tatgcaaatc ctcaaggatg agcgtacacg agaaatgatc ggtgaaggtt ctcgtctcaa    6540
tgacatgatt cgctggaata tggatttggt ggtatctccc gttcaggctg ttcttcataa    6600
aatagctgtc ccgactatcc ttcagactga tgacccgaca cgtgttcctg ccggcttcta    6660
tgctttcacg tgggaaattc ccaatcgtga tcttgtagtt attcccgagc tggttcgcaa    6720
ctggccaaaa cagtaagtag cattcttttt tttagcaact tgctatccta ttgcagggag    6780
caccggtttc cggtgctccc tgttcgcttt attgcatgtg acgatttata atgcagaagt    6840
cttcttcaag ctagtgagac aattttgttt aatacgagaa tccgggaaac gagtgttgtc    6900
ctatagcata agtcggcaga tgtcttatct ttgtacacta aatatcagta ggtatgtgta    6960
agaaacattt catccaatac ttcttttgga ctatcattgt ctttttgtg ggtggggcta    7020
ttcactcttg taaggagtct aagatagatc ttgaagaagt tagcatagtc gatctgcaga    7080
tccaccgatt ctacctttcc agtaagaaaa atccggattt ggaaaaagta ttttctcta    7140
tcgatcatgc aaaagggaca attattaata agaaatatat gccttatggc acagttttgg    7200
attccgtaat gatgaagctc gtgactgatt tctccgcgaa aaaactgcga gtggccatca    7260
atgatggaga atataaggat tggcataata aggattcgtt gtggttgcgc gattgtcata    7320
ccttgcattt aatggttttc gacgaaagtg gcgagaaaac g                        7361
```

FIG. 2D

<W50 rag>   8346 bp DNA

| | | | | | |
|---|---|---|---|---|---|
| caaagtcctg | ccacgagtag | caatgtaagg | aaagttgtag | tcaactaata | atgtgaagaa    60 |
| gatgatgcta | ttgcgactat | aggactgttg | ttcttccata | cagtagcttt | cagtatctga   120 |
| tatttctctc | aaaccaagta | aggggagtc | gcgagtattt | catttgcggc | tccccttga   180 |
| tttttctctt | gtggcaggaa | gtgagtcgag | atgccatggt | tttcttttt | tgatccccga   240 |
| atccgttccc | cgaatgagat | gtttgggttg | aggaaattg | acgaatcgtt | tttgctctta   300 |
| tgagacccttt | gcacggcgat | tggcgtatat | tttgtttgtt | aattcattgt | ataataggga   360 |
| gttatttgt | atatttgagt | attaaaaaca | gcataatatt | cctcccatgg | cataccaatc   420 |
| caagaatacc | gatgagcatg | taacatttgc | agacgcactc | ctttcaaagc | gttatcgcaa   480 |
| agcacaaaac | gacttcctca | atcaggttga | caggcttatc | gattggcgtc | cgatcaggac   540 |
| gctgatcaac | aagaaataca | ccaagcgaca | aaatgccatc | ggcgccccgg | cttatgacgt   600 |
| gattctctta | ttcaagatgt | tgcttttgga | gacatggtac | aacctcagtg | attgtgcttt   660 |
| ggaggagcgc | atcaatgatt | caatcacctt | ttcccgattc | ttggggctga | agatggaaga   720 |
| ggtttctccc | gaccacagta | ccatcagtcg | atttcgttcg | gcactgacag | agttgggtct   780 |
| catggacaaa | ctattggcgc | agtttaacaa | acaactttcc | cgccatcaca | tttcggtcag   840 |
| ggaagggtg | cttgtcgatg | caagccttgt | ggagacgccg | cataaaccca | acggaagcat   900 |
| tacgattgaa | gtcgcagacg | acagagaaga | caatcggagc | gaggaggaaa | aagaggcaga   960 |
| ggaggattat | caaaaacagg | ttgtccgtca | gcgtaaaggg | acggatgaag | aagcccgttg  1020 |
| ggtttacaaa | caaaagcgtt | atcactacgg | atacaaaaag | cattgtctga | ccaatgttca  1080 |
| aggcattgtt | caaaaggtga | taacgactgc | agcgaaccgc | agtgacacga | aggagtttat  1140 |
| tgcgctattg | cagggtgcaa | acatatctca | aggctcagcc | gtcttggcgg | acaaaggata  1200 |
| tgcttgcggg | gaaaatcgtt | cctacctgca | aacccatcac | cttcaagacg | gcatcatgca  1260 |
| caaggcacaa | cgcaacaggg | cattgaccga | ggaagagaag | caacgaaaca | aagcaatcag  1320 |
| tcggatacgg | agcaccatcg | aacgcacctt | tggcagtatt | cgccggtggt | ttcatggcgg  1380 |
| acgatgtcga | taccggggac | ttgccaagac | ccatactcaa | aacattcttg | aaagcatcgc  1440 |
| ctttaattta | tacagaaccc | cggggataat | tatgtcctca | tttgtaggat | aaggcataac  1500 |
| cccccttgag | gagctcgtgc | aagcagctcc | tcaagggggg | atttacaact | actttcactc  1560 |
| cttactgcca | cccctttcac | tcgctccttt | tatgccaaga | actcctcttc | cctccacctc  1620 |
| cttattttgc | aaaggtctcc | ttatgggaat | ccctccgaat | catagttccc | gaggagaaaa  1680 |
| gaacattact | cattgccggg | gattaatacc | tgcgatttat | agcgagtctg | ccggcattac  1740 |
| aatcttcctc | tttaggatct | tacatcacat | gtcacgttgc | agaaatttct | gcatttgtgg  1800 |
| tttctaaaaa | cgtggcgcgt | aaacttttc | attttggcgc | gagaagtaaa | aaaatctcga  1860 |
| gccaaaacga | aaaaatcct | gcgccacttt | attccataaa | atcgaaccga | aatcaaagtg  1920 |
| ttttaggctc | gtactccgga | gacagtagtt | cacaagcata | caggagaata | gcattgatgt  1980 |
| ggaatcaagg | tatctcaata | ttgagagcgt | tcgatcggtc | aaaagaaaca | ctctatcttc  2040 |
| caaaattcaa | atttacatcg | gtttattgct | gctccttttg | caaagtggat | ttgacaaatc  2100 |

FIG. 3A

```
gtatggtgag caaattgctt agatgaaaaa aaggataata ggattagtct ggttgcattt    2160
ttttatttag tttFgtggct gtccgtatca tagagcagtt gtggaagttt cgtgacttgt    2220
gtctaaggcc ggtagcggct ttttgagact tcccttgggt tagggtaaaa ccggagaaga    2280
aaagaaaaca acataacagt aataatttta agtttaacgc aaaagaaaag tctatgaaaa    2340
gaatgacgct attcttcctt tgcttgctga cgagcattgg gtgggctatg gcccagaata    2400
gaaccgtgaa gggtacagtt atctcctccg aggataatga gccctgatc ggcgcgaatg    2460
tcgtggttgt cggaaacacc actatcggtg ctgcaaccga cttggatggc aacttcacgc    2520
ttagcgtgcc tgccaatgcc aaaatgttga gagtgtccta ttccggtatg actaccaaag    2580
aggtcgccat cgctaatgtg atgaagatcg tactggatcc ggactctaag gttctggagc    2640
aggtagttgt attgggttac ggtacgggac agaaactcag cactgtttcc ggttctgtgg    2700
ccaaagtgtc cagcgaaaag ctcgcggaaa agcccgttgc caatatcatg gatgccctcc    2760
aaggtcaggt agccggtatg caggttatga ctacatccgg tgaccctact gccgtcgctt    2820
ctgtggagat ccatggtaca gggtcgttgg gggcaagctc tgcaccattg tatatcgtgg    2880
atggtatgca aacttctttg gatgttgtgg ctacgatgaa tccgaatgat tttgaatcta    2940
tgtccgtttt gaaagatgct tctgcaacat ctatttatgg agctcgtgct gcaaacggag    3000
tcgttttcat tcaaacgaag aaaggtaaaa tgagcgagag aggtcgtatt acctttaatg    3060
ccagttacgg gatttctcaa atcctgaata ctaagcccct tgataatatg atgactggag    3120
atgaattgct ggattttcag gtgaaggcag gtttttgggg gaacaatcaa accgttcaga    3180
aggttaaaga tatgatcctt gccggagctg aagatttgta tggcaattat gattctttga    3240
aagatgagta tggtaagaca ttgttcccag tggattttaa tcatgatgca gactggctca    3300
aggctttgtt taaaacagca cccaccagtc aaggtgatat ttctttctcc ggagggtctc    3360
agggaacttc atattatgcc tctataggct acttcgatca ggaaggtatg gctcgtgaac    3420
cggcaaattt taagcgctat agtgccggc tcaacttcga aagtcgtatc aatgaatggc    3480
tgaaagttgg tgcaaatttg tctggtgcga tagcgaatag acgatctgcc gactattttg    3540
gaaagtatta tatggggtca ggtactttcg gtgtgttaac gatgcctcgt tattataacc    3600
cttttgatgt gaatgggat ttagcagatg tctattacat gtatggagct accagaccttt   3660
ctatgacaga accgtacttc gcaaaaatga gaccgttcag ttccgaatca catcaggcca    3720
atgtaaatgg tttcgcccag attactccga tcaaaggcct tactttaaag gcacaggctg    3780
gtgttgatat tactaatact cgcacttctt ctaagagaat gcccaataat ccgtatgatt    3840
ctactcctct tggggaaaga agagaaagag cttatcgaga tgttagcaag tcttttacaa    3900
atacggctga atataagttt tcaattgatg aaaaacatga tcttacagca ttgatggggc    3960
atgaatatat tgaatatgaa ggggatgtta ttggggcatc ttctaaagga tttgaaagtg    4020
ataagttgat gttactgagc cagggaaaaa ccggaaatag tttgtctttg cctgaacaca    4080
gagtcgctga atatgcctat ttgtctttct ttagtcgttt taattacggt tttgacaaat    4140
ggatgtatat agatttctct gttcgtaatg accaatcctc tcgattcgga tccaataata    4200
gaagcgcgtg gttctattct gtcggtggaa tgtttgacat atataataaa ttcattcaag    4260
```

FIG. 3B

```
aaagtaattg gctcagtgat cttcgactga aaatgagtta tggtacaacg ggtaactcgg    4320
agattggtaa ttacaaccac caagcactcg ttactgtgaa caattatact gaagatgcta    4380
tggggcttag catttctaca gcaggcaatc ccgacctctc gtgggaaaag cagtctcagt    4440
tcaacttcgg tttggctgca ggggctttca ataatcgctt atctgcagag gtagatttct    4500
atgtccgcac tacgaatgat atgttgattg atgtcccgat gccttatatc agtggtttct    4560
tctcacagta tcagaatgta ggctctatga aaaatacggg tgtagacctt tctcttaagg    4620
ggacgatcta ccaaaataag gactggaatg tatatgcttc tgcgaatttc aactacaata    4680
gacaggaaat aacaaagctt ttcttcggtc tcaataagta catgttgcct aataccggta    4740
ctatatggga aattgggtac cccaattcgt tctatatggc tgaatatgct ggaatcgaca    4800
aaaaaaccgg taagcagttg tggtatgttc ctggtcaagt cgatgcggat ggtaataaag    4860
ttacaacaag ccagtactca gctgacttgg agacacgaat tgataagtct gttactcctc    4920
ctattacagg tggtttctcc ttaggtgctt cttggaaagg actttcttta gatgctgatt    4980
ttgcctacat cgttggtaaa tggatgatca ataatgaccg ttactttaca gagaatgsag    5040
gtggattgat gcaattaaat aaagataaaa tgctattgaa tgcctggaca gaggataata    5100
aagaaacaga tgttccaaaa ttgggacagt ctcctcagtt tgatacgcat ttgttggaga    5160
atgcttcttt cctgcgtttg aagaatctca aactcaccta tgtactcccc aatagtcttt    5220
ttgctgggca gaatgtgatt ggtggagctc gtgtctattt gatggcgcgc aatctgttaa    5280
ctgttacgaa gtataaaggc tttgaccctg aagcaggggg gaatgtggga aaaaatcaat    5340
atcctaattc taagcagtac gttgcgggta ttcagttgtc tttctaagat ttacttattc    5400
ttaagaaaca tttgatatga aaaaataat ttattgggtt gcgacagttt tcttagcagc    5460
gagcgtatcc tcttgcgagc ttgaccgcga ccccgaagga aaagatttcc aacagccata    5520
tacttctttc gtgcagacga aacaaaacag agatggtctt tacgcacttt tgcgtaatac    5580
tgaaaatcca cgaatgcatt tttatcagga acttcaatcc gatatgtatt gcactaccat    5640
tactgatggt aactccttag ctccgttcgt gaattgggat ttaggcatac ttaacgacca    5700
tggacgtgct gatgaggacg aagtctccgg tatagctggc tactatttcg tatacaatcg    5760
actaaatcag caagcgaatg cttttgttaa caatacggaa gctgcgttgc agaatcaagt    5820
gtataaaaat tccaccgaga tcgccaatgc taagagcttt ttggcggaag gaaaagtttt    5880
acaagcattg gctatttggc gactgatgga tcgttttagc ttccatgaaa gcgtgacaga    5940
agttaattcc ggtgcgaaag atcttggcgt tattctgttg aaagaatata atcctggtta    6000
tatcggtccc cgtgcaacga aggcacaatg ttatgattac attttgtcac gtttgtctga    6060
ggctattgaa gttttgcccg aaaacaggga aagcgttctt tatgtgagcc gtgattacgc    6120
ctatgccctc cgagcaagaa tttacctcgc gttgggtgaa tatggaaaag ctgcagcaga    6180
tgctaagatg gttgttgata agtatccttt gattggtgca gcagatgctt ctgagtttga    6240
gaatatttat cgatcagatg ctaataatcc cgaaattatt tttcgtggtt ttgcttctgc    6300
gactcttggc tcgtttactg ctacgacact aaatggtgct gcgccagcag gtaaggatat    6360
aaaatataat ccgagcgcag tcccttccca atgggtagtg gatctttatg aaaacgaaga    6420
```

FIG. 3C

```
tttccgcaaa tccgtatata tcgcgaaagt tgtgaaaaag gataaggggt atttagtaaa    6480
taaattcctt gaggacaagg cttatcgtga tgttcaggat aagccaaacc ttaaagtcgg    6540
agctcgttat tttagcgttg ctgaggtcta cttaattttg gtagagtctg ctcttcagac    6600
tggagatacc ccaacagccg aaaaatatct caaggctttg agtaaagctc gtggagcaga    6660
agtttcagtc gttaatatgg aagcactgca agcagagcgt acgcgtgagc ttataggtga    6720
gggtagtcgt ttgcgtgata tggtccgctg gagtatccct aataatcatg atgcttttga    6780
gactcagcct ggtttagaag gttttgcaaa tactactcct ttgaaagctc aagctcctgt    6840
aggcttttat gcatatactt gggagttccc acagcgagat cgacaaacta atccgcagtt    6900
aataagaac  tggccgatat aatttagttg tagatcttac tatgaaatat ggggctgcat    6960
caaaattttt tttgtcgcag cccctatctt ttcatactca taatacgagg aagccccaac    7020
tttcacaagc tagggctttg ttcgtttctc aattttggga aaattggggg atatcaacaa    7080
attaatgggt gaaaagttgt gtttccctcc ttgtgtagtc gtcccttaaa aggactctta    7140
agggacgact aaatatgctt ttcaatacgc ccatgatctt tctctattgt ttcccaagaa    7200
tgaagcttat atttccctga aaacgcatct tggacatctt caaacaaata cttctgatta    7260
gctttgaggc taagaatata gtcggcctct gattgaataa tcacttcagc aatagctgtt    7320
tgtattccca ttgcatcaat actaacaact gatccactta aatcaagact atccggtact    7380
tcgggaatag cttgtaattc attgtgtttg tctgtaactg tctcttgaca agacttaagc    7440
tcacttgatc aatccatgcc gagagtatat atgtacaccc agtcttcttt gggagctacg    7500
caaacgcttg ccatctatgg caatatgttt accctctaaa tcgctaatca agtcttttcc    7560
ataaacactg agacaagcgt aaagagcaat gaggttcaat gtgttggagt acacgctcaa    7620
acgtatctgc ggcaggacag ccgttaggaa gttcaaccaa tggacgaaag gattcttctc    7680
gctctaaacc cagttcgtgc attgactcat aatcctatcc accaaacaga taactcgcca    7740
aggcgataac taaatgtcg  cttaacttat acttacagcg acctacaaca cgaggatctt    7800
ttacctcctt gaaaaatctg ttacatgcat aatcccaaag atatccttat tttgatgcgg    7860
ttgccctgga tgcgatagcc tgcaattgtt acataagtcg gcagatatct tatctttgta    7920
cacaaaatta ttataggtat gtgcaagaaa catttcatcc gatatctctt ttggatttt    7980
atctcctttt gctcaggtat agctttggtc tcttgtaagg agtccaagtt agatctcgaa    8040
gacgtgaatg tggttgatct gcaaatccac cgattctacc tttctactaa gaagaatccg    8100
gatttagaaa aagtgttttt ctctatcgat catgcaaaag ggacaattgt taataagaaa    8160
tatatgcctt atggcacggt tttagattct gtcctaatga atctcgttac ggatctctct    8220
gcaaaaaagt tgcaagtagc ggttaatgat ggggagtata agattggca  taataaagat    8280
tcgttgtggt tgcgcgattg tcataccttg catttaatgg ttttcgacga aagtggcgag    8340
aaaacg                                                               8346
```

FIG. 3D

<381> 7227 bp DNA

| | | | | | |
|---|---|---|---|---|---|
| tgtgaagaag | atgatgctat | tgcgactata | ggactgttgt | tcttccatac | agtagctttc | 60 |
| agcatctgat | atttctctca | aaccaagtaa | ggggagtcg | cgagtatttc | atttgcggct | 120 |
| ccccttgat | ttttctcttg | tggcaggaag | tgagtcgaga | tgccatggtt | ttccttttt | 180 |
| tgattcccga | atccgttccc | cgaaagagat | gtttgggttg | aggaaaattg | acgaatcgtt | 240 |
| tttgctctta | tgggaatccc | tccgaatcac | agttctcgag | gagaaaagaa | cattactcat | 300 |
| tgccggggat | taatacctgc | gatttatagc | gagtctgccg | gcattacaat | cttcctcttt | 360 |
| aggatcttac | atcacatgtc | acgttgcaga | aatttctgca | tttgtggttt | ctaaaaacgt | 420 |
| ggcgcgtaaa | cttttcatt | ttggcgcgag | aagtaaaaaa | atctcgagcc | aaaacgaaaa | 480 |
| aaatcctgcg | ccactttatt | ccataaaatc | gaaccgaaat | cgaagtgttt | taggctcgta | 540 |
| ctccggaaac | agtagttcac | aagcatcagg | agaatagcat | tgatgtggaa | tcaaggtatc | 600 |
| tcaatattga | gagcgttcga | tcggtcaaaa | gaaacactct | atcttccaaa | attcaaattt | 660 |
| acatcggttt | attgctgctc | cttttgcaaa | gtggatttga | caaatcgtat | ggtgagcaaa | 720 |
| ttgcttagat | gaaaaaagg | ataataggat | tagtctggtt | gcattttttt | atttagtttt | 780 |
| gtggctgtcc | gtatcatagg | acagttgtgg | aagtttcgtg | acttgtgtct | aacgccggta | 840 |
| gcggcttttt | gagacttccc | ttggttaggg | taaaaccgga | gaagaaaaga | aaacaacata | 900 |
| acagtaataa | ttttaagttt | aacgcaaaag | aaaagtctat | gaaaagaatg | acgctattct | 960 |
| tcctttgctt | gctgacgagc | attgggtggg | ctatggccca | gaatagaacc | gtgaagggta | 1020 |
| cagttatctc | ctccgaggat | aatgagcccc | tgatcggcgc | gaatgtcgtg | gttgtcggaa | 1080 |
| acaccacgat | cggtgctgca | accgacttgg | atggcaactt | cacgcttagc | gtgcctgcca | 1140 |
| atgccaaaat | gttgagagtg | tcctattccg | gtatgactac | caaagaggtc | gccatcgcta | 1200 |
| atgtgatgaa | gatcgtactg | gatccggact | ctaaggttct | ggagcaggta | gttgtattgg | 1260 |
| attacggtac | gggacagaaa | ctcagcactg | tttccggttc | tgtggccaaa | gtgtccagcg | 1320 |
| aaaagctcgc | ggaaaagcct | gttgccaaca | tcatggatgc | cctccaaggt | caggtagccg | 1380 |
| gtatgcaggt | tatgacctct | tcgggagacc | ctacgaaggt | ggccaacgta | accattcacg | 1440 |
| gtaccggatc | tttgggcgca | agctcttccc | cactttatat | cgttgatggt | atgcagacgg | 1500 |
| atctgtcagt | ggtggctacg | atgaacccga | atgattttga | caacgtaaca | gtcttgaagg | 1560 |
| atgcttctgc | aacttctatt | tacggtgcgc | gtgctgccaa | tggtgttgtg | attatcacta | 1620 |
| ccaagagagg | taaaatgggt | gaagccggcc | gtattacatt | caattacagc | tacggtgttt | 1680 |
| cttctattat | cagtaagaag | cctatgagcc | gaatgatgac | tggagacgag | cagcttaact | 1740 |
| atcagtttaa | taatggttat | tgggatacta | ctaagccgga | gtatgcaacg | atcgaagcag | 1800 |
| tcaaagctac | tttgatcaaa | aatgcagagg | atatgtatgc | caaatacccg | gagcttgctc | 1860 |
| ctcttgtgaa | atccggatat | ttaaagccaa | ttgattttga | taatgatacc | gactggcttg | 1920 |
| agtatttcat | tcgtcctacg | gctccgacgc | accaaggtga | tatttctttc | accggaggaa | 1980 |

FIG. 4A

```
gtcaggggac ctcttatttt gtttctttgg gttatttcaa tcaagaaggt atttcccgtg  2040
agccttcttc tttcaagcgc tatagcggcc gtatgaattt ggaaagccgt attaaggaat  2100
ggctgaaatt aggtctgaat ctttcgggtg caatcgctga aaagcaagca tcatcgttct  2160
caggaaccaa ttattataat acaggaactt ttggtgcatt atctatgcct aagtatctga  2220
atcctttaac gagtgatggt gagattgccg acgtatacta tatcatagga accactcctc  2280
gccaaagtcc attgcgaatt gctaaatggt accccgaaga agattatact tatcaagcaa  2340
atgttggtgg atatttgcag ttcaatccga ttaagggact tacaattaag tcgcaagcgg  2400
gtttggactt tacggacagc cgtgctacag taaagacact tccgaataat attttttctc  2460
ctaatcctct gggcaacagg acagagcgct tctatggcgg acggttgttt acagtcacaa  2520
acaccggtga gtataaaacc aattttgaag agttgcacga tgtgaccatc cttttgggac  2580
aagaatttat tgatgcagat gtggatgttt cagcgcaag agcaaatggc ttcgagaaca  2640
gcaaggtaat gcttttgtct caggaaaaga ccggtaattt ccttcagctt cctgctcagc  2700
gaaaagaaga atatgcttat ttgtctttct tcggtagggg tagttatgga tttgacaagt  2760
ggatgtatct ggatgtttcg ttgcgtaatg accaatcatc tcgttttggt gacaacaatc  2820
gtagtgcttg gttctattct ttcggttcga tgttcgacat ctacaataag ttcatcaagg  2880
aaagcgattg gctgagtgac ctccgattca agctgagtta cggaactacc ggaaactctg  2940
agatcggaaa ctacaaccac caggctctcg taggaagcaa taattatacc gatacagcat  3000
tgggccttac tgtctctaca attggtaacc ccgatctttc ttgggaaaag caatctcagt  3060
tgaatgtggg tattgcttcc ggttttttgga acaatcgttt gactgctgaa gttgatttct  3120
acgttcgtac aacggatgat atgttgatca atgtgcctct gcagtatata agtggtttca  3180
ccaaccagtt ccagaatgtc ggctcaatgc aaaatacggg agttgatgtt aacttgagag  3240
gaactatctt ccaaaataaa gattggaatg tttatgctgc tgcaaacttc aactacaaca  3300
aacagaagat taccaagctc ttcttcgatt tgaaagagta tgtacttccc aacaccggaa  3360
ctatctggca gattggaaaa cctaattcat tctatatagc tgagtatgca ggtatttata  3420
agggtacgga gccttatacc gacccggatg gaaatgttta tcatggtggt gatcagttgt  3480
ggtatgttcc cggcaaaaca tgggctgatg gtactccggc tacaacgaat gtctattctg  3540
cggatttgga gcaagcggta gataaggcag tcaatccccc tattaccggt ggtttctctt  3600
tgggggcttc ttggaaaggt ctttcattgg atgctgattt tgcttatatc attggtaagt  3660
ggatgatcaa caatgaccgc tacttcactg aaaacggttc tggcgctgca atgagaacca  3720
ataaggataa aatccttttg gatgcatgga ctccgcagaa tcctaactca gatgttccaa  3780
gactgggtca agacaatcag ttcgatagcc gtttgctgga gaatgcctct ttcttgcgtc  3840
tcaagaatct gaaattgact tatgtccttc ctcaatctct attcaagact caaggtgttg  3900
tttctggagc acgtgtttat ttgatggctc gtaacctcct gaccgttacc aagtacaaag  3960
gttttgaccc cgaagccggt ggtaatgtgg cactgaatca attcccgaat acgaagcaat  4020
```

FIG. 4B

```
ttgtaggtgg tattcagatt tctttctaaa cattgagtac taacgattaa cagtaaatca    4080
ttatgaagaa aatattttat gcagtgctgt ctgctttcct gctgttgggg cttttttcat    4140
gcgatctgca gcgtgatccg gatggaagtg atgaacagaa agatcatttc gcttcttttg    4200
tggagacaaa acattttaga gatggttTgt atgctacgtt gcgaagtaca gaaaaccCta    4260
ctcgtttcgt atggcaggat cttcaatcag acatgtatgc agtaacaacg aatgatggta    4320
atacaagctc tcgttttatc acatggagtt tgggtgcact ggagtcatcc ggtgagattg    4380
cttcatatta tctcgcttat tatagcttgt tgcagcgcgc caattatttt gtgaccagaa    4440
tagaacgttc tatggagttg aatctttatc tggagaaaga actcaaagat gtaaagatct    4500
ttcaagcaga aggtaagact cttcaggcat tggccctctc tcgtttgatg gagcgttttg    4560
cttataagta tgatcctgcg gccactactc atccgtatga tttgggtatt gtacttgtta    4620
aggattacaa tcctatgatt gctgcacctc gtaatacgca gaaagagtgc tacgattata    4680
tccttgaatg cttaaatcag gcgattgatg ttttgccgaa caagagcaat gaaggtaata    4740
tcagagtttc caagcattat gctcatgctt tgcgtgcacg tgtaaatttt gcaatgggta    4800
attatgatgc ggcaaaagaa gatgctaaag ttctggtcga caattatcct cttattgatg    4860
tgacgacagc aaagaaattt gctgaggttt accgcgatga tgctaacaac cccgaaatcg    4920
tattccgtgc ttttgcttca ggaactatcg gtactgttgc agaaacgacc ctaagcggat    4980
tcttgtggca ttcaggtgct cagcttgtgg tttcaagtcc tatttcagct cctttccaat    5040
gggttgttga cctatatgat gataccgatt atcgtaagtc ttgctatatc acgaaagatt    5100
tctacgttat tggtggtggt gttgataagg gttatgtagt tggaaaatat ctgggtaacc    5160
ccgcttatca gtctaatcct aacgtacccg actttaaggt gaccagccgc ttcttctcag    5220
ttgcagaggc ttatttgatc atggcagagt ctatggccaa gtccggtgat gcagccggtg    5280
caaaggatct gttgaagacg ctttgtgaga acgtggtgg ccagttggaa gatggcgata    5340
tcatggatTt ggtaatggca gaacgtaccc gtgagctgat cggagaaggc tctcgtctga    5400
acgatatgat tcgttggaat ttgcctaata accacgatga tatggaaaat cagccggtat    5460
tcctgcagat cggtcttgca aaagctgata agctgaagca gcccgtacct gccggtcact    5520
atgcgtttac ttgggagttc cctgttaggg atcgtcaggt gaatccgcag attatcaaaa    5580
actggccgaa ctaattcaat tagatgtttc gacgcgcttg gggttaatct ttataatccc    5640
aagtgcgttt gaaacctttt ttgacttta ggcgaaaaga gctttctgtg gtgtgtttgg     5700
aatcgtgcca agaaagtcca aaatataaac ggttccggtc aaacaaaaat caaattcaaa    5760
ttatgaagaa aatttctct ttgttgggtg ctatgttctt gatgggttca ctcagtgctc     5820
aaaacacaat cccccaatct ttctcttgtg aagtaagcgg atcagcacgt gctatcgagt    5880
gtttggatgg ctctgttttt tctcaggccc cggtagaatt cgatactgga tatccttcta    5940
attctgggat agaactgatg caggcgcaga atgtgaaagg tgtaagctct atttctgcta    6000
tccgtttctt tggtattcag ttggtttatg caggtggctg ggcagttcaa aacgattttg    6060
```

FIG. 4C

```
accctatgac ctttactgta aagatttgtg ctaacgagaa tggtttaccc ggtgcagaaa    6120
tctactcaca ggaagtcgct ttgaatcata acgatacagg tgaaactttt ggtaataatc    6180
ctatcagtat tttctattgg gactttgagc ctgctactcc tattaacaac ttgccggccg    6240
atttctggct tgtaatctct aattcagatt ccgaagcatg gttcctttgg attgatcaga    6300
aagatggtgt aggaccgatt gctacatttg gaacgcagca aggtgagcct gagggtactc    6360
ccagccactg gttcctgaga gagggagctc caggcttagg tgtttgcatt aagggaacac    6420
cttcaggtgt tgatatgatc gaggctaata agccatattc gctttcagta agtggcaata    6480
caatttctgt agacgcagga gaggtaacca tttatgatat gaacgctcgt cgagtagcat    6540
atgctgaaaa gggaatttct tatactgctc aagccggaac atatgttctc cgtattgtag    6600
tagatggcat gacatatgtt gaaaaagcgg tggttaccaa gtaaggacac gttttgtttta   6660
gatatatagt ctaatttaat gttgaggagg tatgtcttta tggcatacct cttctttttt    6720
attttttact ttgccacagc cacaagcgta ttgcccgtca tgcatatctc aaattgttcc    6780
tctccactat ctttaattgc gacataagtc ggcagatgtc ttatctttgt acactaaata    6840
tcagtaggta tgtgtaagaa acatttcatc cgatacttct tttggactat cattgtcttt    6900
tttgtgggtg cggctattca ctcttgtaaa gagtctaaga tagatcttga agaagttagc    6960
atagtcgatc tgcaaatcca ccgtttctac ctttccagta agaagaatcc ggatttggaa    7020
aaagtatttt tctctatcga tcatgcaaaa gggacaatta ttaataagaa atatatgccc    7080
tatggcacag ttttggattc tgtaatgatg aaactcgtta ctgatttctc tgcgaaaaaa    7140
ctgcgagtgg ccatcaatga tggagaatat aaggattggc ataataagga ttcattgtgg    7200
ttgcgcgatt gtcataccTT acattta                                        7227
```

FIG. 4D

CLUSTAL W (1.82) Multiple Sequence Alignments (DNA)

```
Sequence format is Pearson
Sequence 1: QMLragB        1518 bp
Sequence 2: ThairagB       1506 bp
Sequence 3: W50ragB        1506 bp
Sequence 4: 381ragB        1518 bp
Start of Pairwise alignments
Aligning...
Sequences (1:2) Aligned. Score:  56
Sequences (1:3) Aligned. Score:  62
Sequences (1:4) Aligned. Score:  60
Sequences (2:3) Aligned. Score:  58
Sequences (2:4) Aligned. Score:  53
Sequences (3:4) Aligned. Score:  59

Start of Multiple Alignment
There are 3 groups
Aligning...
Group 1: Sequences:    2         Score:18441
Group 2: Sequences:    3         Score:18620
Group 3: Sequences:    4         Score:17151
Alignment Score 28845

QMLragB       ------ATGAAAAAGATATTATATTGGGCTGCGGCAGCTCTTTTTGCTGT---GAGTCTC  51
381ragB       ATCATTATGAAGAAAATATTTTATGCAGTGCTGTCTGCT-TTCCTGCTGTT--GGGGCTT  57
W50ragB       ------ATGAAAAAATAATTTATTGGGTTGCGACAGTTTTCTTAGCAGC---GAGCGTA  51
ThairagB      ATGAAAATGAAAAAAATAATTAATTATGCTGTGGCCGGATTGCTACTCGTTTCAAGCTTT  60
                    *****  **  *** *  **    *    * * *      *      *  * *

QMLragB       GTTTCCTGCGATCTGAATAGAGATCCGGA---AGATAAGGCCAAGAAAGAGCCCTTCAAA 108
381ragB       TTTTCATGCGATCTGCAGCGTGATCCGGATGGAAGTGATGAACAGAAAGATCATTTCGCT 117
W50ragB       TCCTCTTGCGAGCTTGACCGCGACCCCGA---AGGAAAAGATTTCCAACAGCCATATACT 108
ThairagB      GCCGCTTGTGACTTGGATCGCACTCCTCA---CAATTCTGATGTCCAAAAGCCTTATGAA 117
               *  ** **   * *         **  *        *      **  *  *

QMLragB       ACAATAGCTCAGGCTCGTCAGAGCAGAGATGGCTTGTATTCTCTGCTTCGTGAATCGGAG 168
381ragB       TCTTTTGTGGAGACAAAACATTTTAGAGATGGTTTGTATGCTACGTTGCGAAGTACAGAA 177
W50ragB       TCTTTCGTGCAGACGAAACAAAACAGAGATGGTCTTTACGCACTTTTGCGTAATACTGAA 168
ThairagB      GATATGGCCACCACAGTTCAGTATAGAGATGGATTGTATTCTGTTCTTCGTGGTGCAGAG 177
               *  *        *   **  ******* * ** *   *  *  *   *  **

QMLragB       CAATTAGCTTTCCATGTTTATGACGAGGTTCAGTCGGATATGTACACTACTACCAAGAAC 228
381ragB       AACCCTACTCGTTTCGTATGGCAGGATCTTCAATCAGACATGTATGCAGTAACAACGAAT 237
W50ragB       AATCCACGAATGCATTTTTATCAGGAACTTCAATCCGATATGTATTGCACTACCATTACT 228
ThairagB      AATGCCGGACGGTATACTTTGTCAGAATATATGTCCGATATGTATTGTGTAATGCAAGGA 237
                *            *      **  * *  ** ** *****    *

QMLragB       GATGGCAACCAGTACTATCCATTCGTAGCTTGGCAGTTAGGAAGCATGGAAACTCATGGT 288
381ragB       GATGGTAATACAAGCTCTCGTTTTATCACATGG-AGTTTGGGTGCACTGGAG-TCAT---  292
W50ragB       GATGGTAACTCCTTAGCTCCGTTCGTGAATTGGGATTTAGGCATACTTAACGACCATGGA 288
ThairagB      GATGGTGGCCATGCTACGCCTTATGTTACATGGACGATTCCTCGCATTGAGATTG----- 292
              *****         *   *   ***   *

QMLragB       CGTGCTGATGAGGATCAAGTATATGGTATTGCCGGTTATTACTTCGAGTATAGCCGTCTG 348
381ragB       ----CCGGTGAG--------------ATTGCTTCATATTATCTCGCTTATTATAGCTTG  333
W50ragB       CGTGCTGATGAGGACGAAGTCTCCGGTATAGCTGGCTACTATTTCGTATACAATCGACTA 348
ThairagB      ----CTGACCAC----------------GCATCGAATTATTACTTTGGTTTTAATCGGTTA 333
                  *  *                    *    *  ** ** * *       *  *
```

FIG. 5A

```
QMLragB      ATTCAGCAGGCAAACTCCTATATCGAAGATATGGAAAAAGCTCTTGCCAATAATACTGAT 408
381ragB      TTGCAGCGCGCCAATTATTTTGT----GACCAGAATAGAACGTTC--------TATGGAG 381
W50ragB      AATCAGCAAGCGAATGCTTTTGTTAACAATACGGAAGCTGCGTT----------GCAGAA 398
ThairagB     ATTCAGCAAGCCAATGCTTTTGTCGGAAATGTTAAGCTGGCAAT----------CGCAA 382
                 ****  ** **    *  *      *       *    * *                *

QMLragB      ATGAGCATTTTCATTTCCTCCGAAGAAGTGGAACGTGCTAAGAGATATCTCGCAGAGGTA 468
381ragB      TTGA--ATCTTTATCTGGAG-AAAGAACTCAAAGATGTAAAGATCTTTCAAGCAGAAGGT 438
W50ragB      TCAA--GTGTATAAAAATTCCACCGAGATCGCCAATGCTAAGAGCTTTTTGGCGGAAGGA 456
ThairagB     ATGGG-GTTTATAAGACAGAAGTTAAAAACCAATGCTCAAATTTATTTGGCTGAGGCC 441
                *  *            **        **     **  *  *  *  ** **  *

QMLragB      CGTGTTGTACAAGCTTTGGCGAATTGGCGTTTGATGGATCGTTTT-GCAT--ATAAATAT 525
381ragB      AAGACTCTTCAGGCATTGGCCCTCTCTCGTTTGATGGAGCGTTTT-GCTT--ATAAGTAT 495
W50ragB      AAAGTTTTACAAGCATTGGCTATTTGGCGACTGATGGATCGTTTTAGCTTCCATGAAAGC 516
ThairagB     AAGACTTTGCAGGCTTTAGCTTTGTTCCGTCTTATGGAGCGCTTT-GCCT--ATCCCTAT 498
                 *  *  ** **  ** **        *  ***** ** ***  *  *    *  *  *

QMLragB      GATGCCGCATCCAATCAAAGTCCTCAAAACCTTGGCATTGTTTTGATCAAGGAATTCAAT 585
381ragB      GATCCTGCGGCCACTACTCATCCGTATGATTTGGGTATTGTACTTGTTAAGGATTACAAT 555
W50ragB      GTGACAGAAGTTAATTCCGGTGCGAAAGATCTTGGCGTTATTCTGTTGAAAGAATATAAT 576
ThairagB     GATCCAAACGAAACCACTTCTCCGAAAAACTTGGGGGTGGTTTTGATAAAGGAATATGAT 558
             *    *          *   * *  *     *  *      *    *  * ** **    **

QMLragB      CCCGCTTATATCGGCCCCCGTGCTACTCAGAAGGAGTGTTATGATCACATCCTCTCGGCT 645
381ragB      CCTATGATTGCTGCACCTCGTAATACGCAGAAAGAGTGCTACGATTATATCCTTGAATGC 615
W50ragB      CCTGGTTATATCGGTCCCCGTGCAACGAAGGCACAATGTTATGATTACATTTTGTCACGT 636
ThairagB     CCTTGGGCTGTGGGTGCACGAGCTACGCAGACGGAAACGTATAGCTATATTATGAGCCTT 618
             **           *    *   *  **   **    **       *     *  **  *

QMLragB      TTGGAGGCTGCTATTACGGTATTGCCTGAGAAGAACCCTGACGGCATCACATATGCCGGA 705
381ragB      TTAAATCAGGCGATTGATGTTTTGCCGAACAAGAGCAATGAAGGTAATATCAGAGTTTCC 675
W50ragB      TTGTCTGAGGCTATTGAAGTTTTGCC----CGAAAACAGGGAAAGCGTTCTTTATGTGAGC 693
ThairagB     CTTGATGAGGCCATCTCTGTTTTGCC----TGAAACGAATGCGAACAATATGTATGTGAGT 675
                *    ** **     **  *****         *    *            *

QMLragB      CGTGACTACGCTCATGCTTTGCGAGCACGTGTACACCTTTCTATGGGTAACTATGCCGAT 765
381ragB      AAGCATTATGCTCATGCTTTGCGTGCACGTGTAAATTTTGCAATGGGTAATTATGATGCG 735
W50ragB      CGTGATTACGCCTATGCCCTCCGAGCAAGAATTTACCTCGCGTTGGGTGAATATGGAAAA 753
ThairagB     CGGGATTATGCTTTAGGCTTGCGTGCTCGCGTACACATGGCGATGGATAACTATGCTGAA 735
                *  ** **      *  *   **  **       *   **  *  *  *   ****

QMLragB      GCACTTGCAGATGCTAAGCAGATTGTGGAGAAGTATCCTTTGATCAACGCTAACAATGCA 825
381ragB      GCAAAAGAAGATGCTAAAGTTCTGGTCGACAATTATCCTCTTATTGATGTGACGACAGCA 795
W50ragB      GCTGCAGCAGATGCTAAGATGGTTGTTGATAAGTATCCTTTGATTGGTGCAGCAGATGCT 813
ThairagB     GCCGCCAATGATATCAGAGCTTTTTATAAAAGTACAATCTGATTTCTGCTGCTAATTCC 795
             **      *** *    *    *   **  *  *  * *    *   *       *

QMLragB      GAGGATTTTGCTAAAATCTATCGTTCAGATGCTAACAATCCCGAGATCGTATTCCGTGCT 885
381ragB      AAGAAATTTGCTGAGGTTTACCGCGATGATGCTAACAACCCCGAAATCGTATTCCGTGCT 855
W50ragB      TCTGAGTTTGAGAATATTTATCGATCAGATGCTAATAATCCCGAAATTATTTTTCGTGGT 873
ThairagB     GATGAATTTGAGGAGGCTTATAGAAAGATGAGCTCCAATCCTGAGCTTATTTTCCGCGGA 855
                * ****    *   **  *      *     *  ** ** **  ** ** *

QMLragB      TTTGCATCTCCTACGACCGGTGCTGTTGGTGCAACCTCTCTTAATGGCGCATCTGTGGTG 945
381ragB      TTTGCTTCAGGAACTATCGGTACTGTTGCAGAAACGACCCTAAGCGG-ATTCTTGTGGCA 914
W50ragB      TTTGCTTCTGCGACTCTTGGCTCGTTTACTGCTACGACACTAAATGGTGCTGCGCCAGCA 933
ThairagB     TATGCTTCCGTTACTAACGGATACCTTG-TGTATCAGGATTTGATGG--GAGCAACAGCT 912
                *** **   **     **      *    **     *        *       *

QMLragB      AATAAGA----AGATTAAATATGCGCCGTTTATC---GTTCCCTTGCAGTGGGTAGTCGA 998
```

FIG. 5B

```
381ragB      TTCAGGTGCTCAGCTTGTGGTTTCAAGTCCTATTTCAGCTCCTTTCCAATGGGTTGTTGA 974
W50ragB      GGTAAGG----ATATAAAATAT---AATCCGAGCGCAGTCCCTTTCCAATGGGTAGTGGA 986
ThairagB     TCTGGAA-CTAATGTGAAGTAC---AACCCTCGTGTTACCCCTCTGCAATGGGTTTGCGA 968
                  *  *               **   * ** *****   **

QMLragB      TTTGTACGAAGATGCAGATTATCGCAAGTCAGTCTATATTGATAAGA---------CAGT 1049
381ragB      CCTATATGATGATACCGATTATCGTAAGTCTTGCTATATCACGAAAGATTTCTACGTTAT 1034
W50ragB      TCTTTATGAAAACGAAGATTTCCGCAAATCCGTATATATCGCGAAAG------------- 1033
ThairagB     CCTTTATGATGCGGCTGATTATCGTAAGAAAGTGTACATTGTAGACAA---------GGT 1019
                * ** **     ****  ** **   ** **          *

QMLragB      TAGTAACGGCAGTGAAAAGGGATATTTGGTGAACAAATTCCTTGAAGATCCTGCCTACAG 1109
381ragB      TGGTGGTGGTGTTGATAAGGGTTATGTAGTTGGAAAATATCTGGGTAACCCCGCTTATCA 1094
W50ragB      TTGTGAAAAAG--GATAAGGGGTATTTAGTAAATAAATTCCTTGAGGACAAGGCTTATCC 1091
ThairagB     GAACGGTGACGGTGGCAAAGGTTATGTCGTAAATAAGTTCCTTGGAGACCCTGAACTTCG 1079
                **  **  *** *  *   ** *  **  *    *

QMLragB      AGAAACAGCCGATATCCCCATTCTGAAAATAGGGGTACGTATGTTCAGTATTGCAGAAGC 1169
381ragB      GTCTAATCCTAACGTACCCGACTTTAAGGTGACCAGCCGCTTCTTCTCAGTTGCAGAGGC 1154
W50ragB      TGATGTTCAGGATAAGCCAAACCTTAAAGTCGGAGCTCGTTATTTTAGCGTTGCTGAGGT 1151
ThairagB     TGAAGACCCTAAGAAGGAAAATTTCAAAACCGGTTGTCGTTTCTTCTCTCGCAGAAGC 1139
                     *          * **         **     **       *  ** **  *

QMLragB      TTATCTGATGGTAGCTGAGTGTGCTCACATGACAGGAGACGATGCTACGGCGATTGCATA 1229
381ragB      TTATTTGATCATGGCAGAGTCTATGGCCAAGTCCGGTGATGCAGCCGGTGCAAAGGATCT 1214
W50ragB      CTACTTAATTTTGGTAGAGTCTGCTCTTCAGACTGGAGATACCCCAACAGCCGAAAAATA 1211
ThairagB     CTATCTTATCTTGGCAGAAGCAGATATTATGACTGGTAATACAGCCGAGGCTATGGAAGT 1199
                **  * **  * **      *   *   *      *

QMLragB      CCTCAAAAAGCTCAGTGCTGCTCGTGGTGGCAATATTGACACCGGTGATGTAATGAAAGC 1289
381ragB      GTTGAAGACGCTTTGTGAGAAACGTGGTGGCCAGTTGGAAGATGGCGATATCATGGATTT 1274
W50ragB      TCTCAAGGCTTTGAGTAAAGCTCGTGGAGCAGAAGTTTCAGTCGTTAAT---ATGGAAGC 1268
ThairagB     TCTGAAAGAGCTGAGTAAGTCTCGTGGAGCAGAGGTTTCCGGTGCAGATTATATGCAAAT 1259
                * **       * **   ***** *   *        *   **  *** *

QMLragB      TATTCAAGAAGAACGTACTCGTGAGGTTATCGGTGAGGGCGCTCGTTTGCGCGATATGAT 1349
381ragB      GGTAATGGCAGAACGTACCCGTGAGCTGATCGGAGAAGGCTCTCGTCTGAACGATATGAT 1334
W50ragB      ACTGCAAGCAGAGCGTACGCGTGAGCTTATAGGTGAGGGTAGTCGTTTGCGTGATATGGT 1328
ThairagB     CCTCAAGGATGAGCGTACACGAGAAATGATCGGTGAAGGTTCTCGTCTCAATGACATGAT 1319
                 *     *  ***** **  **     * ** **  ****  *  ** *** *

QMLragB      TCGTTGGAATCTT--CCGAATATC---GACAAAACAGAAATCCAACC--TGCTCTTACTG 1402
381ragB      TCGTTGGAATTTG--CCTAATAACCACGATGATATGGAAAATCAGCCGGTATTCCTGCAG 1392
W50ragB      CCGCTGGAGTATC--CCTAATAATCATGATGCTTTTGAGACTCAGCC--TGGTTTAGAAG 1384
ThairagB     TCGCTGGAATATGGATTTGGTGGTATCTCCCGTTCAGGCTGTTCTTCA-TAAAATAGCTG 1378
                ** *****  * *          *             *        * *

QMLragB      GTTATGC--TCGTGAGATCGTAT----TGGAGCAACCTGTTCCGGCCGGTCACTATGCAT 1456
381ragB      ATCGGTC--TTGCAAAAGCTGATAAGCTGAAGCAGCCCGTACCTGCCGGTCACTATGCGT 1450
W50ragB      GTT------TTGCAAATACTACTCCTTTGAAAGCTCAAGCTCCTGTAGGCTTTTATGCAT 1438
ThairagB     TCCCGACTATCCTTCAGACTGATGACCCGA---CACGTGTTCCTGCCGGCTTCTATGCTT 1435
                *          *       *         *   *    **   **    ***** *

QMLragB      TTACATGGGAGTTCCCTAACCGAGATCGTCAGGTTAATCCTCATTTGATCAAGAACTGGT 1516
381ragB      TTACTTGGGAGTTCCCTGTTAGGGATCGTCAGGTGAATCCGCAGATTATCAAAAACTGGC 1510
W50ragB      ATACTTGGGAGTTCCCACAGCGAGATCGACAAAACTAATCCGCAGTTAATAAAGAACTGGC 1498
ThairagB     TCACGTGGGAAATTCCCAATCGTGATCTTGTAGTTATTCCCGAGCTGGTTCGCAACTGGC 1495
                ** *****  * **   * ****       * ***   *  *  *    ******

QMLragB      AA --------- 1518
381ragB      CGAACTAA  --- 1518
W50ragB      CGA  TATAA --- 1506
ThairagB     CAAAACAGTAA 1506
```

FIG. 5C

CLUSTAL W (1.82) Multiple Sequence Alignments (peptides)

```
Sequence format is Pearson
Sequence 1: QMLRagB         505 aa
Sequence 2: ThaiRagB        501 aa
Sequence 3: W50RagB         501 aa
Sequence 4: 381RagB         505 aa Start of Pairwise alignments
Aligning...
Sequences (1:2) Aligned. Score:  45
Sequences (1:3) Aligned. Score:  57
Sequences (1:4) Aligned. Score:  49
Sequences (2:3) Aligned. Score:  47
Sequences (2:4) Aligned. Score:  42
Sequences (3:4) Aligned. Score:  49

Start of Multiple Alignment
There are 3 groups
Aligning...
Group 1: Sequences:    2      Score:8617
Group 2: Sequences:    3      Score:7991
Group 3: Sequences:    4      Score:7664
Alignment Score 8796

QMLRagB      --MKKIL-YWAAAALFAVSLVSCDLNRDPEDKA-KKEPFKTIAQARQSRDGLYSLLRESE  56
W50RagB      --MKKII-YWVATVFLAASVSSCELDRDPEGKD-FQQPYTSFVQTKQNRDGLYALLRNTE  56
381RagB      IIMKKIF-YAVLSAFLLLGLFSCDLQRDPDGSDEQKDHFASFVETKHFRDGLYATLRSTE  59
ThaiRagB     MKMKKIINYAVAGLLLVSSFAACDLDRTPHNSD-VQKPYEDMATTVQYRDGLYSVLRGAE  59
               ****: *   ::   .. :*:*:* *...    :. :   :. : : *****: ** :*

QMLRagB      QLAFHVYDEVQSDMYTTTKNDGNQYYPFVAWQLGSMETHGRADEDQVYGIAGYYFEYSRL  116
W50RagB      NPRMHFYQELQSDMYCTTITDGNSLAPFVNWDLGILNDHGRADEDEVSGIAGYYFVYNRL  116
381RagB      NPTRFVWQDLQSDMYAVTTNDGNTSSRFITWSLGALESSG--------EIASYYLAYYSL  111
ThaiRagB     NAGRYTLSEYMSDMYCVMQGDGGHATPYVTWTIPRIEIAD--------HASNYYFGFNRL  111
             :    . .:  ****  **.    ::  * :  :  . :....     :.**: : . *

QMLRagB      IQQANSYIEDMEKALANNTDMSIFISSEEVERAKRYLAEVRVVQALANWRLMDRFAYKYD  176
W50RagB      NQQANAFVNNTEAALQN----QVYKNSTEIANAKSFLAEGKVLQALAIWRLMDRFSFHES  172
381RagB      LQRANYFVTRIERSMELN-----LYLEKELKDVKIFQAEGKTLQALALSRLMERFAYKYD  166
ThaiRagB     IQQANAFVGNVKLAIANG----VYKTEVDKTNAQIYLAEAKTLQALALFRIMERFAYPYD  167
              *:**  ::    : ::    .: . .    .:   ** :.:****  ***:**::  .

QMLRagB      AASNQS-PQNLGIVLIKEFNPAYIGPRATQKECYDHILSALEAAITVLPEKNPDGITYAG  235
W50RagB      VTEVNSGAKDLGVILLKEYNPGYIGPRATKAQCYDYILSRLSEAIEVLPE-NRESVLYVS  231
381RagB      PAATTH-PYDLGIVLVKDYNPMIAAPRNTQKECYDYILECLNQAIDVLPNKSNEGNIRVS  225
ThaiRagB     PNETTS-PKNLGVVLIKEYDPWAVGARATQTETYSYIMSLLDEAISVLPETNANN-MYVS  225
              .  :**::*:*:::*   .* *: : *.:*: .:*:. *. ** ***:..  ..

QMLRagB      RDYAHALRARVHLSMGNYADALADAKQIVEKYPLINANNAEDFAKIYRSDANNPEIVFRA  295
W50RagB      RDYAYALRARIYLALGEYGKAAADAKMVVDKYPLIGAADASEFENIYRSDANNPEIIFRG  291
381RagB      KHYAHALRARVNFAMGNYDAAKEDAKVLVDNYPLIDVTTAKKFAEVYRDDANNPEIVFRA  285
ThaiRagB     RDYALGLRARVHMAMDNYAEAANDIRAFYKKYNLISAANSDEFEEAYRKMSSNPELIFRG  285
             :.** .****: :::.:*  *  *   :  .:.:* **.. :..* : **..:***:**.

QMLRagB      FASPTTGAVGATSLNGASVVN--KKIKYAPFIVPLQWVVDLYEDADYRKSVYIDK---TV  350
W50RagB      FASATLGSFTATTLNGAAPAG--KDIKYNPSAVPFQWVVDLYENEDFRKSVYIAK---VV  346
381RagB      FASGTIGTVAETTLSGFLWHSGAQLVVSSPISAPFQWVVDLYDDTDYRKSCYITKDFYVI  345
ThaiRagB     YASVTNGYLVYQDLMGATASG--TNVKYNPRVTPLQWVCDLYDAADYRKKVYIVD---KV  340
             :**  *   *  .*  *: ::*:*** *:***. *:***.  *  :
```

FIG. 6A

```
QMLRagB    SNGSEKGYLVNKFLEDPAYRETADIPILKIGVRMFSIAEAYLMVAECAHMTGDDATAIAY 410
W50RagB    KK--DKGYLVNKFLEDKAYRDVQDKPNLKVGARYFSVAEVYLILVESALQTGDTPTAEKY 404
381RagB    GGGVDKGYVVGKYLGNPAYQSNPNVPDFKVTSRFFSVAEAYLIMAESMAKSGDAAGAKDL 405
ThaiRagB   NGDGGKGYVVNKFLGDPELREDPKKENFKTGCRFFSLAEAYLILAEADIMTGNTAEAMEV 400
           .  ***:*.*:*  :    :.   .   :*   * **:**.**::.*.  :*: . *

QMLRagB    LKKLSAARGGNIDTGDVMKAIQEERTRELIGEGARLRDMIRWNLPN-IDKTEIQPALT-- 467
W50RagB    LKALSKARGAEVSVVN-MEALQAERTRELIGEGSRLRDMVRWSIPNNHDAFETQPGLE-- 461
381RagB    LKTLCEKRGGQLEDGDIMDLVMAERTRELIGEGSRLNDMIRWNLPNNHDDMENQPVFLQI 465
ThaiRagB   LKELSKSRGAEVSGADYMQILKDERTREMIGEGSRLNDMIRWNMDLVVSPVQAVLHKIAV 460
           ** *. **.::.  : *. :  *****:****:**.**:**.:    . :

QMLRagB    GYAREIVLEQPVPAGHYAFTWEFPNRDRQVNPHLIKNW--- 505
W50RagB    GFANTTPLKAQAPVGFYAYTWEFPQRDRQTNPQLIKNWPI- 501
381RagB    GLAKADKLKQPVPAGHYAFTWEFPVRDRQVNPQIIKNWPN- 505
ThaiRagB   PTILQTDDPTRVPAGFYAFTWEIPNRDLVVIPELVRNWPKQ 501
                 .*.*.**:***:* **  . *.::::**
```

FIG. 6B

P. GINGIVALIS VACCINE

The present invention relates to a vaccine, which is a complex of all possible outer membrane protein alleles of RagB of *Porphyromonas gingivalis*, and uses of the vaccine to prevent or treat periodontitis caused from different *P. gingivalis* strains.

Periodontal disease is an inflammatory, infectious condition of the soft and hard tissues, which secure the teeth in the mouth. The inflammatory process is driven by a microbial challenge presented by subgingival plaque microorganisms. It is now accepted that *Porphyromonas gingivalis* is a major periodontopathogenic organism which is particularly relevant in the aetiology of adult periodontal disease (2) (10) (14) (17) (26) (36) (39) (45).

Analysis of the microbiology of subgingival plaque in periodontal disease has revealed a very complex mixture of genera and species. However, in recent years, cluster analysis of DNA:DNA checkerboard data and correlation with the clinical status of the sample site from large scale clinical studies involving >16,000 samples by Socransky and colleagues at the Forsyth Institute in Boston USA has revealed that destructive disease is very strongly associated with just three organisms: *P. gingivalis, Treponema denticola* and *Bacteroides forsythus* (*Tannerella forsythensis*) (9) (16) (46) (47) (49).

Genome sequence of *Porphyromonas gingivalis* strain W83 has been completed (33). However, genotypic characterization of *P. gingivalis* strains has revealed extensive heterogeneity in natural populations of this bacterium (3) (12) (15) (23) (25) (28) (30) (35) (37) (56). The development of a vaccine for periodontal disease based on surface and extracellular antigens of *P. gingivalis* has been pursued by several groups worldwide. Cysteine proteases (gingipains), capsular polysaccharide and fimbriae have all been considered (13) (29) (34) (40) (43) (53) (55). However to date few of these studies have addressed the problems of strain variation and the applicability of a single vaccine strategy to counter either allelic variation or post-translational effects caused by variable glycosylation (7).

Current periodontal disease treatment relies upon mechanical debridement, antibiotics and surgery.

Approximately 10-15% of most populations exhibit one of the destructive forms of periodontal disease in the UK. The prevalence of these diseases is reflected in the direct financial costs of treatment, which in 2000/1 were estimated to be £230 million by the National Health Service in England and Wales (Dental Practice Board Annual Report 2001-02). However these costs only apply to actual periodontal treatments provided by general dental practitioners within the NHS general dental services and therefore excludes specialist treatment, any treatment provided by community services and hospital services, any treatment provided privately, and does not include costs associated with treating the consequences of periodontal treatment for example x-rays, detailed examinations, dentures, bridges, extractions and so on. Hence the actual costs to the NHS of treating the consequences of the disease in England and Wales are probably in excess of £500 million and this excludes hospital services or private health care expenditure. The increasing life expectancy in the population and conservation of more standing teeth into later life, due to caries control, will inevitably lead to an increasing number of treatment courses and hence public health costs will continue to rise.

Furthermore there is now increasing evidence to suggest that the persistent, Gram-negative infections of the periodontal tissues, which typify these diseases, may have more serious consequences on the general health of the affected individual. Whilst the extent of the problem remains controversial, periodontal disease is emerging as a significant risk factor for cardiovascular disease and in the case of pregnant women for an increased risk of giving birth to a premature low birth weight baby.

Periodontal diseases are endemic in all populations and are a major under-served medical market. In the US, 40% of the adult population suffer at least a mild form of the disease and total expenditure on periodontal and preventative procedures in 1999 in the US were $14.3 billion.

There are a number of stages in the progression of periodontitis at which methods of disease control can be applied. Current treatments e.g. antisepsis or surgical treatment have shortfalls in efficacy. Effective dental plaque control can prevent and control gingivitis and periodontitis. Mechanical plaque control, i.e. tooth brushing, is the first line of defence but is generally of variable quality, depending on individual, societal and cultural factors.

Chemical control of dental plaque includes the use of anti-microbial agents, such as triclosan, chlorhexidine and sodium hypochlorite, which are available for self-administration through a variety of vehicles, most commonly mouthwash preparations. This method of plaque control requires regular user compliance, is relatively costly and has limited accessibility subgingivally and interproximally.

Antibiotic therapy of periodontitis includes the use of metronidazole, clindamycin and ciprofloxacin. The widespread use of such compounds in the prevention of gum disease is unlikely due to potential problems with strain resistance, adverse host reaction and secondary infection.

Other recent developments in the therapy of bacterially mediated oral diseases include the use of an antibody that binds specifically to *S. mutans*, a major cause of tooth decay. This antibody is intended for regular topical preventative administration by dentists and patients. Pre-clinical animal studies have demonstrated an antibacterial effect and decay prevention.

A variety of immuno-modulatory strategies have been devised and applied to control oral bacteria. These include passive immunisation using a humanised sIgA antibody originally derived from a mouse IgG monoclonal antibody (1) (6) (27), immunisation of primates with a key antigen of the target organism (11) (21) (24) (51), the use of peptides corresponding to key functional domains of the target antigen (22) (31) (50), delivery of the antigen of the target organism as a recombinant protein expressed in an oral commensal bacterium (42). Hence there is significant state of the art in this area and application of these methodologies could also be applied to the generation of an immune response to the RagB antigen.

At present there are no vaccines or products, either marketed or in development, which are targeted at all *P. gingivalis* strains for the prevention of periodontitis.

Current treatment of periodontal diseases is, in the US at least, largely a hi-tech, private market. There is therefore a need for a vaccine that is cheaper, easily administered (through a range of commercial products such as toothpastes and mouthwash) and accessible to a much wider global population. It is also important that any vaccine treatment is effective against all common strains of the pathogen.

The present invention provides a solution to these problems in the form of an effective vaccine comprising all the major RagB forms of *P. gingivalis*, which would prevent periodontal disease by stopping infection by this organism and from infection caused by different *P. gingivalis* strains.

According to a first aspect of the invention, there is provided a vaccine composition constituted from nucleic acid molecules having a sequence of nucleotides 1-1518 of QMLragB SEQ.ID.NO:5, nucleotides 1-1506 of ThairagB SEQ.ID.NO:6, nucleotides 1-1506 of W50ragB SEQ.ID.NO:7, and nucleotides 1-1518 381ragB SEQ.ID.NO:8 or a fragment thereof.

The nucleic acid molecule may have a sequence of a combination of the nucleic acid sequences of nucleotides 1-1518 of SEQ.ID.NO:5 (QMLragB), nucleotides 1-1506 of SEQ.ID.NO:6 (ThairagB), nucleotides 1-1506 of SEQ.ID.NO:7 (W50ragB) and nucleotides 1-1518 SEQ.ID.NO:8 (381ragB). For example, the nucleic acid sequence may have a sequence of the nucleic acid sequences of SEQ.ID.NO:5 and SEQ.ID.NO:6, or the nucleic acid sequences of SEQ.ID.NO:5, SEQ.ID.NO:6, SEQ.ID.NO:7 and SEQ.ID.NO:8, or a fragment thereof.

Vaccine compositions according to the present invention may be formulated and adapted for any convenient route of administration, such as oral, inhalation, intravenous injection, or intramuscular injection routes.

The vaccines may comprise additional pharmaceutically acceptable excipients or diluents as required.

To be effective, a vaccine must induce long-standing immunity that acts at the appropriate body sites and against the appropriate microbial antigens to prevent disease in all persons at risk; to be practical, it must also be safe, inexpensive, and easy to store and administer.

Some useful vaccines may comprise live, naturally occurring microbes that share important antigens with a pathogen but are not pathogenic themselves; other vaccines are prepared from potentially pathogenic bacteria or viruses that have either been killed or are attenuated; certain vaccines are made of purified macromolecules, for example proteins or glycoproteins; and other strategies for immunization rely on the use of DNA, RNA, etc.

A preferred vaccine of the present invention may be based on a vaccine delivery system for oral colonization and immune response to *P. gingivalis* using live bacteria suitable for this purpose. The possible candidate vectors are *Bacillus subtilis* spores (8) (18), *Streptococcus gordonii*(44) (41) and *Bordetella bronchiseptica* (48).

The vaccines of the present invention may also contain adjuvant substances to assist where necessary if the vaccine is composed of purified antigen. Any suitable pharmaceutically acceptable adjuvant may be used as appropriate, for example, aluminium salts, fragments of bacterial cell wall (e.g. Freund's adjuvant), killed bacteria, bacterial polysaccharides, bacterial heat shock proteins, bacterial DNA, or saponin based adjuvant molecules. Alternatively, or additionally, one or more cytokines may be co-administered as an adjuvant.

Where the vaccine is based on an isolated nucleic acid sequence, for example a DNA sequence, the nucleic acid may be coated onto minute metal projectiles that can be administered by a ballistic gun technique to penetrate the skin and to permit entry into the muscle beneath. Alternatively, the nucleic acid may be administered in a liposome, and/or in the form of a vector. Such vectors may also encode other factors such as GM-CSF.

The nucleic acid sequences of SEQ.ID.NO:5, SEQ.ID.NO:6, SEO.ID.NO:7 and SEO.ID.NO:8 show the ragB DNA sequences of *P. gingivalis*. The rag locus of *P. gingivalis* consists of ragB (encoding an immuno-dominant 55 kDa protein) and a co-transcribed upstream gene, ragA (encoding an 115 kDa outer membrane protein). RagB contains a feature of lipoprotein signal sequence motif and is an important outer membrane protein of *P. gingivalis*.

Fragments of such sequences may be selected according to their DNA sequence homologues, or the entire sequence may be utilised. Generally, any 18 base-pair fragments will be suitable for generating a 6 amino acid sequence.

One aspect of this invention is therefore to provide a vaccine, which contains all possible RagB antigens (an outer membrane protein of *P. gingivalis*), which enables the preparation of a host defence for all kind of *P. gingivalis*, encountered. Such a vaccine composition would be composed of antigenic sequences from all four known pathogenic *P. gingivalis* strains, W50, QMUL, Thai and 381 as described herein.

In a preferred embodiment of the invention, the vaccine composition, the recombinant polypeptides comprising a a nucleic acid molecule selected from the group consisting of nucleotides of SEQ.ID.NO:5, SEQ.ID.NO:6, SEQ.ID.NO:7 and SEQ.ID.NO:8in any suitable combination and/or orientation, or a fragment of such a nucleic acid molecule.

References to nucleic acid according to the present invention include DNA (genomic DNA as well as cDNA, or antisense DNA) as well as RNA unless the context implies otherwise.

The nucleic acid sequences of the present invention also include sequences that are homologous or complementary to those referred to above. The percent identity of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences, which results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul in 1990 (19), modified as in Karlin and Altschul in 1993 (20). The NBLAST and XBLAST programs of Altschul et al (4) have incorporated such an algorithm. BLAST nucleotide searches can be performed with the NBLAST program, score=100, word length=12 to obtain nucleotide sequences homologous to a nucleic acid molecules of the invention. To obtain gapped alignments for comparison purposes, Gapped BLAST can be utilised as described in Altschul et al (5). Alternatively, PSI-Blast can be used to perform an iterated search, which detects distant relationships between molecules (Id.). When utilising BLAST, Gapped BLAST, and PSI-Blast programs, the default parameters of the respective programs (e.g., NBLAST) can be used. See www.ncbi.nlm.nih.gov.

Another example of a mathematical algorithm utilised for the comparison of sequences is the algorithm of Myers and Miller (32). The ALIGN program (version 2.0) which is part of the GCG sequence alignment software package has incorporated such an algorithm. Other algorithms for sequence analysis known in the art include ADVANCE and ADAM as described in Torellis and Robotti (52); and FASTA described in Pearson and Lipman (38). Within FASTA, ktup is a control option that sets the sensitivity and speed of the search.

A nucleic acid sequence which is complementary to a nucleic acid sequence of the present invention is a sequence which hybridises to such a sequence under stringent conditions, or a nucleic acid sequence which is homologous to or would hybridise under stringent conditions to such a sequence but for the degeneracy of the genetic code, or an oligonucleotide sequence specific for any such sequence. The nucleic acid sequences include oligonucleotides composed of nucleotides and also those composed of peptide nucleic acids. Where the nucleic sequence is based on a fragment of the sequences of the invention, the fragment may be at least any ten consecutive nucleotides from the gene, or for example an oligonucleotide composed of from 20, 30, 40, or 50 nucleotides.

Stringent conditions of hybridisation may be characterised by low salt concentrations or high temperature conditions. For example, highly stringent conditions can be defined as being hybridisation to DNA bound to a solid support in 0.5M NaHPO$_4$, 7% sodium dodecyl sulfate (SDS), 1 mM EDTA at 65° C., and washing in 0.1×SSC/0.1% SDS at 68° C. (Ausubel et al eds. "*Current Protocols in Molecular Biology*" 1, page 2.10.3, published by Green Publishing Associates, Inc. and John Wiley & Sons, Inc., New York, (1989)). In some circumstances less stringent conditions may be required. As used in the present application, moderately stringent conditions can be defined as comprising washing in 0.2×SSC/0.1% SDS at 42° C. (Ausubel et al (1989) supra). Hybridisation can also be made more stringent by the addition of increasing amounts of formamide to destabilise the hybrid nucleic acid duplex. Thus particular hybridisation conditions can readily be manipulated, and will generally be selected according to the desired results. In general, convenient hybridisation temperatures in the presence of 50% formamide are 42° C. for a probe, which is 95 to 100% homologous to the target DNA, 37° C. for 90 to 95% homology, and 32° C. for 70 to 90% homology.

Examples of preferred nucleic acid sequences for use in according to the various aspects of the present invention are the sequences of the invention are disclosed herein. In particular, the sequences of SEQ.ID.NO:5 and SEQ.ID.NO:6,or a combination of the sequences of SEQ.ID.NO:5, SEQ.ID.NO:6, SEQ.ID.NO:7 and SEQ.ID.NO:8 or fragments thereof. Complementary or homologous sequences may be 75%, 80%, 85%, 90%, 95%, 99% similar to such sequences.

The peptide sequence may be as described above but it also extends to peptides and polypeptides that are substantially homologous thereto. The term "polypeptide" includes both peptide and protein, unless the context specifies otherwise.

Such peptides include analogues, homologues, orthologues, isoforms, derivatives, fusion proteins and proteins with a similar structure or are a related polypeptide as herein defined.

The term "analogue" as used herein refers to a peptide that possesses a similar or identical function as a peptide coded for by a nucleic acid sequence of the invention but need not necessarily comprise an amino acid sequence that is similar or identical to an amino acid sequence of the invention, or possess a structure that is similar or identical to that of a peptide of the invention. As used herein, an amino acid sequence of a peptide is "similar" to that of a peptide of the invention if it satisfies at least one of the following criteria: (a) the peptide has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of a peptide of the present invention; (b) the peptide is encoded by a nucleotide sequence that hybridises under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of a peptide sequence of the invention; or (c) the peptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding a peptide of the invention.

As used herein, a peptide with "similar structure" to that of a peptide of the invention refers to a peptide that has a similar secondary, tertiary or quaternary structure as that of a peptide of the invention. The structure of a peptide can determined by methods known to those skilled in the art, including but not limited to, X-ray crystallography, nuclear magnetic resonance, and crystallographic electron microscopy.

The term "fusion protein" as used herein refers to a peptide that comprises (i) an amino acid sequence of a peptide of the invention, a fragment thereof, a related peptide or a fragment thereof and (ii) an amino acid sequence of a heterologous peptide (i.e., not a peptide sequence of the present invention).

The term "homologue" as used herein refers to a peptide that comprises an amino acid sequence similar to that of a protein of the invention but does not necessarily possess a similar or identical function.

The term "orthologue" as used herein refers to a peptide that (i) comprises an amino acid sequence similar to that of a protein of the invention and (ii) possesses a similar or identical function.

The term "related peptide" as used herein refers to a homologue, an analogue, an isoform of, an orthologue, or any combination thereof of a peptide of the invention.

The term "derivative" as used herein refers to a peptide that comprises an amino acid sequence of a peptide of the invention, which has been altered by the introduction of amino acid residue substitutions, deletions or additions. The derivative peptide possesses a similar or identical function as peptides of the invention.

The term "fragment" as used herein with respect to a peptide refers to an amino acid sequence of at least 5 or 6 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues) of the amino acid sequence of a peptide of the invention. Fragments of nucleic acid sequences may be defined correspondingly.

The term "isoform" as used herein refers to variants of a peptide that are encoded by the same gene, but that differ in their isoelectric point (pI) or molecular weight (MW), or both. Such isoforms can differ in their amino acid composition (e.g. as a result of alternative splicing or limited proteolysis) and in addition, or in the alternative, may arise from differential post-translational modification (e.g., glycosylation, acylation, phosphorylation). As used herein, the term "isoform" also refers to a protein that peptide exists in only a single form, i.e., it is not expressed as several variants.

The skilled person is aware that various amino acids have similar properties. One or more such amino acids of a substance can often be substituted by one or more other such amino acids without eliminating a desired activity of that substance. Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence of a peptide sequence of the invention. Thus, for example, amino acids which do not have a substantial effect on the biological activity or immunogenicity of such peptides, or at least which do not eliminate such activity, may be deleted. Amino acid insertions relative to the sequence of peptides of the invention can also be made. This may be done to alter the properties of a peptide of the present invention (e.g. to assist in identification, purification or expression. Such amino acid changes relative to the sequence of a polypeptide of the invention from a recombinant source can be made using any suitable technique e.g. by using site-directed mutagenesis.

A nucleic acid construct according to the invention may suitably be inserted into a vector, which is an expression vector that contains nucleic acid sequences as defined above. The term "vector" or "expression vector" generally refers to any nucleic acid vector, which may be RNA, DNA or cDNA.

The term "expression vector" may include, among others, chromosomal, episomal, and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host may be used for expression in this regard. The vector may be constructed from a bacterial plasmid, for example the bacterial plasmid pUC18.

Recombinant expression vectors will include, for example, origins of replication, a promoter preferably derived from a highly expressed gene to direct transcription of a structural sequence as defined above, and a selectable marker to permit isolation of vector containing cells after exposure to the vector.

Expression vectors may comprise an origin of replication, a suitable promoter as defined herein and/or enhancers, and also any necessary ribosome binding sites, polyadenylation regions, splice donor and acceptor sites, transcriptional termination sequences, and 5'-flanking non-transcribed sequences that are necessary for expression. Preferred expression vectors according to the present invention may be devoid of enhancer elements. The expression vectors may also include selectable markers, such as antibiotic resistance, which enable the vectors to be propagated.

Introduction of an expression vector into the host cell can be effected by calcium phosphate transfection, DEAE-dextran mediated transfection, microinjection, cationic lipid-mediated transfection, electroporation, transduction, scrape loading, ballistic introduction, infection of other methods. Such methods are described in many standard laboratory manuals, such as Sambrook et al., Molecular Cloning: A Laboratory Manual, $2^{nd}$ Ed., Cold Spring Harbor Laboratory Press, Cold Spring Harbor, N.Y. (1989).

In certain embodiments of the invention, the vectors may provide for specific expression. Such specific expression may be inducible expression or expression only in certain types of cells or both inducible and cell-specific. Preferred among inducible vectors are vectors that can be induced for expression by environmental factors that are easy to manipulate, such as temperature, nutrient additives, hypoxia and/or the presence of cytokines or other biologically active factors. Particularly preferred among inducible vectors are vectors that can be induced for expression by changes in the levels of chemicals, for example, chemical additives such as antibiotics. A variety of vectors suitable for use in the invention, including constitutive and inducible expression vectors for use in prokaryotic and eukaryotic hosts, are well known and employed routinely by those skilled in the art.

The promoter sequence may be any suitable known promoter, for example the human cytomegalovirus (CMV) promoter, the CMV immediate early promoter, the HSV thymidine kinase promoter, the early and late SV40 promoters or the promoters of retroviral LTR's, such as those of the Rous sarcoma virus ("RSV"), and metallothionein promoters, such as the mouse metallothionein-I promoter. The promoter may comprise the minimum sequence required for promoter activity (such as a TATA box without enhancer elements), for example, the minimal sequence of the CMV promoter (mCMV). Preferably the promoter is a mammalian promoter that can function at a low basal level devoid of an enhancer element.

The DNA comprising the nucleic acid sequence of the invention may be single or double stranded. Single stranded DNA may be the coding or sense strand, or it may be the non-coding or anti-sense strand. For therapeutic use, the nucleic acid sequences are in a form capable of being expressed in the subject to be treated.

The termination sequences in the vector may be a sequence of adenylate nucleotides, which encode a polyadenylation signal. Typically, the polyadenylation signal is recognisable in the subject to be treated, such as, for example, the corresponding sequences from viruses such as, for human treatment, and the SV40 virus. Other termination signals are well known in the art and may be used.

Preferably, the polyadenylation signal is a bi-directional terminator of RNA transcription. The termination signal may be the polyadenylation signal of the simian 40 virus (SV40), for example the SV40 late poly(A). Alternatively, the termination sequence may be the polyadenylation signal of bovine growth hormone which results in maximal expression when combined with a CMV promoter (54).

According to a second aspect of the invention, there is provided a vaccine composition comprising a polypeptide encoded by a nucleic acid molecule having a nucleic acid sequence of SEQ.ID.NO:5, SEQ.ID.NO:6, SEQ.ID.NO:7 or SEQ.ID.NO:8or a fragment thereof.

Fragments of such sequences may be selected according to their antigenic determinants, or the entire sequence may be utilised. Generally, 6 amino acid sequences that form an epitope will be suitable.

According to a third aspect of the invention, there is provided an antibody composition, the composition comprising at least one antibody raised against the recombinant polypeptide composition as first aspect of the invention, wherein the antibody specifically binds a polypeptide having a sequence selected from the group consisting of residues 1-505 of SEQ.ID.NO:9 (QMLRagB), residues 1-501 of SEQ.ID.NO:10 (ThaiRagB), 501 of SEQ.ID.NO:11 (W50RagB) and residues 1-505 of SEQ.ID.NO:12 (381RagB).

According to a fourth aspect of the invention, there is provided a polypeptide having a sequence selected from the group consisting of residues 1-505 of SEQ.ID.NO:9(QMLRagB), residues 1-501 of SEQ.ID.NO:10 (ThaiRagB), 501 of SEQ.ID.NO:11(W50RagB) and residues 1-505 of SEQ.ID.NO:12 (381RagB) for use in medicine.

Uses in accordance with these aspects of the invention that are directed to treatment or prevention of disease caused by P. gingivalis, therefore also extend to methods of treatment for such conditions or diseases, the methods comprising the administration to a subject a vaccine composition of the invention as described above.

As part of such methods, it may be convenient to determine which strain of P. gingivalis is the infectious agent in order to be able to specifically select a vaccine directed against the correct allele of RagB. Whilst all 4 variant strains can be targeted, it is more effective and cheaper to target the actual infectious agent present in a patient by means of a pre-treatment diagnostic step.

According to an eighth aspect of the invention, there is provided an oral healthcare composition, which comprises a vaccine in accordance with other aspects of the invention described above.

Such oral healthcare compositions may be, but are not limited to pastes (e.g. toothpastes), mouthwashes, gum (e.g. a confectionery based chewing gum, preferably sugar-free).

Vaccine compositions may also be used to coat oral healthcare implements or instruments, e.g. dental floss or tape, etc.

The present invention therefore also includes such antibodies for use in medicine, and the use of the antibodies in the preparation of a medicament for the treatment or prevention of periodontitis, or of infection of a subject by P. gingivalis. Methods of treatment as described above therefore also include the administration of such antibodies as part of a method of immunotherapy for the treatment or prevention of such diseases.

The nucleic acid sequences of the present invention may also be used to screen samples for the presence of P. gingivalis. Accordingly, the present invention additionally provides kits for the detection of P. gingivalis in a sample in which the kit comprises specifically designed primers for use in a DNA amplification procedure, such as the Polymerase Chain Reaction (PCR). Suitably, such kits are provided with instructions for use in the detection of the presence of P. gingivalis in a sample, or a method for the diagnosis of such an infection in a subject. Alternatively, the antibodies of the present invention can be used as the basis of a kit for the detection of P. gingivalis in a sample from a patient. Detection of the antigen can be accomplished by any suitable means for the detection of antigen-antibody binding, such as ELISA, radio-immunoassay, etc.

The vaccine compositions of the present invention also provide the basis for novel and effective combination therapies to treat or prevent periodontitis or infection of a subject by P. gingivitis. Such methods of treatment may comprise the separates sequential or simultaneous administration to a subject of a vaccine composition of the invention and another pharmaceutical substance, such as an antibiotic or an antimicrobial agent.

Suitable antibiotics may include, but are not limited to, metronidazole, clindamycin, or ciprofloxacin. Suitable, antimicrobial agents may include, but are not limited to, triclosan, chlorhexidine or sodium hypochlorite.

Preferred features for the second and subsequent aspects of the invention are as for the first aspect mutatis mutandis.

The present invention will now be described by way of further example with reference to the following Examples and drawings, which are included for the purposes of illustration only and are not to be taken as being limiting on the invention.

Brief description of drawings is listed below:

FIG. 1 shows the nucleic acid sequence of SEQ.ID.NO:1 for ragB allele QML (ragB3).

FIG. 2 shows the nucleic acid sequence of SEQ.ID.NO:2 for ragB allele Thai (ragB2).

FIG. 3 shows the nucleic acid sequence of SEQ.ID.NO:3 for ragB allele W50(ragB1).

FIG. 4 shows the nucleic acid sequence of SEQ.ID.NO:1 for ragB allele 381(ragB4).

FIG. 5 shows the nucleic acid sequence alignments for ragB alleles SEQ.ID.NO:5 to SEQ.ID.NO:8.

FIG. 6 shows the amino acid sequence alignments for RagB alleles SEQ.ID.NO:9 to SEQ.ID.NO:12.

Primers designed for the rag locus: Forward (orf2 6586-6606), SEQ.ID.NO:15, 5'-CAAAGTCCTGCCACGAGTAGC-3 '; Reverse (orfV 388-408), SEQ.ID.NO:16, 5'-CGTTTCTCGCCACTTTCGTC-3'.

Figure 8:
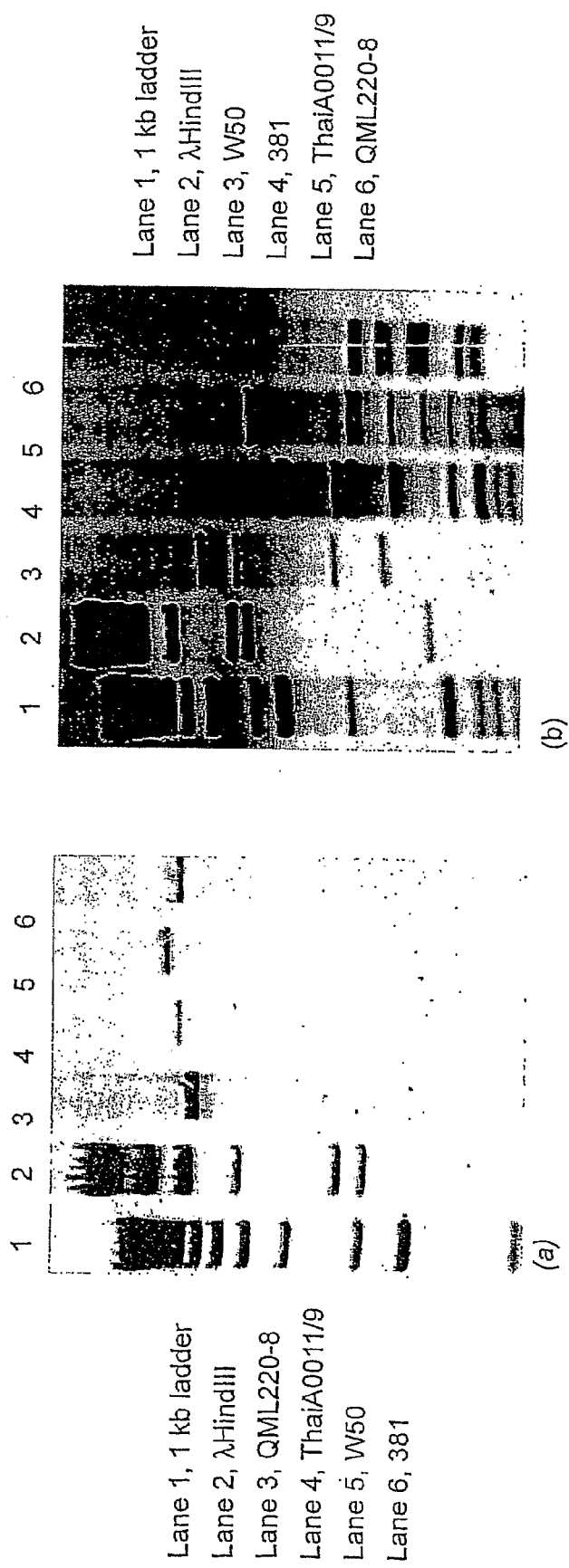

FIG. 8 shows the results of PCR amplification of rag locus and digestion with HaeIII. FIG. 8(a) shows the rag locus size different; FIG. 8(b) shows the restriction map patterns are different.

Figure 9:
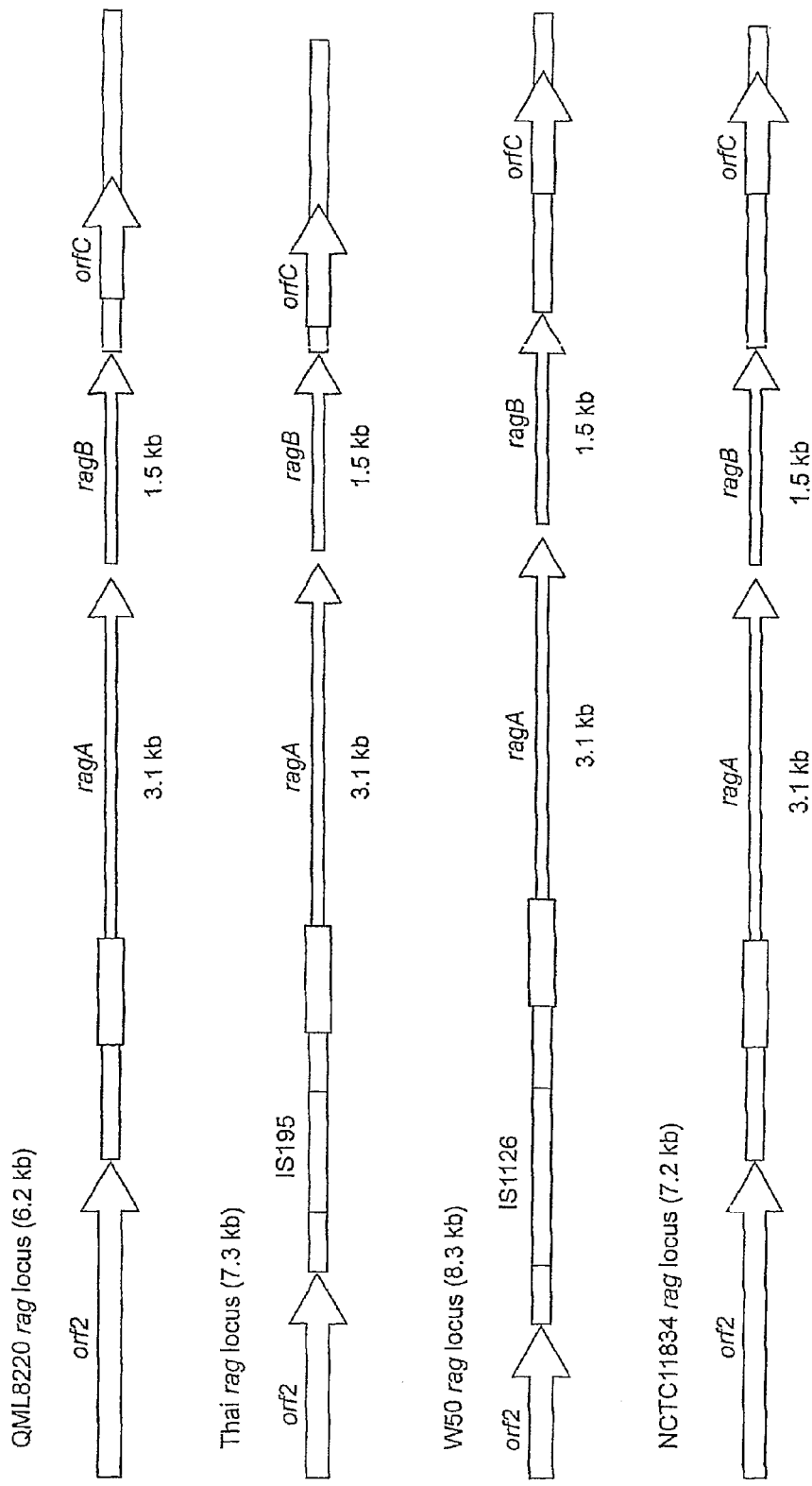

FIG. 9 shows the results of a sequence comparison of rag locus from the four main groups found in patient samples.

Figure 10:
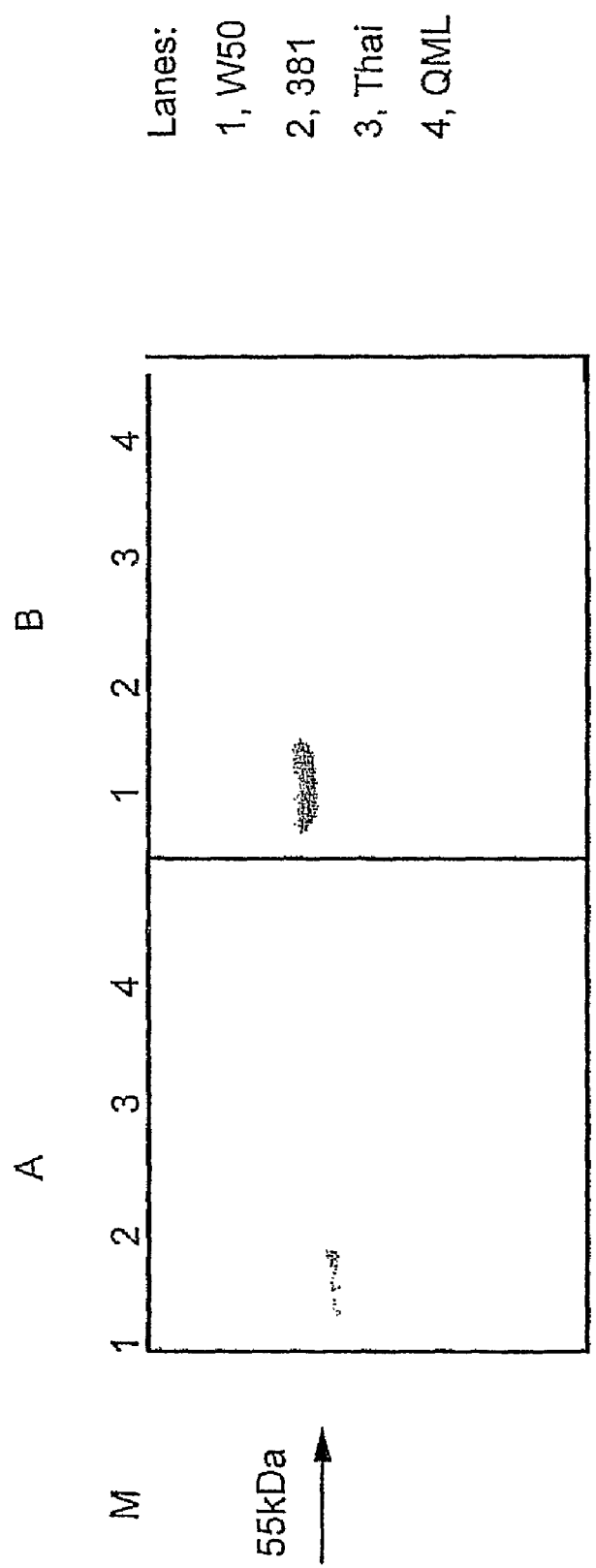

FIG. 10 shows the results of a Western blot assay conducted on cell lysates from four strains of different ragB alleles react with anti-P. gingivalis W50 RagB antibodies. "A" shows blot with monoclonal antibody against recombinant W50 RagB (1B15/31). "B" shows blots with polyclonal antibody against recombinant W50 RagB (02NH); No cross-reactions observed among four groups of RagB.

Figure 11:
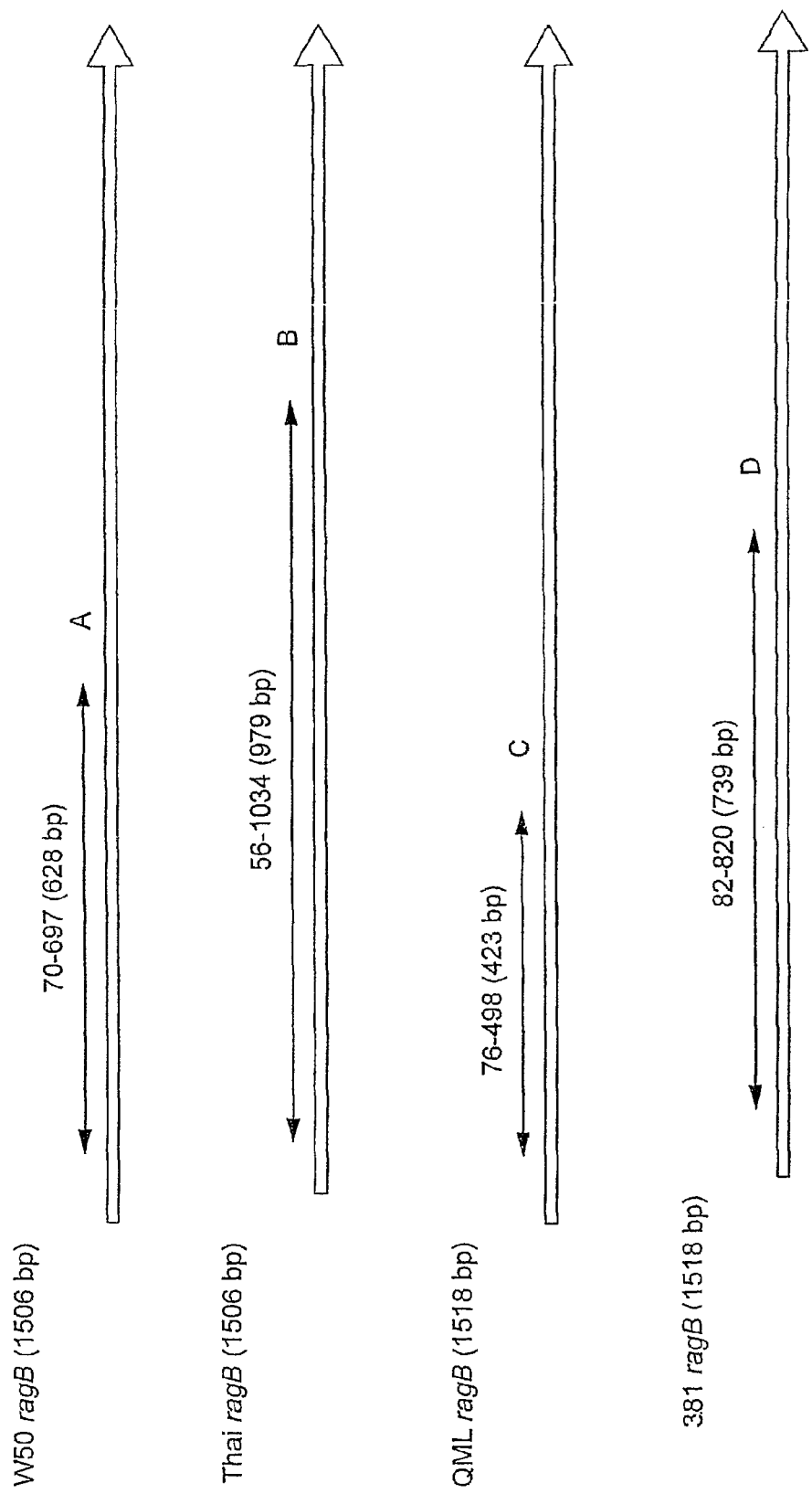

FIG. 11 shows in diagrammatic form of the four different ragB alleles with primer design (specific primers were designed for each group).

Figure 12:
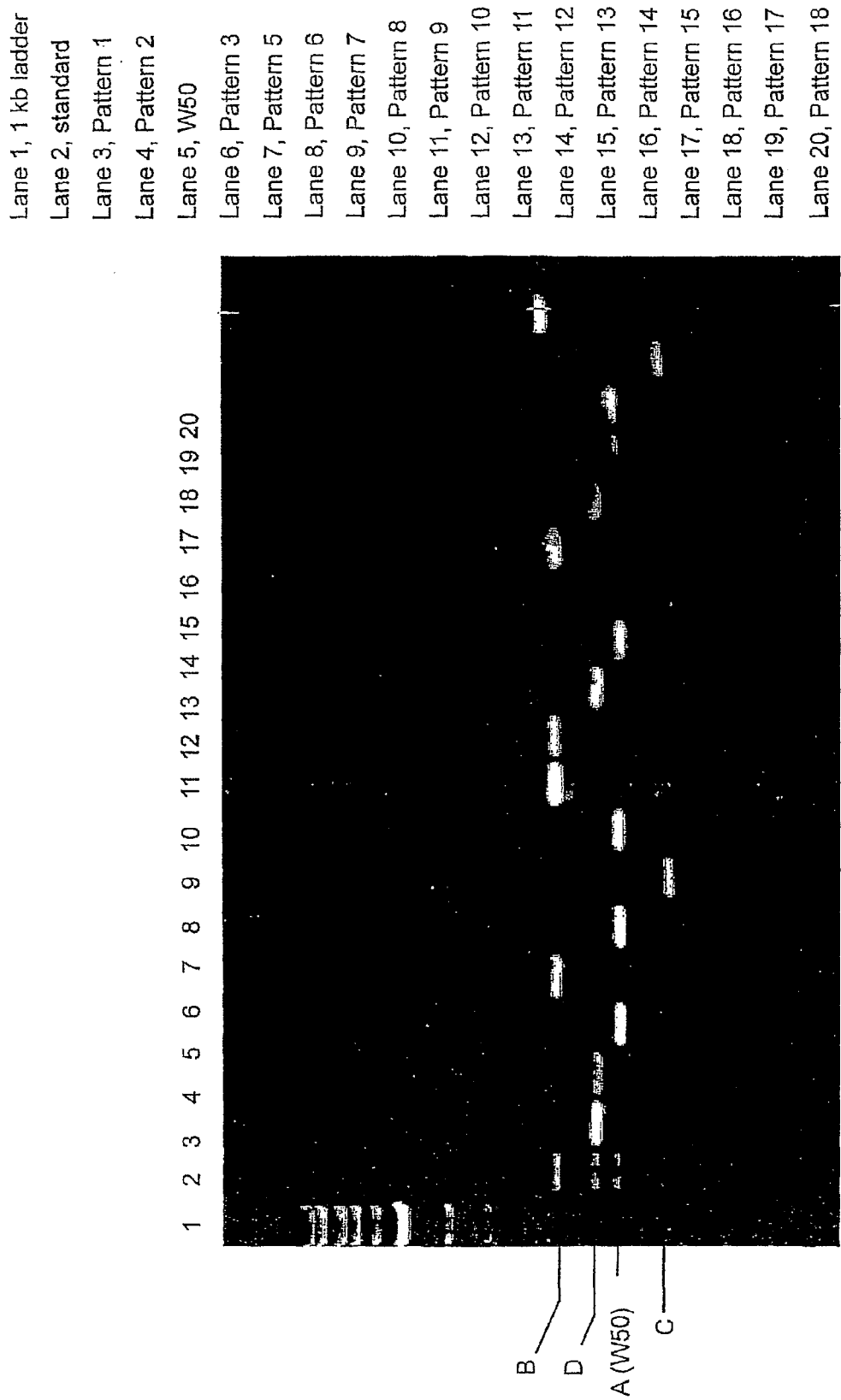

FIG. 12 shows the results of multiplex-PCR detection of ragB alleles. There is only one specific band for individual isolate of P. gingivalis.

Figure 13:
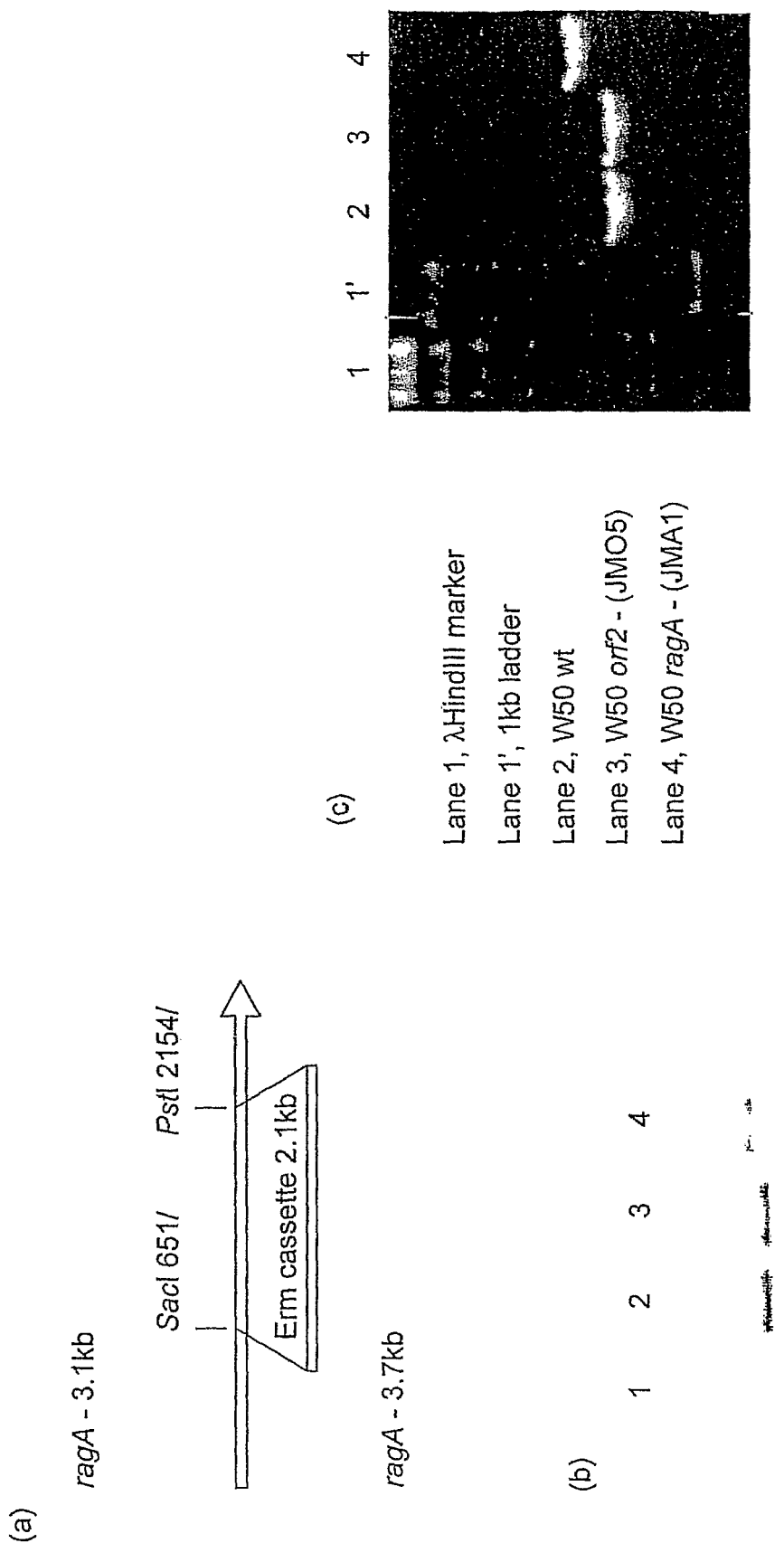

FIG. 13 shows the construction of ragA mutant in P. gingivalis W50 (JMA1) in FIG. 13(a); FIG. 13(b) shows Southern blot, ragA as a probe; FIG. 13(c) shows check ragA mutation using PCR with ragA primers.

Figure 14:
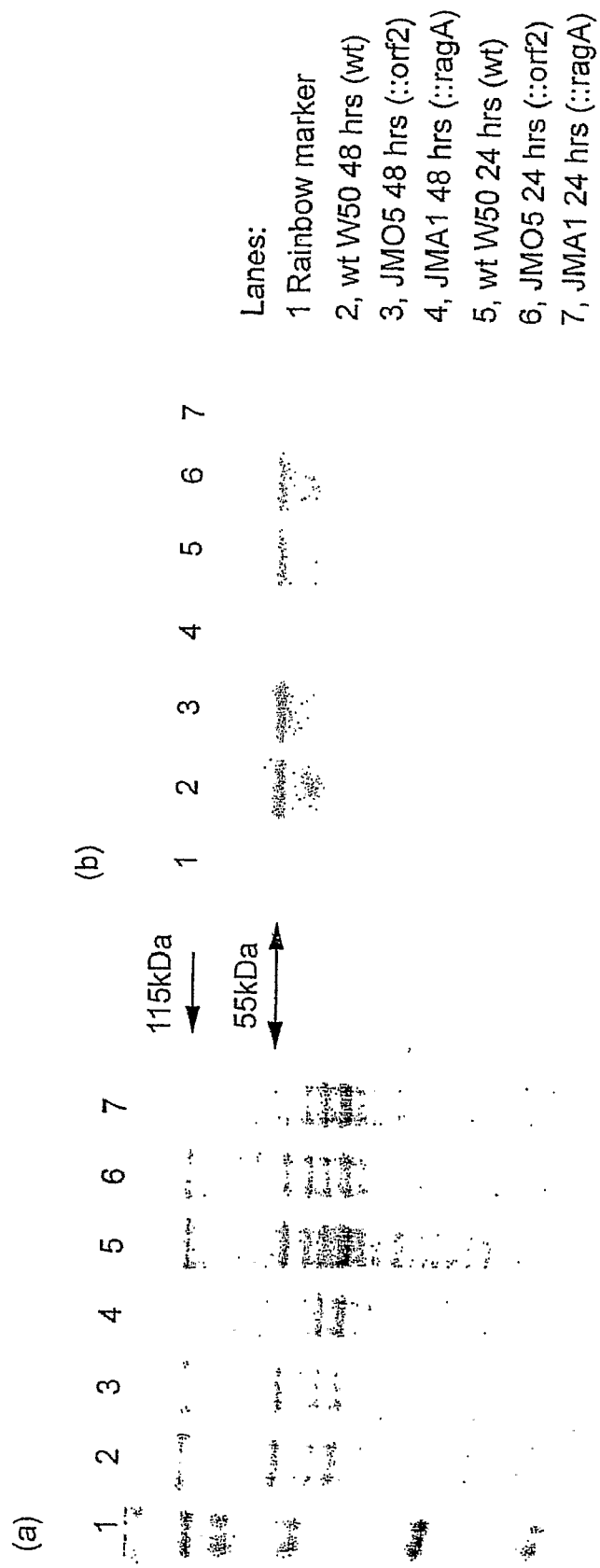

FIG. 14 shows the characterisation of ragA mutant (JMA1) in SDS-PAGE and Western blot. 12.5% SDS-PAGE and Western blot analysis of P. gingivalis W50 and mutant strain cells. FIG. 14(a) shows stain with Coomassie blue (ragA-lost bands at 115 kDa and 55 kDa). FIG. 14(b) shows blots react with anti-RagB antibody (E38). Rag B also absent in ragA-.

Figure 15:
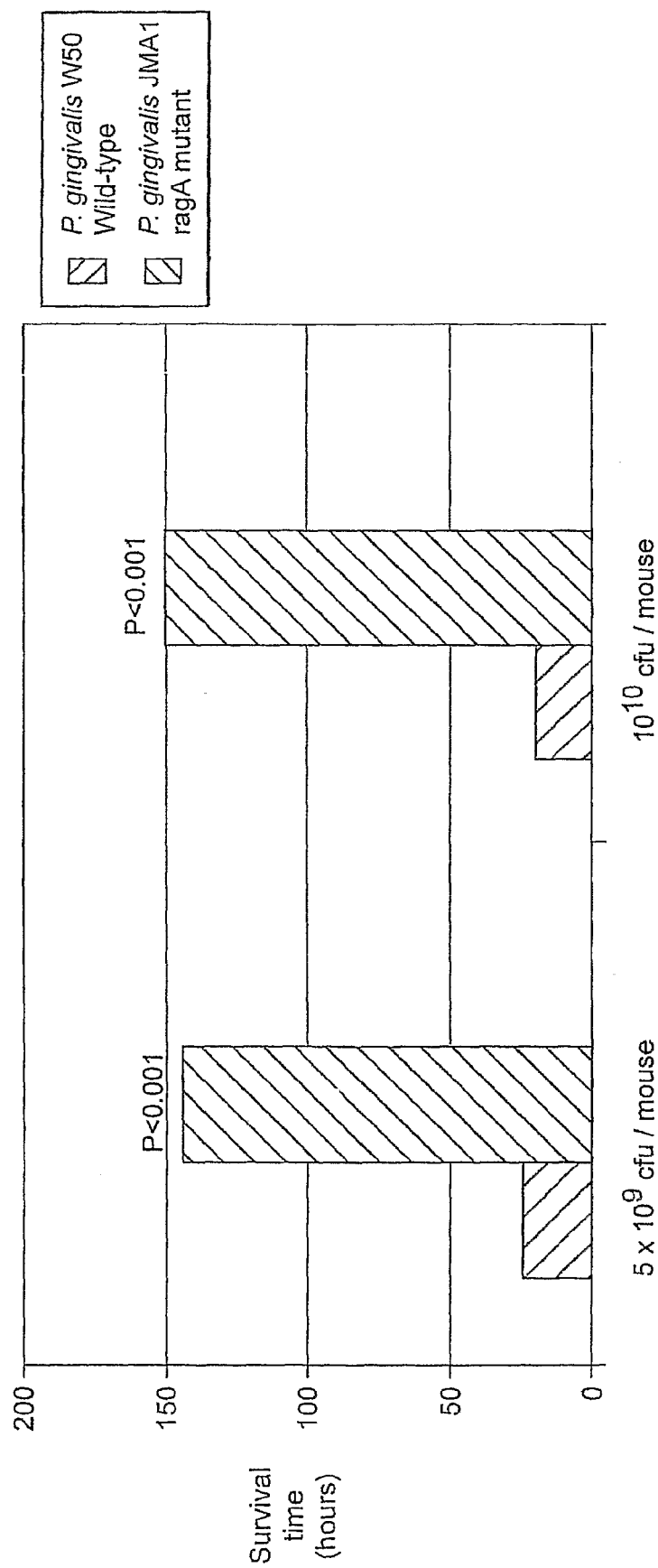

FIG. 15 shows a virulence study of P. gingivalis and ragA mutant in the mouse animal model.

Figure 16:
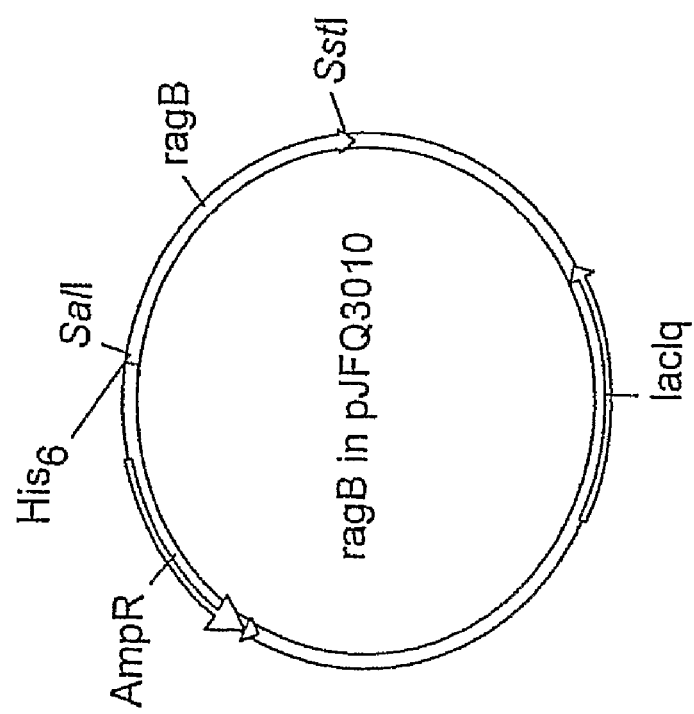

FIG. 16 shows the construction of ragB into expression vector (His6-RagB pNY34). RagB was synthesised with $His_6$ tag, minus the first 23 amino acid putative signal peptide sequence, under the control of tac promoter and IPTG induction in E. coli XL1 Blue. The expected size of the recombinant protein was 55.7 kDa.

Figure 17:
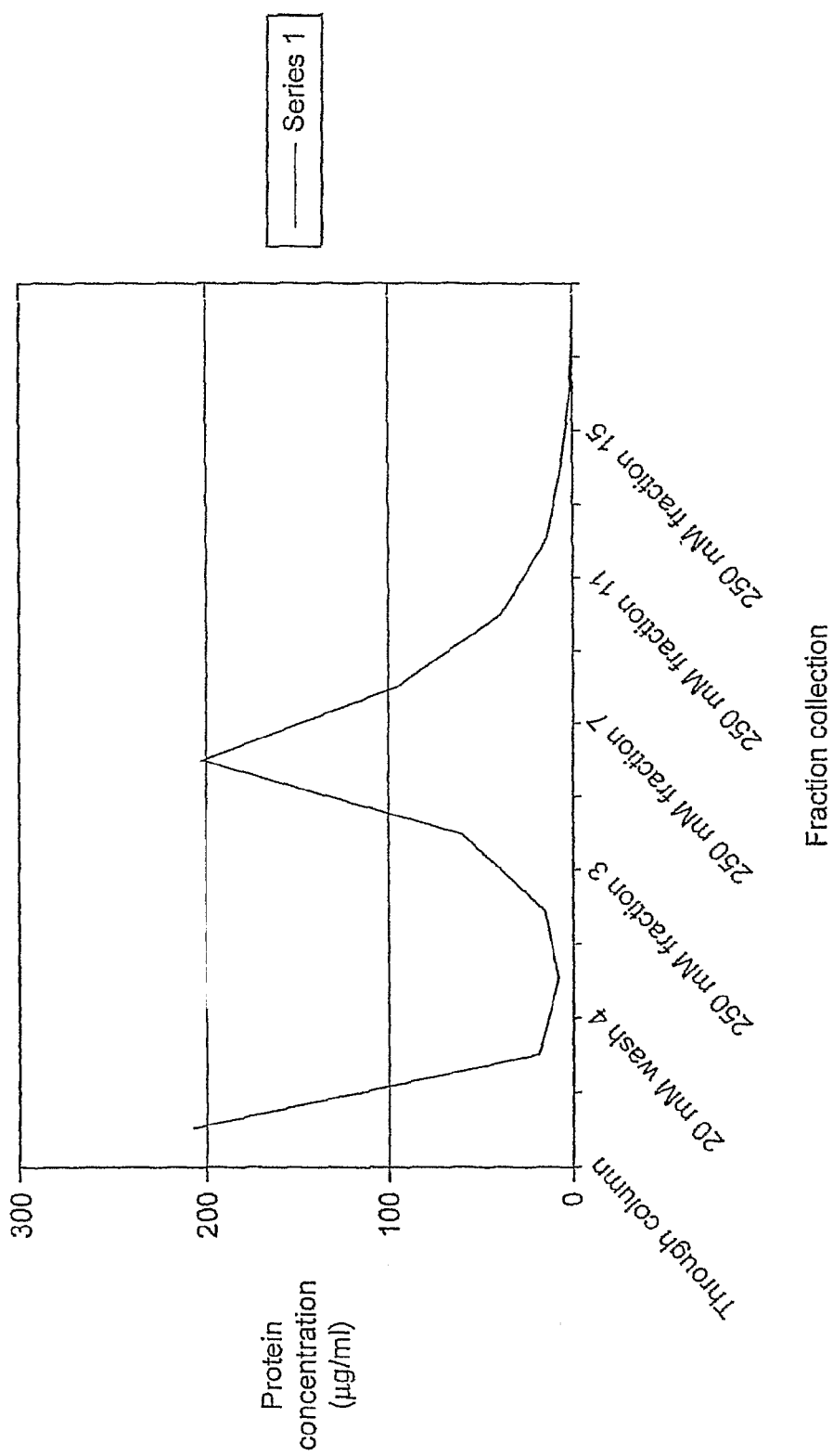

FIG. 17 shows the purification of recombinant RagB of P. gingivalis. Elute recombinant RagB from Ni-NTA column.

Figure 18:
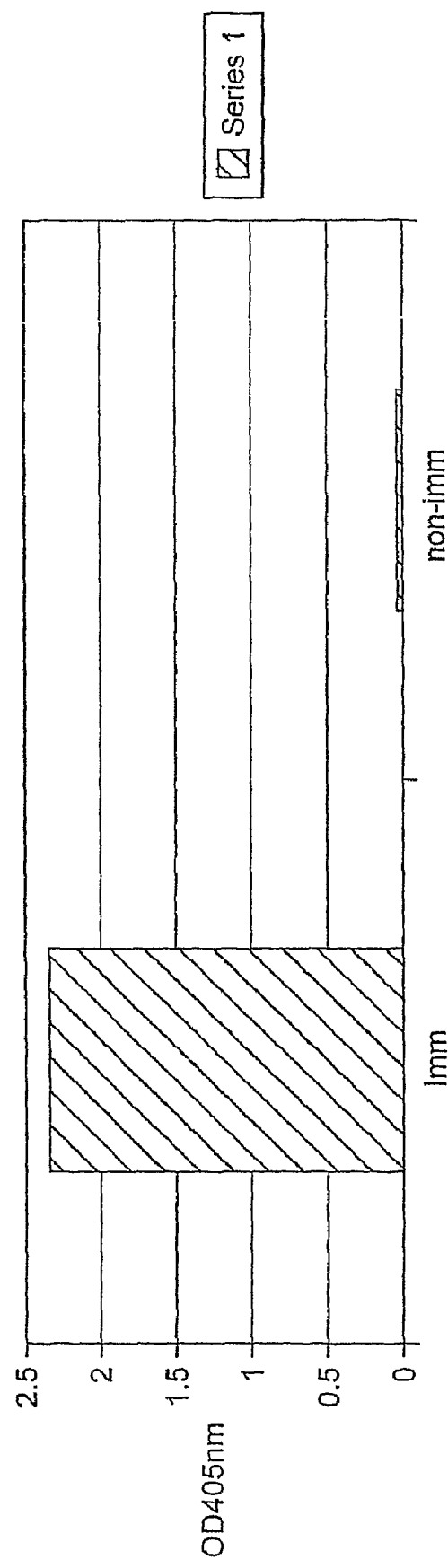

FIG. 18 shows animals' immune response to recombinant RagB. Antibody titre detection by using ELISA (coated with recombinant RagB)—1:12800 dilution. Mice immunized with recombinant RagB W50 and immune response was tested. Specific antibody against recombinant RagB was detected at a very high level.

Figure 19:
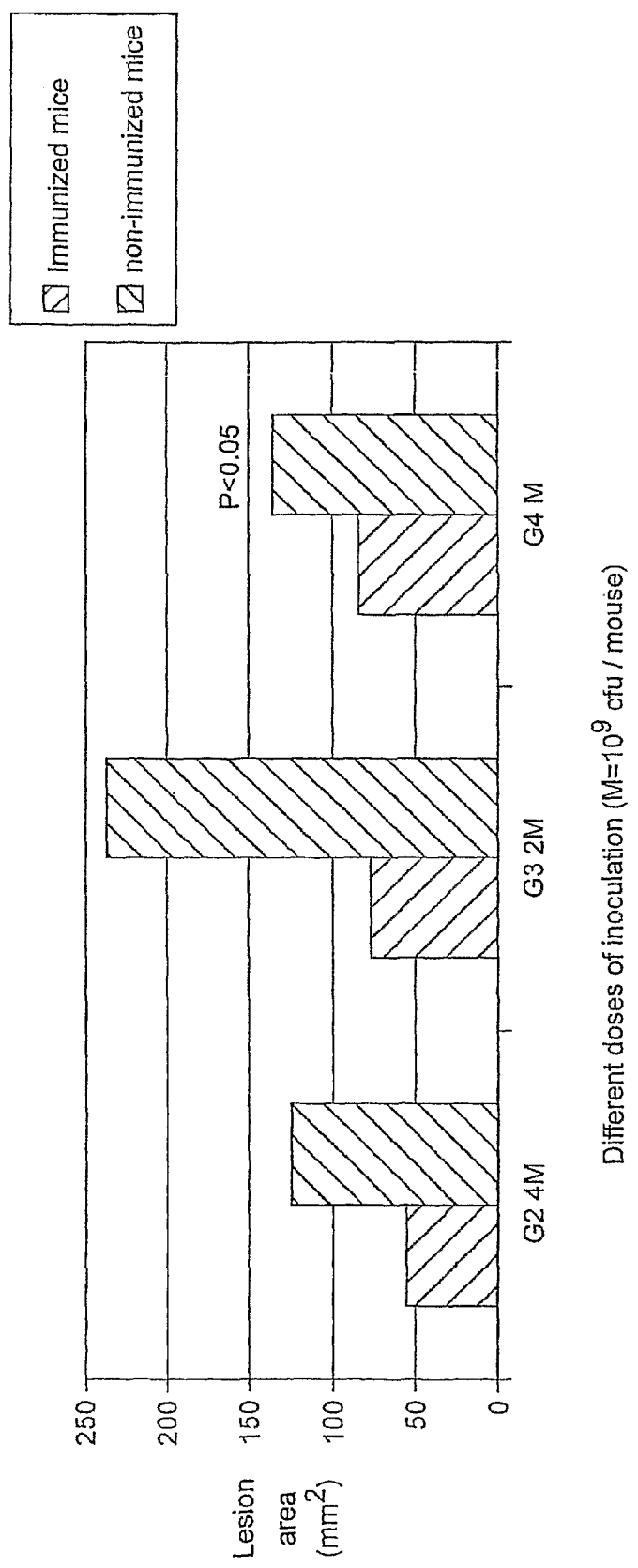

FIG. 19 shows the protection of mice from lesion formation when challenged with P. gingivalis W50.

Figure 20:
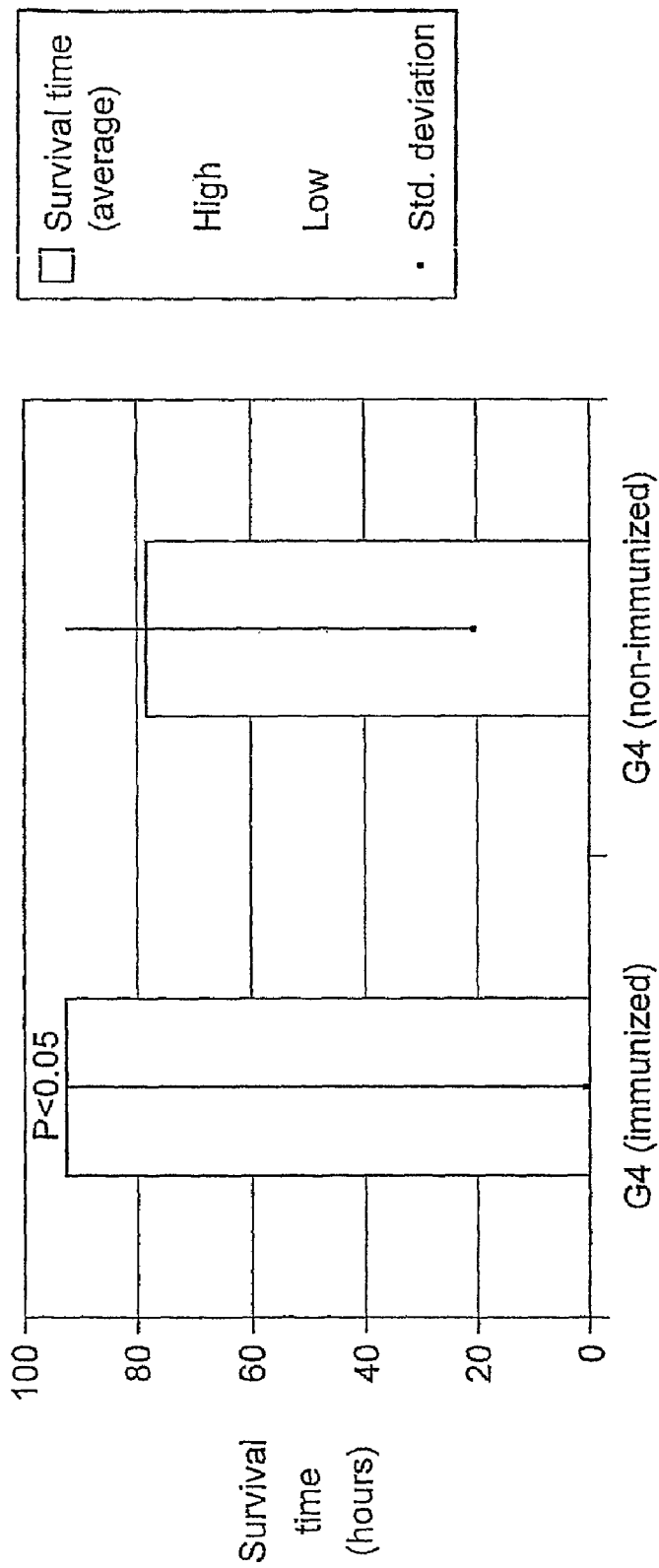

FIG. 20 shows the protection effect of immunisation basis on survival time. Immunized mice showed a longer survival time than non-immunized mice post challenge of P. gingivalis W50 at the dose (M=$10^9$ cfu/mouse).

EXAMPLE 1

Heterogeneity in the Rag Locus of P. gingivalis

Materials and Methods:
Bacterial Strains and Culture Conditions

Isolates were grown on Fastidious Anaerobic Agar (FAA) plates with 5% defibrinated horse blood, or Brain Heart Infusion (BHI) broth with 5 μg ml$^{-1}$ haemin at 37° C. in an anaerobic cabinet (Don Whitley Scientific) with an atmosphere of 80% $N_2$, 10% $H_2$, 10% $CO_2$ A total of 168 isolates of P. gingivalis from the laboratory collection of the inventors were investigated, including isolates generously supplied by numerous colleagues of the inventors. All isolates had been recovered from human sources, mostly from patients with periodontal disease, and were from 15 countries. Isolates were confirmed to be P. gingivalis by PCR with species-specific primers to 16S rRNA genes.

DNA Manipulations

Total genomic DNA was isolated from stationary phase bacteria using a Puregene DNA isolation kit reagent (Flowgen) under manufacturer's instructions. Briefly, 1 ml of overnight BHI cultures was lysed with 600 μl cell lysis solution at 80° C. for 5 minutes. Cells were treated with 3 μl RNaseA solution at 37° C. for 1 hour. Protein was removed by precipitation with guanidine thiocyanate and the DNA was precipitated and cleaned with successive washes of 100% isopropanol and 70% ethanol. Purified DNA was resuspended in 50 μl TE (10 mM Tris, 1 mM EDTA, pH 8.0).

DNA purification to remove primers, enzymes and other reagents was undertaken using a Qiagen Gel Extraction Kit. Briefly, DNA was bound to a silicon based ion exchange matrix under high salt conditions in buffer PB. The DNA was cleaned with two washes of buffer PE and eluted in 50 μl TE.

Restriction digestion of PCR products was performed using Amersham Pharmacia or New England Biolabs enzymes and buffers. Reactions were incubated at 37° C. for at least 2 hours. DNA electrophoresis was performed in 0.8% agarose with Tris-Borate-EDTA (0.09M Tris-borate, 0.002M EDTA). Ethidium bromide stained gels were viewed under UV light and the image captured.

The primers designed to be specific to P. gingivalis:

```
16s rRNA,
SEQ.ID.NO: 13,
Forward primer:
5'- AGG CAG CTT GCC ATA CTG CG -3'

SEQ.ID.NO: 14,
Reverse primer:
5'- ACT GTT AGC AAC TAC CGA TGT -3'
```

```
rag locus,
SEQ.ID.NO: 15,
Forward primer:
5'- CAAAGTCCTGCCACGAGTAGC -3'

SEQ.ID.NO: 16,
Reverse primer:
5'-CGTTTTCTCGCCACTTTCGTC-3' rag1 (W50),
SEQ.ID.NO: 17,
Forward primer:
5'-CGC GAC CCC GAA GGA AAA GAT T-3'

SEQ.ID.NO: 18,
Reverse primer:
5'-CAC GGC TCA CAT AAA GAA CGC T-3' rag2 (Thai),
SEQ.ID.NO: 19,
Forward primer:
5'-GCT TTG CCG CTT GTG ACT TGG-3'

SEQ.ID.NO: 20,
Reverse primer:
5'-CCA CCG TCA CCG TTC ACC TTG-3' rag3 (QML),
SEQ.ID.NO: 21,
Forward primer:
5'-CCG GAA GAT AAG GCC AAG AAA GA-3'

SEQ.ID.NO: 22,
Reverse primer:
5'-ACG CCA ATT CGC CAA AGC T-3' rag4 (381),
SEQ.ID.NO: 23,
Forward primer:
5'-CCG GAT GGA AGT GAT GAA CAG A-3'

SEQ.ID.NO: 24,
Reverse primer:
5'-CGC GGT AAA CCT CAG CAA ATT-3'
```

Polymerase Chain Reaction (PCR)

All amplification reactions were performed in a PCR thermal cycler. Standard PCR reactions used 50 μl volumes with 0.5μg each primer and 0.5 μl chromosomal DNA template in a PCR buffer with 1.5 mM $MgCl_2$. Amplification of longer products was performed Standard programs for PCR comprised 25 cycles of denaturation 1 minute at 95° C., annealing 1 minute at 50° C., and extension 1-3 minutes at 72° C. For long PCR, 10 cycles with annealing at 52° C. and an extension time of 6 minutes 40 sec at 68° C. were followed by 15 cycles with annealing at 60° C. and 7 minutes extension at 68° C.

SDS-PAGE and Western Blotting

SDS-PAGE was performed according to the method of Laemmli on 12% separating gels. Briefly, samples were prepared from 1.5 ml original culture volumes. Cell pellets were resuspended in 135 μl of 0.2% SDS and whirly mixed; protease inhibitor leupeptin was added to a final concentration of 100 μg/ml and incubated at room temperature for 10 minutes. The inactivated sample was then diluted 1:1 in working strength sample buffer (2×SDS) and heated at 100° C. for 5 minutes. Samples (10 μl equivalent to 50 μl of the original culture) were loaded 10 μl per lane. Western blotting was carried out in a bicarbonate transfer buffer (3 mM $Na_2CO_3$, 10 mM $NaHCO_3$, pH 9.9, 20% [vol/vol] methanol) at a constant current of 400 mA for 1 hour using nitrocellulose membranes. After blotting, the membranes were blocked in 5% bovine serum albumin and incubated overnight in B15 and O2NH anti-recombinant RagB antibodies. Antibody binding was detected by using HRP-conjugated anti-mouse and anti-rabbit immunoglobulins (Dako, Germany).

DNA Sequence Determination and Nucleotide Sequence Accession Numbers

Long PCR products from Thai (A011/9), QML (QM220), and 381 (strain obtained as ATCC33277$^T$) were purified and sent to MWG-Biotech for sequence determination, using their publication grade sequencing service. Open reading frames were identified with FramePlot 2.3.2 online software. The nucleotide sequence data reported in this study have been assigned GenBank accession numbers AY842852 (381), AY842853 (QML) and AY842854 (That).

Figure 7:
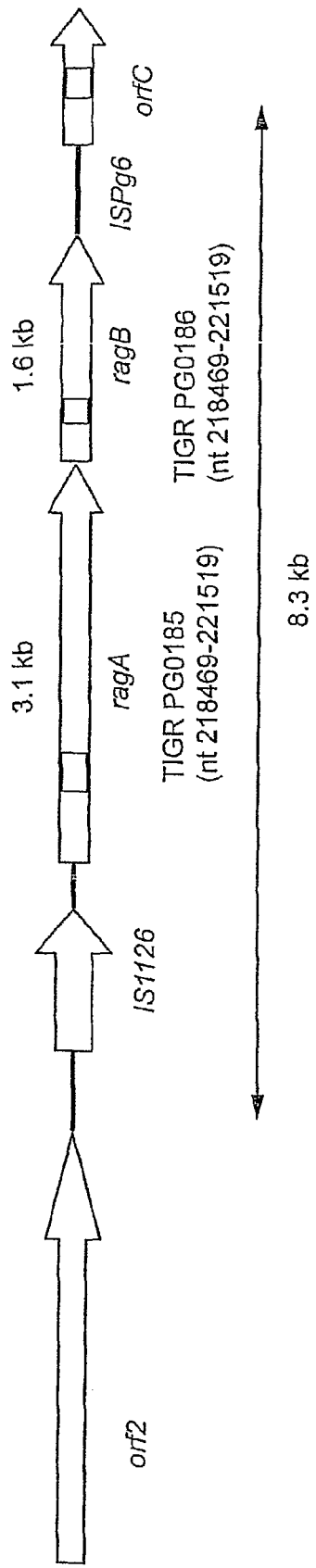
FIG. 7 shows the rag locus in P. gingivalis W83 in diagrammatical form with primer details.

Summary: Following analysis of the restriction enzyme map pattern of rag locus (see FIGS. 7 and 9), it was found that ragB apparently appeared in four main groups and these four-ragB gene alleles from different groups were sequenced (see FIGS. 1-4). There is a high DNA variation between them, their similarity around about 60% as well as protein sequence (see FIGS. 5-6 and 8). The specific primers were designed for each group. A multiple-PCR method was employed to identify ragB alleles from P. gingivalis collections. Local clinical samples and isolates of P. gingivalis from a worldwide collection were tested to obtain information of P. gingivalis in clinical population for ragB in different strains of P. gingivalis. The results showed that majority (97%) of clinical samples contained just a single PCR product specific for one of the four groups (see FIGS. 11-12). Furthermore, the results from western blot indicated that antibodies against P. gingivalis W50 RagB do not cross-react with other RagB groups (see FIG. 10). These findings confirmed that ragB gene is divided into four major sequence and antigenic groups.

EXAMPLE 2

The Role of the Rag Locus of P. gingivalis W50 in Virulence

Materials and Methods:
Bacterial Strains, Plasmid, and Culture Conditions

P. gingivalis W50 were used as standard reference strain in this study. Culture conditions for P. gingivalis have been described in the example 1. Plasmid pVA2198, which carries a copy of ermF-ermAM (erm) cassette, has been described previously and was used to provide Clindamycin resistant marker for mutagenesis. Clindamycin was used at 5 µg/ml.
PCR and DNA Manipulations Primers designed to amplify ragA from P. gingivalis W50 genomic DNA were: forward primer, SEQ.ID.NO:25, 5'-CGCTATTCTTCCTTTGCTTGCT-3', reverse primer, SEQ.ID.NO:26, 5'-TTACCATCCGCATCGACTTGA-3'. PCR amplification was performed with Techne's thermal Cycler in reaction mixtures (50 µl) containing 60 µM of each primer, 50 ng of template DNA, and 45 µl of PCR master mix (Abgene, Surrey, UK). The PCR consisted of 25 cycles with a temperature profile of 1 minute at 95° C., 1 minute at 50° C., and 3 minutes at 72° C., followed by 1 cycle of 7 minutes at 72° C. The amplified DNAs were analysed in 0.7% agarose-TBE gel. The specific PCR products of 3.0-kb ragA were digested with SacI and PstI consecutively; prospective DNA fragments were purified and ligated with erm cassette (SacI/PstI) cut from plasmid DNA pVA2198 (7). The primers used for amplification of ragA gene were employed to amplify the ligations to ensure that a reconstructed product, ragA::erm, was in the mixture. This methodology led to the construct with a deletion of 1.5 kb in ragA replaced with a 2.1 kb erm; the interrupted gene is now 600 bp bigger than the original ragA (see FIG. 13).

Construction of Allelic-Exchange Mutant

The amplicons (from above) were used to generate P. gingivalis JMA1 (ragA::erm). The constructs were transformed into competent cells of P. gingivalis W50 by electroporation. Briefly, 1 ml of an actively growing culture of P. gingivalis was used to inoculate 10 ml of BHI broth supplemented with hemin and menadione, and then was incubated overnight at 37° C. The overnight culture was then inoculated into 30 ml of fresh pre-warmed BHI at 1:10 dilution and then grown for 6 hr. The culture of P. gingivalis was harvested by centrifugation at 10,000 (g) for 10 min at 4° C. and washed in 30 ml of electroporation buffer (EPB; 10% glycerol, 1 mM $MgCl_2$; filter sterilized; stored at 4° C.), and the pellet was suspended in 600 µl EPB. Approximately 200 ng of DNA was added to 200 µl cells in a 0.2 cm-path length cuvette. The cells were pulsed with a Bio-Rad Gene Pulser at 2.5 kV for the potential difference, 200Ω for the resistance and 25 µF for the capacitance. P. gingivalis cells were then immediately diluted in 1 ml BHI-haemin broth (at room temperature) and allowed to recover for 16 hr in the anaerobic cabinet. After overnight recovery, initial selection of mutants was performed on blood agar plates containing Clindamycin (5 µg/ml) and incubated anaerobically at 37° C. for 7 to 10 days. Following allelic exchange mutagenesis, mutants in each category were characterized by phenotypic analysis.
SDS-PAGE and Western Blotting Preparation of extracts described in example 1. Samples electrophoresis on 10% polyacrylamide gels, and the gel was stained with Coomassie blue (see FIG. 14). Detection of the 55 kDa outer membrane antigen RagB with monoclonal antibody E38 was performed (see FIG. 14).
Southern Blotting Genomic DNAs were digested with the appropriate restriction endonucleases and electrophoresed in agarose gels, and then transferred onto Hybond N+ membranes. The membranes were prehybridized for 1 hour at 65° C. in a hybridisation buffer and hybridised overnight in the same solution with dig-labelled probes. The probe DNA for ragA was prepared by PCR, and that for erm was prepared by EcoRI and SphI restriction digestion of plasmid pVA2198. The probes were labelled by the random-primer method with digoxigenin-dUTP following the manufacturer's instructions. Detection of hybrids was performed by enzyme immunoassay.
Murine Virulence Model Protocols The virulence potentials of P. gingivalis W50 and JMA1 (ragA::erm) were examined by using the murine lesion model. Briefly, bacterial cells from an 18-hour culture in BHI medium (containing 5 µg/ml of hemin) were harvested by centrifugation and resuspended to a final density in the culture medium at the required concentration for inoculation into the mice. Groups of BALB/c mice (8 per group) were inoculated subcutaneously twice with 100 µl portions of bacterial cell suspensions on the mid point of each flank towards the dorsal surface. Three bacterial doses were employed at $1\times10^{11}$, $5\times10^{10}$ and $2.5\times10^{10}$ cfu/ml in each group. The animals were then monitored twice daily for 8 days for the development of lesions and to assess their general condition according to a standardized appearance and behaviour scoring system which was approved by the local ethics committee and the United Kingdom Home Office animal experimentation licensing authority.

Summary: To investigate the role of the rag locus of P. gingivalis W50 in virulence, an isogenic ragA mutant with expresses neither RagA nor RagB was constructed following PCR, insertion of an Erm cassette in vitro, and electro transformation with the construct. The mutant, JMA1, was confirmed by PCR, Southern hybridisation, SDS-PAGE, and Western blotting (see FIGS. 13-14). JMA1 was used in a murine model for virulence investigation. Groups of mice (8 mice/group) were subcutaneously inoculated with $5 \times 10^9$-$2 \times 10^{10}$ cfu of *P. gingivalis*/mouse and their size, weight, behaviour and appearance over 8 days were monitored. Results showed that inactivation of ragA lead to a significant reduction (P<0.001) in the virulence of *P. gingivalis* W50 at $5 \times 10^9$ and $10^{10}$ cfu/mouse on the basis of time of survival (see FIG. 15). These data suggest that the rag locus of *P. gingivalis* W50 plays an important role in the virulence of this strain.

EXAMPLE 3

Cloning and Expression of RagB of *P. gingivalis* in *E. coli*

Materials and Methods:
Bacteria and Growth Conditions

Culture conditions for *P. gingivalis* described in example 1. *Escherichia coli* XL-1 Blue (Stratagene) were grown in Luria-Bertani medium.
Primers Primers designed to amplify the ragB of *P. gingivalis* W50 were:

```
SEQ.ID.NO: 27,
RagBF1:
5'-ATATATGAGCTCCGCGACCCCGAAGGAAAAG-3'

SEQ.ID.NO: 28,
RagBR1:
5'-TATATAGTCGACGAAAAGATAGGGGCTGCGAC-3'
``` the italicized sequences represent SacI and SalI sites, respectively, were designed to generate the cloning sites.
PCR PCR were performed for 25 cycles, and the parameters were: denaturation, 94° C., 1 min; annealing, 60° C., 1 min; extension, 72° C., 4 min.
Clone RagB into Fusion Protein Expression Vector The 1,508-bp partial SstI-SalI amplicon was subsequently cloned into the corresponding sites in pJFQ3010, a derivative of pQE30 (7), to generate NY34 as a (His)6-tagged recombinant protein.

The recombinant plasmid was then propagated in *Escherichia coli* XL-1 Blue with selection for ampicillin resistance. This scheme ensured that RagB, minus the first 23-amino-acid putative signal peptide sequence, was synthesized as an N-terminal His6 fusion protein under the control of the tac promoter and IPTG (isopropyl-β-D-thioga-lactopyranoside) induction in *E. coli* XL-1 Blue. The predicted size of the recombinant protein was 55.7 kDa (see FIG. 16).
Purification of Recombinant Proteins

*E. coli* XL-1 Blue was transformed with the appropriate expression construct and grown overnight at 37° C. in Luria-Bertani medium incorporating ampicillin at 50 µg/ml. Cells were harvested by centrifugation and solubilized in 0.01 M imidazole lysis buffer (Phosphate buffer, 8M Urea or 6M Guanidine HCl pH8). Supernatant from the lysate was incubated for 1 hour at room temperature with Ni-nitrilotriacetic acid agarose (Qiagen) and packed into a column, which was first washed with lysis buffer containing 0.02 M imidazole pH6.3 and eluted with 0.25 M imidazole in lysis buffer pH5.9 (see FIG. 17). The eluted protein was dialyzed against 0.15 M saline, filter sterilized. The identities of the recombinant proteins were confirmed by SDS-PAGE and Coomassie blue stain. The concentration of the recombinant protein was examined. The recombinant proteins were then stored at minus 20° C.

Summary: ragB has been successfully cloned from genomic DNA of *P. gingivalis* W50 and *P. gingivalis* Thai strains (data not shown) according sequence data.

The ragBs were constructed into pQE expression vectors and the recombinants were expressed in *E. coli* XL-1 Blue. To purify recombinant RagB, Ni-NTA metal-affinity chromatography column was employed. It was found that the use of poly-His fusion expression system can make an efficient amount of protein for immunisation in an animal model.

EXAMPLE 4

Host Immune Response Following Immunization with *P. gingivalis* W50 RagB

Materials and Methods:
Preparation of Immunogens

The adjuvant used for this study was Aluminum Hydroxide. Fresh made $Al(OH)_3$ was mixed with recombinant RagB. Briefly, 10 ml of 10% potassium alum (aluminum potassium sulfate, $AlK(SO4)_2.12H_2O$) in a 50-ml conical tube, vortex and add 22.8 ml of 0.25N NaOH dropwise; centrifuge at 1000 g for 10 minutes after incubation at room temperature for 10 minutes; wash the pellet with distilled water. 1 mg of $Al(OH)_3$ can bind approximately 50-200 µg of protein antigen. The adjuvant and the recombinant RagB were incubated in 0.9% saline at room temperature for 20 minutes. Spin at 10,000 g for 10 minutes. Test the supernatant for the presence of the antigen to calculate the amount of antigen bound to the adjuvant.
Immunisation 5-week-old BALB/c mice purchased from an approved supplier and allowed 1-week acclimatisation. Animals were inoculated subcutaneously with ~25 µg protein (RagB)/adjuvant in 100 µl. A booster injection was given 4 weeks later with the same amount and volume of immunogen-emulsified adjuvant. Four weeks later blood samples were taken to assay for antibodies.
Collection of Sera and Determination of Antibody Titre 15-50 µl of blood sample was taken from mice. Incubate the blood samples for 60 minutes at 37° C. to allow complete coagulation and clot reaction. Centrifuge blood samples at 10,000 g for 10 minutes to separate sera from blood cells after overnight incubation at 4° C. The sera were stored frozen (−20° C.). ELISA and Western blot were employed to detect the antibodies against recombinant RagB and native RagB. If the titre is not satisfactory at this step, another boost injection may be required.

Summary: The immune response of mice immunized with recombinant RagB of *P. gingivalis* W50 was examined and it was found that all immunised animals produced a high antibody titre against the recombinant protein itself and the native protein of RagB from this organism (see FIG. 18).

EXAMPLE 5

Investigation of Protection Offered Following Challenge

Materials and Methods,
Animals:

48 BALB/c mice immunised with recombinant RagB were split into six groups. Each group had same number of non-immunization mice as age-control.

Challenge Experiment

The murine lesion model used for virulence study has been described in example 2. Briefly, bacterial cells from an 18-h culture in BHI medium (containing 5 µg/ml of hemin) were harvested by centrifugation and resuspended to a final density in the culture medium at the required concentration. Groups of BALB/c mice (8 per group) both immunised and non-immunised were inoculated subcutaneously twice with 100 µl portions of bacterial cell suspensions on the mid point of each flank towards the dorsal surface. Five bacterial doses of *P. gingivalis* W50 were inoculated at $4 \times 10^{11}$, $2 \times 10^{11}$, $10^{10}$, $5 \times 10^9$ and $2.5 \times 10^9$ cfu/ml; $10^{10}$) cfu/ml of *P. gingivalis* Thai. The animals were then monitored twice daily for 8 days for the development of lesions and to assess their general condition according to a standardized appearance and behaviour scoring system.

Summary: The protective effect of immunisation with recombinant RagB was evaluated in the same animal model described above. The results showed that immunisation protected animals from subcutaneous challenge with the homologous strain based on lesion size and survival time (see FIGS. 19-20). The cross reactivity was tested of sera from animals immunised with recombinant RagB from *P. gingivalis* W50 with other *P. gingivalis* strains carrying one of the three alternative rag alleles. No cross-reaction was observed between *P. gingivalis* W50 and *P. gingivalis* Thai on the basis of Western blotting (see FIG. 10). Hence, it is considered unlikely that there will be any cross-protection in mice immunised with RagB from W50 and challenged with *P. gingivalis* carrying alternative RagB alleles. This was confirmed in preliminary experiments, which showed that immunisation with recombinant RagB from *P. gingivalis* W50 (ragB1 group) did not protect animals challenged with *P. gingivalis* Thai strain (ragB2 group). The data therefore indicates that RagB is a promising vaccine candidate.

EXAMPLE 6

Mixture of Recombinant Proteins

1. Based on the outcome of the protection experiments, a recombinant protein mixture will be used as the immunogen in the immunisation/challenge experiment. The whole procedure will be similar to the experiments described before but a mixture of proteins in a 1:1:1:1 ratio will instead of single allelic recombinant protein.
2. 96 mice in 12 groups will be immunized with the emulsion mixture and boosted as described above.
3. One week after final boost, both immunized and non-immunized mice will be subcutaneously inoculated with $5 \times 10^9$-$2 \times 10^{10}$ cfu of *P. gingivalis* from the four major allelic type of ragB per mouse and their lesion size, weight, behaviour and appearance over 8 days will be monitored.

EXAMPLE 7

Engineering Recombinant *Streptococcus gordonii* Expressing *P. gingivalis* RagB Domains 1. Design specific primers with suitable restriction enzyme cut site at both ends for ragB in each group. PCR will be employed to amplify ragB from different groups.
2. Clone ragB into insertion vector pSMB55 to obtain translational gene fusions. The resulting chimeric plasmid will be used to transform *S. gordonii*. The transformants will be selected on plates containing erythromycin.
3. The recombinant colonies will be then confirmed by PCR and Southern blot hybridisation. The expression of RagB will be tested on SDS-PAGE followed by immunoblotting analysis. The positive colonies can be freezing dried or stored at −70° C.
4. Experimental animals (mice and/or rabbits) will be used to examine the immunogenicity of RagB from the recombinant *S. gordonii*. The animals will be immunized subcutaneously with $10^9$ live *S. gordonii* cells emulsified in a copolymer adjuvant. The antibodies in the sera of immunized animals will be tested by ELISA and immunoblotting against *P. gingivalis* RagB.
5. To test oral colonization and immune response, Sprague-Dawley germfree rats will be used as a model. The recombinant *S. gordonii* will be administrated into the oral cavity ($10^9$ cfu) two inoculations 24 h apart. To assess *S. gordonii* colonization, oral swabs will be taken at regular weekly intervals. Immune response and prevention will be tested as described above.

EXAMPLE 8

Determine the Potential Protective Effect of Specific Antibodies in a *P. gingivalis* Challenge Model 1. Suspensions of freshly harvested bacterial cells are adjusted to the required cell density (e.g. for *P. gingivalis* W50:$5 \times 10^9$ cfu/ml).
2. Adult mice (6-10 weeks old) are separated into six groups (8 mice/group) and marked so they are individually identifiable.
3. Group 1 as a positive control receive *P. gingivalis*; group 2 for testing prevention effect of passive antibody transfer receive specific antibody 24 hours prior to *P. gingivalis* challenge; group 3 same as group 2 but irrelevant Ig instead of specific antibody for passive antibody transfer negative control; group 4 receive *P. gingivalis* opsonized with specific antibody; group 5 receive *P. gingivalis* opsonized irrelevant Ig for opsonization negative control; group 6 a negative control receive BHI broth only.
4. The prepared cell suspension will be inoculated into groups of mice for challenge experiments. The animals are inoculated subcutaneously with 0.1 ml of bacterial suspension at an appropriate dose at a site midway down each flank.
5. Following challenge, each animal is examined daily for signs of infection and to assess its' general condition.
6. After 15 days, or at the time of killing, localised or spreading lesion size (length and width) is measured with a caliper, the area determined and expressed in square millimeters.

REFERENCES

1. Abiko, Y. 2000. Crit. Rev. Oral Biol. Med. 11:140-158.
2. Albandar, et al 1997. J. Periodontol. 68:973-981.
3. Allaker, et al 1997. Oral Microbiol. Immunol. 12:298-302.
4. Altschul, et al 1990. J. Mol. Biol. 215:403-410.
5. Altschul, et al 1997. Nucleic Acids Res. 25:3389-3402.
6. Booth, V. and T. Lehner. 1997 J. Periodontal Res. 32:54-60.
7. Curtis, et al 1999. Infect. Immun. 67:3816-3823.
8. Duc, et al 2003. Infect. Immun. 71:2810-2818.
9. Dzink, et al 1985. J. Clin. Periodontol. 12:648-659.
10. Dzink, et al 1985. J. Clin. Periodontol. 12:648-659.

11. Fellowes, et al 1988. Eur. J. Immunol. 18:559-564.
12. Gemmell, et al 2001. Oral Microbiol. Immunol. 16:129-135.
13. Gonzalez, et al 2003. Infect. Immun. 71:2283-2287.
14. Griffen, et al 1998. J. Clin. Microbiol. 36:3239-3242.
15. Griffen, et al 1999 37:4028-4033.
16. Haffajee, A. D. and S. S. Socransky. 1994. Periodontol. 2000. 5:78-111.
17. Haffajee, A. D. and S. S. Socransky. 1994. Periodontol 2000. 5:78-111.
18. Isticato, et al 2001 J. Bacteriol. 183:6294-6301.
19. Karlin, S. and S. F. Altschul. 1990. Proc. Natl. Acad. Sci. U.S.A 87:2264-2268.
20. Karlin, S. and S. F. Altschul. 1993. Proc. Natl. Acad. Sci. U.S.A 90:5873-5877.
21. Kelly, et al 1989. FEBS Lett. 258:127-132.
22. Kelly, et al 1999. Nat. Biotechnol. 17:42-47.
23. Kozarov, et al Infect. Immun. 66:4721-4725.
24. Lehner, et al J. Immunol. 143:2699-2705.
25. Loos, et al 1993. Infect. Immun. 61:204-212.
26. Loos, et al Infect. Immun. 61:204-212.
27. Ma, et al 1989. Clin. Exp. Immunol. 77:331-337.
28. Menard, C. and C. Mouton. 1995. Infect. Immun. 63:2522-2531.
29. Michalek, et al 2002. Immunol. Res. 26:223-234.
30. Mikolajczyk-Pawlinska, et al 1998. Biol. Chem. 379:205-211.
31. Munro, et al 1993. Infect. Immun. 61:4590-4598.
32. Myers, E. W. and W. Miller. 1989. Bull. Math. Biol. 51:5-37.
33. Nelson, et al 2003. J. Bacteriol. 185:5591-5601.
34. Oyaizu, et al 2001. Oral Microbiol. Immunol. 16:73-78.
35. Ozmeric, et al 2000. Acta Odontol. Scand. 58:183-187.
36. Paster, et al 2001. J. Bacteriol. 183:3770-3783.
37. Paster, 2001. J. Bacteriol. 183:3770-3783.
38. Pearson, W. R. and D. J. Lipman. 1988. Proc. Natl. Acad. Sci. U.S.A 85:2444-2448.
39. Preus, et al 1995. J. Clin. Periodontol. 22:674-678.
40. Rajapakse, et al 2002. Infect. Immun. 70:2480-2486.
41. Sharma, et al 2001. Infect. Immun. 69:2928-2934.
42. Sharma, et al 2001. Infect. Immun. 69:2928-2934.
43. Sharma, et al 2001. Infect. Immun. 69:2928-2934.
44. Sharma, et al 1997. Biochem. Biophys. Res. Commun. 238:313-316.
45. Slots, et al 1995. Clin. Infect. Dis. 20 Suppl 2:S304-S307.
46. Socransky, et al J. Clin. Periodontol. 25:134-144.
47. Socransky, et al 2002. J. Clin. Periodontol. 29:260-268.
48. Stevenson, A. and M. Roberts. 2003 FEMS Immunol. Med. Microbiol. 37:121-128.
49. Tanner, et al. 1979. J. Clin. Periodontol. 6:278-307.
50. Todryk, et al 1996. Immunology 87:55-63.
51. Todryk, et al 1996. Immunology 87:55-63.
52. Torelli, A. and C. A. Robotti. 1994. Comput. Appl. Biosci. 10:3-5.
53. Tsurumi, et al 2003. J. Oral Sci. 45:111-116.
54. Yew, et al 1997. Hum. Gene Ther. 8:575-584.
55. Yonezawa, et al 2001. Infect. Immun. 69:2858-2864.
56. Zhang, Y. J. 1993. Bull. Tokyo Med. Dent. Univ 40:113-123.

The invention claimed is:

1. An immunogenic composition comprising the nucleic acid molecules of nucleotides 1-1518 of SEQ.ID.NO:5(QMLragB), nucleotides 1-1506 of SEQ.ID.NO:6 (ThairagB) and nucleotides 1-1518 of SEQ.ID.NO:8 (381ragB), wherein the nucleic acid molecules SEQ.ID.NO:5, SEQ.ID.NO:6 and SEQ.ID.NO: 8 encode a polypeptide SEQ.ID.NO: 9, SEQ.ID.NO: 10 and SEQ.ID.NO: 12 respectively.

2. An oral healthcare composition comprising a composition as in claim 1.

3. A kit for the detection of *P. gingivalis* in a sample comprising one or more probes consisting of 19-23 nucleotides from 1-1518 of SEQ.ID.NO:5 (QMLragB), 1-1506 of SEQ.ID.NO:6 (ThairagB)and 1-1518 of SEQ.ID.NO:8 (381ragB).

* * * * *

SEQUENCE LISTING

```
<160> NUMBER OF SEQ ID NOS: 28

<210> SEQ ID NO 1
<211> LENGTH: 6173
<212> TYPE: DNA
<213> ORGANISM: Porphyromonas gingivalis
<220> FEATURE:
<223> OTHER INFORMATION: The following sequence is named QML

<400> SEQUENCE: 1
tcgcgcaacc acaatgaatc cttattatgc caatccttat attctccatc attgatggcc      60
actcgcagtt ttttcgcaga gaaatcagtc acgagcttca tcattacgga atccaaaact     120
gtgccataag gcatatattt cttattaata attgtccctt ttgcatgatc gatagaaaaa     180 aatactttt ccaaatccgg attttctta ctggaaaggt agaaacggtg gatctgcaga      240
tcaaccacat tcacgtcttc gagatctaac ttggactctt tacaagagac cacagctatt     300
cctgagcaaa aagagaagaa agtccaaagg agatatcgga tgaaatgttt cttgcacata     360
cctatgataa tttagtgtac aaagataaga catctgctga cttatactac acttttcat      420 ccatcaaacc atggaggccg tatcaaatcc gggatatatt cgagatgtag tagtgcctga     480
tgatttccat cggcctgttt tcaatttata gtgtcatttc agcgtcagat agaaaaaagg     540
ggccatccgt tggacagccc ctttatttgt ttattgacta aaagtcagca gaaattacca     600
gttcttgatc aaatgaggat taacctgacg atctcggtta gggaactccc atgtaaatgc     660
atagtgaccg gccggaacag gttgctccaa tacgatctca cgagcataac cagtaagagc     720
aggttggatt tctgttttgt cgatattcgg aagattccaa cgaatcatat cgcgcaaacg     780
agcgccctca ccgataagct cacgagtacg ttcttcttga atagctttca ttacatcacc     840
```

```
ggtgtcaata ttgccaccac gagcagcact gagcttttg aggtatgcaa tcgccgtagc    900
atcgtctcct gtcatgtgag cacactcagc taccatcaga taagcttctg caatactgaa    960
catacgtacc cctattttca gaatggggat atcggctgtt tctctgtagg caggatcttc   1020
aaggaatttg ttcaccaaat atcccttttc actgccgtta ctaactgtct tatcaatata   1080
gactgacttg cgataatctg catcttcgta caaatcgact acccactgca agggaacgat   1140
aaacggcgca tatttaatct tcttattcac cacagatgcg ccattaagag aggttgcacc   1200
aacagcaccg gtcgtaggag atgcaaaagc acggaatacg atctcgggat tgttagcatc   1260
tgaacgatag attttagcaa aatcctctgc attgttagcg ttgatcaaag gatacttctc   1320
cacaatctgc ttagcatctg caagtgcatc ggcatagtta cccatagaaa ggtgtacacg   1380
tgctcgcaaa gcatgagcgt agtcacgtcc ggcatatgtg atgccgtcag ggttcttctc   1440
aggcaatacc gtaatagcag cctccaaagc cgagaggatg tgatcataac actccttctg   1500
agtagcacgg gggccgatat aagcgggatt gaattccttg atcaaaacaa tgccaaggtt   1560
ttgaggactt tgattggatg cggcatcata tttatatgca aaacgatcca tcaaacgcca   1620
attcgccaaa gcttgtacaa cacgtacctc tgcgagatat ctcttagcac gttccacttc   1680
ttcggaggaa atgaaaatgc tcatatcagt attattggca agagcttttt ccatatcttc   1740
gatataggag tttgcctgct gaatcagacg gctatactcg aagtaataac cggcaatacc   1800
atatacttga tcctcatcag cacgaccatg agtttccatg cttcctaact gccaagctac   1860
gaatggatag tactggttgc catcgttctt ggtagtagtg tacatatccg actgaacctc   1920
gtcataaaca tggaaagcta attgctccga ttcacgaagc agagaataca agccatctct   1980
gctctgacga gcctgagcta ttgttttgaa gggctctttc ttggccttat cttccggatc   2040
tctattcaga tcgcaggaaa cgagactcac agcaaaaaga gctgccgcag cccaatataa   2100
tatctttttc atattctttc ttctaaattt ctagttaaaa cgacagttgg atacctccca   2160
tgaattgttt cgtattgggg aactggttta gagcgacatt gcctccagcc tcagggtcaa   2220
agcctttgta cttagtcact gtgaagaggt tacgagccat taggtaaaca cgcgcacctg   2280
aaagaacttt ctgacctgca aacaagctat taggcaatgc ataggaaagt ttgaggttct   2340
tcaaacgcag aaaagaagcg ttttcaagca aatgggtatc gaactgagga gtttgaccca   2400
aacgaggcac atccgtatct ttatttgtct cagtccaagc atccaaaagg attttgctct   2460
tattagtttt tactccggaa ggtgcaccat tttcaataaa ataacggtcg ttattaatca   2520
tccacttacc tatgatatat gcgaaatcag catcaagtgc cagcccttt caagaggcac   2580
caagagagaa acctccggtg atatcggggg taaccgattt gcctacgttc acctccagtt   2640
cagtagagta tttgttcgtg gtaactctgt tgccatcagc atcatacttt ccgggaacat   2700
accacaacat atctcctgtc tcatgatcaa tacctgcata ttcggccatg tagaaagagt   2760
tgggtttacc cacctgccaa attgtacctg tattcggtaa tacatattct tcaagaccgt   2820
ggaatagctc cgtaatcttt tgcttgttga aattgaagtt tgccgaagca tatacattcc   2880
aatctttggt ttgatagatt gtaccatcaa gcttaatatc tataccggta tttctcattg   2940
agcccacatt ctgatactga gagaagaaac cactcgcata aggcatgggg acgtcgatta   3000
gcatatcttt cgtagagcga acatagaagt ctacctctgc tctaagtcta ttatcgaaca   3060
tcgcagaagc aactccgaca ttgaactgag cctgtgtttc ccaagacaaa tcggggttac   3120
cggccgtatt gataatgagg cccaaatcgt cgtcggtata gttgtacgca gaaacaaaag   3180
cctgatggcc atagttaccg atctcagagt taccggtcgt accatagctc actttgagcc   3240
```

```
gaagatcatt gagccaattg cttccctgaa tgaacttatt atagatgtcg aacatagcac    3300
ctgccgagta gaacatcgca ctacgattgt tctcaccgaa gcgagaagag cggtcattac    3360
gcagagatag gtctacatac atccacttgt cgaaaccata gctaccacga ccaaagaaag    3420
agagataagc ataagcttcc ttctgctgag caggaagaat caaattatca cccttctttc    3480
cctgagaaag caacatcata tcggcatttt cataaccttt ggcctgagca cggaaccatt    3540
ccaactctgc atcgataaac tcatgaccca gcaagagggt aacatcatgc ttgtcttcta    3600
cattaaactt gtattcggca gtattggtag aagtgtaaac acgtcttccg tcaaaacgct    3660
ctgtacgtga accaagatgg gttccggcca aggggttgtt tggtaaactt ttgcccgtat    3720
aacgtgtgtc tttaatatca gcacctacct gagcctttaa tgtcaggccc ttgataggat    3780
tcaattggag atagcctgtt gtaatcgctt ggaaagaagt atattccgca ggataccatt    3840
tataatcacg ctcagggctc tggaacacac gtgtagcacc cgaaatgaaa taagcctcag    3900
ccaattcatc gctatgtttc ccattagaga tcaagaatgg attgaaaaac ttcggcatag    3960
acaacgctcc aaacgtaccg gtattatagt aatttgtacc actgaaagaa gacgttttt    4020 gattagccat tgaacctgaa agattcatcc caatcttcat ccaatcattg attcggctgt    4080
caagattgaa tcgagtagtg tagcgtttga agagagaagg ctcgcgagag ataccctcct    4140
gatcaaaata gcctagtgac acataataag aagtaccggt agaaccgccc gaaaagttg     4200 catccacttg tgtggtagga gctgttggac ggataaagta tttcagccag tctgcatcct    4260
cagagaagtc aaccggacga agtgtattat tcttcagtcc atcggcaagc aagggatact    4320
gattgaacaa atcttcggcc tcttggatat acttcttcat cacggcgtcc acctgatcag    4380
gatcgttcgg attattgaga gcattaccat ggagaccaga gagcatctga tacttaagat    4440
gttccattcc cgtcatcata ttctctgtgg gttctcttgct aataatagaa gaaactccat    4500
agctggcact gaacgttaca cgaccggtct cactcatctt acctctttc gtttggatca    4560 gaaccacacc gttagcagca cgtgcgccat agatggaggt agcagaagca tccttgagta    4620
cggtgactga ttcaaagtca ttcgggttca tcgcagccac aacagccaat gtagtcgcca    4680
ctccatccac gatgtacaga ggagctgtac cagcacccaa agaaccgaca ccgtgaatag    4740
tcacattggc tacctggttc gggtcaccgg atgtagtcat aacctgcata ccggctacct    4800
gaccttggag ggcatccatg atgttggcaa cgggcttttc cgcgagcttt tcgctggaca    4860
ctttggccac agaaccggaa acggtgctga gtttctgtcc cgtaccataa cccaatacaa    4920
ctacctgctc cagaacctta gagtccggat ccagtacgat cttcatcaca ttagcgatgg    4980
cgacctcttt ggtagtcata ccggaatatg acactctcaa cattttggca ttggcaggca    5040
cgctaagcgt gaagttgcca tccaagtcgg ttgcagcacc gatagtggtg tttccgacaa    5100
ccacgacatt cgcgccgatc aggggctcat tatcctcgga ggagataact gtacccttca    5160
cggttctatt ctgggccata gcccacccaa tgctcgtcag caagcaaagg aagaatagcg    5220
tcattctttt catagacttt tcttttgcgt taaacttaaa attattactg ttatgttgtt    5280
ttcttttctt ctccggtttt accctaacca agggaagtct caaaaagccg ctaccggcct    5340
tagacacaag tcacgaaact tccacaactg ccctatgata cggacagcca caaaactaaa    5400 taaaaaatg caaccagact aatcctatta tccttttttt catctaagca atttgctcac     5460
catacgattt gtcaaatcca ctttgcaaaa ggagcagcaa taaaccgatg taaatttgaa    5520
ttttggaaga cagagtgttt cttttgaccg atcgaacact ctcaatattg agacaccttg    5580
attccacatc aatgctattc tcctgatgct tgtgaactac tgtctcggaa tacgagccta    5640
```

```
aaacacttcg atttcagttc gattttatgg aataaagtgg cgcaggattt ttttcgtttt      5700
ggctcgatat tttttcactt ctcgcgccaa aatgaaaaag tttacgcgcc acgttttttag     5760 aaaccacaaa tgcagaaatt tctgcaacgt gacatgtgat gtaaggtcct aaagaggaag      5820
attgtaatgc cggcagactc gctataaatc gcaggtatta atccccggca atgagtaatg     5880
ttcttttctc ctcgggaact atgattcgga gggatcccca taagagcaaa agcgattcgt     5940 caatttcct taacccaaac gtctcattcg gggaacggat tcgggaaccc aaaaaagaaa      6000
accatggcat ctcgactcac ttcctgccac aagagaaaaa tcaaggggga gccgcaaatg     6060
aaatactcgc gactccccct tacttggttt gagagaaata tcagatgctg aaagctactg    6120
tatggaagaa caacagtcct atagtcgcaa tagcatcatc ttcttcacat tat           6173

<210> SEQ ID NO 2
<211> LENGTH: 7361
<212> TYPE: DNA
<213> ORGANISM: Porphyromonas gingivalis
<220> FEATURE:
<223> OTHER INFORMATION: The following sequence is named Thai rag

<400> SEQUENCE: 2
caaagtcctg ccacgagtag caatgtaagg aaagttgtag tcaactaata atgtgaagaa       60
gatgatgcta ttgcgactat aggactgttg ttcttccata cagtagcttt cagcatctga     120
tatttctctc aaaccaagta agggggagtc gcgagtattt catttgcggc tcccccttga     180
tttttctctt gtggcaggaa gtgagtcgag atgccatggt tttcttttttt gggttcccga     240 atccgttccc cgaatgagac gtttgggttg aggaaaattg acgaattgct tttgctctta      300
tggggatccc tccgaatcat agttcccgag gagaaaagaa cattactcat tgccggggat    360
taatacctgc gatttatagc gagtctgccg gcattacaat cttcctcttt aggaccttac      420
atcacacgtc agttcgacgt aagaaaaagc caatggattt gttttctgat tagtggtaaa       480
cgcccaaaga acgtgggcaa tatgcttgaa aaagtagcga attatttgta tcttagcagt     540
tgataatcaa taagatacga acaaacaaaa cgctacttta tgaagacaaa tatagttgat     600
gttttttgca tcatagatga tttctccaag cttttttgatg aaacaatcaa gaaaaagacc     660
ctcgaagagg cagacaaaaa aggcaggaat agaaagttta agatgtcgga cagtgaggtc    720
atgaccatcc tgatcctgtt tcatctgtca agataccgag atttgaaagc ttttttatctt     780 caatacatct cccattcttg tcgatccgag tttccacatc ttgtctctta atcgctttt       840 gtggagctgc aaagcagggt aggtttcaag ctgatagcat ttctcaatat gtgttgtttg    900
ggtcaatgta caggcatctc tttcatcgat tccaccccat tgaaggcttg tcatatcaaa    960
cgagctcatg gcataggac aatgagggga tgggctcaaa aaggcaaaag caccatgggt     1020
tggttttatg gattcaagct acatattgtt atcaacgaca ggggtgaaat catcaactat    1080
caaatcacac cggcaattg tgatgacaga gaacctctga aagacggaac attcaccaag    1140 aatcttttg gcaaactcat tgccgataga ggctacattt cccaaaacct ttttgaccgg     1200
ctctttgtcg atgacatcca catgataacc aaaatcaaaa agaacatgaa gaactccctg    1260
atgcatctat atgacaaagt tttattgaga aagagagccc tgatcgaaac agtcaatgat    1320
atgctcaaaa atgtctgtca gatagagcac acgagacatc gcagtgtcaa caattttgtc     1380
accaacctga tctccggtat catcgcttac aacatcctgc ctaaaaagcc tgaactcaat    1440
attgaaatca tcagaaaccc taactttcct atttccgctt agatcgaact gacgttacat     1500
cacatgtcac gttgcagaaa tttctgcatt tgtggtttct aaaaacgtgg cgcgtaaact    1560
```

```
ttttcatttt ggcgcgagaa gtgaaaaaat atcgagccaa aacgaaaaaa atcctgcgcc      1620
actttattcc ataaaatcga actgaaatcg aagtgtttta ggctcgtatt ccgagacagt      1680
agttcacaag catcaggaga atagcattga tgtggaatca aggtgtctca atattgagag      1740
tgttcgatcg gtcaaaagaa acactctgtc ttccaaaatt caaatttaca tcggtttatt      1800
gctgctcctt ttgcaaagtg gatttgacaa atcgtatggt gagcaaattg cttagatgaa      1860
aaaaaggata ataggattag tctgttgca ttttttttatt tagttttgtg gctgtccgta      1920
tcatagggca gttgtggaag tttcgtgact tgtgtctaag gccggtagcg gcttttgag       1980 acttcccttg gttagggtaa accggagaa gaaaagaaaa caacataaca gtaataattt       2040
taagtttaac gcaaaagaaa agtctatgaa aagaatgacg ctattcttcc tttgcttgct      2100
gacgagcatt gggtgggcta tggcccagaa tagaaccgtg aagggtacag ttatctcctc      2160
cgaggataat gagcccctga tcggcgcgaa tgtcgtggtt gtcggaaaca ccactatcgg      2220
tgctgcaacc gacttggatg gcaacttcac gcttagcgtg cctgccaatg ccaaaatgtt      2280
gagagtgtca tattccggta tgactaccaa agaggtcgcc atcgctaatg tgatgaagat      2340
cgtactggat ccggactcta aggttctgga gcaggtagtt gtattgggtt atggtacggg      2400
acagaaactc agcaccgttt ccggttctgt ggccaaagtg tccagcgaaa agctcgcgga      2460
aaagcctgtt gccaacatca tggatgccct ccaaggtcag gtagccggta tgcaggttat      2520
taccggttcc ggtgaccota ctgccgtcgc ttctgtgaag atccacggtt cagggtcttt      2580
gacttcaagt tcagccctc tctacatcgt ggatggtgtg ccgactgatt tgggtgtagt       2640
tgccggtatg aaccctaatg acttcgaatc gtttacgatt cttaaagacg cttcttctac      2700
ttctatctat ggtgcgcgtg cagccaatgg cgttattgtc attacgacca aacgcggaaa      2760
gatgggagag cgtggccgta ttacgttcaa cgccagctat ggagtgtctt ctattattaa      2820
taaaaaaccc ttcaagagca tgatgacggg agatgaattc gcccgttggc agtatggtgt      2880
cggctatgct gcagcagatc aatacagtac tttcgaggca tggaaagacc acattaaaga      2940
ggatgctaag caagcattga taaactactc accttatctt gaggatcaaa tcaagaaagg      3000
tatacttgat ccgataaact ttgataaaga tacggattgg ctgggatacc atttccgcac      3060
tgctcctacc actcaaggag atgtttctat ccagggaggt tcgcaaggca cttcttactt      3120
cttatctttg ggatattttg accaagaggg tatctctcgc tcggaatctc ttttgaagcg      3180
ttatacaggt cgtcttaact tggaaagccg tgtgaacgat tggttgaagg ttggagccaa      3240
tatgtcggca gctcttgcca aaagacgtgc ctctggtttt gcttcttctg cgtatatctc      3300
agaaggatca tttgctgctt tggttgctgc tccttatctg aatcccata caacatcagg       3360 cgattttgct gaagcgtatt acatggattt tcaagacaaa gtaatattcg gaattccgca      3420
ccgtgacagc tatcgtcctt ataatcgtga agcttatcaa gcaacgatga gtggatatgc      3480
acaactcaca ccgataaagg ggctgacgct caaggcacaa gccggcttcg acttttgca       3540 agaacgcact tcttctaaac tgcttcccaa taaccccttg gcattggacc cgttgggtac      3600
aagtcgggag cgttttttatc actatttgac caaaactttt accacacggg cagagtataa       3660
gttctcggta gaagataagc atgacgtgac tcttttggca ggccatgagt ttatcgatta      3720
cgaatatgat atgtttggag ccttaggaaa gggttacgaa aatccgaaat tcatgatgct      3780
tagccaagca aaaggtgata cttatttgac tttgcccgaa caggcaaaag ctgaatatgc      3840
ctatctctct ttcttcggcc gtggtagcta tggttttgac aagtggccttt atgtagacct      3900 ctctgttcgt aatgatagat cttctcgctt tggtgccaat aaacgtagtg cgatgtttgg      3960
```

```
atccggtggc gttatgatgg atgttttcaa caaattcatt aaagaaagca cgtggctcag   4020
tgatctgcgc tttaagatga gctatggtac taccggtaac tccgaaatga gaaattacac   4080
aactggaaac cctgaatatt atgctcattt ggctttggtt ggtagcaatc catatacgga   4140
caacgctttg ggccttttcgg tggctacacc gggtaaccct aatctttcat gggaacaaca   4200
atctcagttc aatgtaggtg ttgcttcttc attctttgat ggtcgactca acgctgaatt   4260
ggatttctat gttcgtgcta cagacgatat gcttatcgag gtgcctctgc cttatttgag   4320
cggattcacg gctcagttgc agaatgtggg tgctatgaag aataccggtt tcgatattac   4380
tgttagtggg gatattgttc gaagcaagga cttcaaggtg tacggatcag ctacatttaa   4440
ctataaccgt gaagaaatta cacgtctatt ctccggtctc aaggagtacg ttcgtgatgg   4500
atatagctat tcatggattg ttggcaagcc tacagtattc tattgtgctg aatatgctgg   4560
cgtttataaa ggccaagccg gccccaatta tgtggatgct gaaggcaagc cctttaaggg   4620
tggagaccaa atgtggtatg tccccggaga atacaatgaa gatgggagtc gcaagcttac   4680
caataaatat tcttcttcat ggagcatgc tctgacagat aaggctctca ctcctcccgt   4740
tacaggagga ttttccttag gtgcttcatg gaaagacctt tctttggatg cagatttctc   4800
ttatattctg ggtaagtgga tgattaataa tgaccggtat tttacagaaa atacttcccc   4860
cggttttaac tttacaaata aagacaagat gatactgaat gcatgacgc agcagaattc   4920 tgattcggat gtgccccgta tcggtcagtc gatgcatttt gactctcgct tgttagaaaa   4980
cgcttctttc ttgcgtatga agaatctgaa attgacttac aacctgcccc aaaatctctt   5040
cgccggtcag aatgtcctct cgggagcgcg tgtctacttg atggctcgta acttgtttac   5100
aattacaaag ttcaaaggtt ttgaccctga agcaggagca atctatctta tgaaccagta   5160
tcctaatact aaacagtacg tggctggtat tcagttgtct ttctaatgca attcactttt   5220
aaagaaaaca atgaaaatga aaaaaataat taattatgct gtggccggat tgctactcgt   5280
ttcaagcttt gccgcttgtg acttggatcg cactcctcac aattctgatg tccaaaagcc   5340
ttatgaagat atggccacca cagttcagta tagagatgga ttgtattctg ttcttcgtgg   5400
tgcagagaat gccggacggt atactttgtc agaatatatg tccgatatgt attgtgtaat   5460
gcaaggagat ggtggccatg ctacgcctta tgttacatgg acgattcctc gcattgagat   5520
tgctgaccac gcatcgaatt attactttgg ttttaatcgg ttaattcagc aagccaatgc   5580
ttttgtcgga aatgttaagc tggcaatcgc aaatggggtt tataagacag aagttgataa   5640
aaccaatgct caaatttatt tggctgaggc caagactttg caggctttag ctttgttccg   5700
tcttatggag cgctttgcct atccctatga tccaaacgaa accacttctc cgaaaaactt   5760
gggggtggtt ttgataaagg aatatgatcc ttgggctgtg ggtgcacgag ctacgcagac   5820
ggaaacgtat agctatatta tgagccttct tgatgaggcc atctctgttt tgcctgaaac   5880
gaatgcgaac aatatgtatg tgagtcggga ttatgcttta ggcttgcgtg ctcgcgtaca   5940
catggcgatg gataactatg ctgaagccgc caatgatatc agagcttttt ataaaaagta   6000
caatctgatt tctgctgcta attccgatga atttgaggag gcttatagaa agatgagctc   6060
caatcctgag cttatttttcc gcggatatgc ttccgttact aacggatacc ttgtgtatca   6120
ggatttgatg ggagcaacag cttctggaac taatgtgaag tacaaccctc gtgttacccc   6180
tctgcaatgg gtttgcgacc tttatgatgc ggctgattat cgtaagaaag tgtacattgt   6240
agacaaggtg aacggtgacg gtggcaaagg ttatgtcgta aataagttcc ttggagaccc   6300
tgaacttcgt gaagaccta agaaggaaaa tttcaaaacc ggttgtcgtt tcttctctct   6360
```

| | | | | |
|---|---|---|---|---|
| cgcagaagcc | tatcttatct | tggcagaagc | agatattatg | actggtaata | cagccgaggc | 6420 |
| tatggaagtt | ctgaaagagc | tgagtaagtc | tcgtggagca | gaggtttccg | gtgcagatta | 6480 |
| tatgcaaatc | ctcaaggatg | agcgtacacg | agaaatgatc | ggtgaaggtt | ctcgtctcaa | 6540 |
| tgacatgatt | cgctggaata | tggatttggt | ggtatctccc | gttcaggctg | ttcttcataa | 6600 |
| aatagctgtc | ccgactatcc | ttcagactga | tgacccgaca | cgtgttcctg | ccggcttcta | 6660 |
| tgctttcacg | tgggaaattc | ccaatcgtga | tcttgtagtt | attcccgagc | tggttcgcaa | 6720 |
| ctggccaaaa | cagtaagtag | cattctttt | tttagcaact | tgctatccta | ttgcagggag | 6780 |
| caccggtttc | cggtgctccc | tgttcgcttt | attgcatgtg | acgatttata | atgcagaagt | 6840 |
| cttcttcaag | ctagtgagac | aattttgttt | aatacgagaa | tccgggaaac | gagtgttgtc | 6900 |
| ctatagcata | agtcggcaga | tgtcttatct | ttgtacacta | aatatcagta | ggtatgtgta | 6960 |
| agaaacattt | catccaatac | ttcttttgga | ctatcattgt | ctttttttgtg | ggtggggcta | 7020 |
| ttcactcttg | taaggagtct | aagatagatc | ttgaagaagt | tagcatagtc | gatctgcaga | 7080 |
| tccaccgatt | ctaccttttcc | agtaagaaaa | atccggattt | ggaaaaagta | ttttctcta | 7140 |
| tcgatcatgc | aaaagggaca | attattaata | agaaatatat | gccttatggc | acagttttgg | 7200 |
| attccgtaat | gatgaagctc | gtgactgatt | tctccgcgaa | aaaactgcga | gtggccatca | 7260 |
| atgatggaga | atataaggat | tggcataata | aggattcgtt | gtggttgcgc | gattgtcata | 7320 |
| ccttgcattt | aatggtttcc | gacgaaagtg | gcgagaaaac | g | 7361 |

<210> SEQ ID NO 3
<211> LENGTH: 8346
<212> TYPE: DNA
<213> ORGANISM: Porphyromonas gingivalis
<220> FEATURE:
<223> OTHER INFORMATION: The following sequence is named W50 rag

<400> SEQUENCE: 3

| | | | | | |
|---|---|---|---|---|---|
| caaagtcctg | ccacgagtag | caatgtaagg | aaagttgtag | tcaactaata | atgtgaagaa | 60 |
| gatgatgcta | ttgcgactat | aggactgttg | ttcttccata | cagtagcttt | cagtatctga | 120 |
| tatttctctc | aaaccaagta | aggggagtc | gcgagtattt | catttgcggc | tccccttga | 180 |
| tttttctctt | gtggcaggaa | gtgagtcgag | atgccatggt | tttctttttt | tgatccccga | 240 |
| atccgttccc | cgaatgagat | gtttgggttg | aggaaaattg | acgaatcgtt | tttgctctta | 300 |
| tgagaccttt | gcacggcgat | tggcgtatat | tttgtttgtt | aattcattgt | ataataggga | 360 |
| gttattttgt | atatttgagt | attaaaaaca | gcataatatt | cctcccatgg | cataccaatc | 420 |
| caagaatacc | gatgagcatg | taacatttgc | agacgcactc | cttcaaagc | gttatcgcaa | 480 |
| agcacaaaac | gacttcctca | atcaggttga | caggcttatc | gattggcgtc | cgatcaggac | 540 |
| gctgatcaac | aagaaataca | ccaagcgaca | aaatgccatc | ggcgccccgg | cttatgacgt | 600 |
| gattctctta | ttcaagatgt | tgcttttgga | gacatggtac | aacctcagtg | attgtgcttt | 660 |
| ggaggagcgc | atcaatgatt | caatcacctt | ttcccgattc | ttgggggctga | agatggaaga | 720 |
| ggtttctccc | gaccacagta | ccatcagtcg | atttcgttcg | gcactgacag | agttgggtct | 780 |
| catggacaaa | ctattggcgc | agtttaacaa | acaacttttcc | cgccatcaca | tttcggtcag | 840 |
| ggaaggggtg | cttgtcgatg | caagccttgt | ggagacgccg | cataaaccca | acggaagcat | 900 |
| tacgattgaa | gtcgcagacg | acagagaaga | caatcggagc | gaggaggaaa | agaggcaga | 960 |
| ggaggattat | caaaaacagg | ttgtccgtca | gcgtaaaggg | acggatgaag | aagcccgttg | 1020 |
| ggtttacaaa | caaaagcgtt | atcactacgg | atacaaaaag | cattgtctga | ccaatgttca | 1080 |

```
aggcattgtt caaaaggtga taacgactgc agcgaaccgc agtgacacga aggagtttat   1140
tgcgctattg cagggtgcaa acatacctca aggctcagcc gtcttggcgg acaaaggata   1200
tgcttgcggg gaaaatcgtt cctacctgca aacccatcac cttcaagacg gcatcatgca   1260
caaggcacaa cgcaacaggg cattgaccga ggaagagaag caacgaaaca aagcaatcag   1320
tcggatacgg agcaccatcg aacgcacctt tggcagtatt cgccggtggt ttcatggcgg   1380
acgatgtcga taccggggac ttgccaagac ccatactcaa acattcttg aaagcatcgc    1440 ctttaattta tacagaaccc cggggataat tatgtcctca tttgtaggat aaggcataac   1500
cccccttgag gagctcgtgc aagcagctcc tcaagggggg atttacaact actttcactc   1560
cttactgcca cccctttcac tcgctccttt tatgccaaga actcctcttc cctccacctc   1620
cttattttgc aaaggtctcc ttatgggaat ccctccgaat catagttccc gaggagaaaa   1680
gaacattact cattgccggg gattaatacc tgcgatttat agcgagtctg ccggcattac   1740
aatcttcctc tttaggatct tacatcacat gtcacgttgc agaaatttct gcatttgtgg   1800
tttctaaaaa cgtggcgcgt aaacttttc attttggcgc gagaagtaaa aaaatctcga    1860
gccaaaacga aaaaaatcct gcgccacttt attccataaa atcgaaccga atcaaagtg    1920 ttttaggctc gtactccgga gacagtagtt cacaagcata caggagaata gcattgatgt   1980
ggaatcaagg tatctcaata ttgagagcgt tcgatcggtc aaaagaaaca ctctatcttc   2040
caaaattcaa atttacatcg gtttattgct gctccttttg caaagtggat ttgacaaatc   2100
gtatggtgag caaattgctt agatgaaaaa aaggataata ggattagtct ggttgcattt   2160
ttttatttag ttttgtggct gtccgtatca tagagcagtt gtggaagttt cgtgacttgt    2220
gtctaaggcc ggtagcggct ttttgagact tcccttgggt tagggtaaaa ccggagaaga   2280
aaagaaaaca acataacagt aataatttta agtttaacgc aaaagaaaag tctatgaaaa   2340
gaatgacgct attcttcctt tgcttgctga cgagcattgg gtgggctatg cccagaata    2400 gaaccgtgaa gggtacagtt atctcctccg aggataatga gcccctgatc ggcgcgaatg   2460
tcgtggttgt cggaaacacc actatcggtg ctgcaaccga cttggatggc aacttcacgc   2520
ttagcgtgcc tgccaatgcc aaaatgttga gagtgtccta ttccggtatg actaccaaag   2580
aggtcgccat cgctaatgtg atgaagatcg tactggatcc ggactctaag gttctggagc   2640
aggtagttgt attgggttac ggtacgggac agaaactcag cactgtttcc ggttctgtgg   2700
ccaaagtgtc cagcgaaaag ctcgcggaaa agcccgttgc caatatcatg gatgccctcc   2760
aaggtcaggt agccggtatg caggttatga ctacatccgg tgaccctact gccgtcgctt   2820
ctgtggagat ccatggtaca gggtcgttgg gggcaagctc tgcaccattg tatatcgtgg   2880
atggtatgca aacttctttg gatgttgtgg ctacgatgaa tccgaatgat tttgaatcta   2940
tgtccgtttt gaaagatgct tctgcaacat ctatttatgg agctcgtgct gcaaacggag   3000 tcgtttttcat tcaaacgaag aaaggtaaaa tgagcgagag aggtcgtatt acctttaatg   3060
ccagttacgg gatttctcaa atcctgaata ctaagcccct tgataatatg atgactggag   3120
atgaattgct ggattttcag gtgaaggcag gttttgggg gaacaatcaa accgttcaga    3180
aggttaaaga tatgatcctt gccggagctg aagatttgta tggcaattat gattctttga   3240
aagatgagta tggtaagaca ttgttcccag tggattttaa tcatgatgca gactggctca   3300
aggctttgtt taaaacagca cccaccagtc aaggtgatat ttctttctcc ggagggtctc   3360
agggaacttc atattatgcc tctataggct acttcgatca ggaaggtatg gctcgtgaac   3420
cggcaaattt taagcgctat agtggccggc tcaacttcga aagtcgtatc aatgaatggc   3480
```

```
tgaaagttgg tgcaaatttg tctggtgcga tagcgaatag acgatctgcc gactattttg   3540
gaaagtatta tatggggtca ggtactttcg gtgtgttaac gatgcctcgt tattataacc   3600
cttttgatgt gaatggggat ttagcagatg tctattacat gtatggagct accagacctt   3660
ctatgacaga accgtacttc gcaaaaatga gaccgttcag ttccgaatca catcaggcca   3720
atgtaaatgg tttcgcccag attactccga tcaaaggcct tactttaaag gcacaggctg   3780
gtgttgatat tactaatact cgcacttctt ctaagagaat gcccaataat ccgtatgatt   3840
ctactcctct tggggaaaga agagaaagag cttatcgaga tgttagcaag tcttttacaa   3900
atacggctga atataagttt tcaattgatg aaaaacatga tcttacagca ttgatggggc   3960
atgaatatat tgaatatgaa ggggatgtta ttggggcatc ttctaaagga tttgaaagtg   4020
ataagttgat gttactgagc cagggaaaaa ccggaaatag tttgtctttg cctgaacaca   4080
gagtcgctga atatgcctat ttgtcttttct ttagtcgttt taattacggt tttgacaaat   4140
ggatgtatat agatttctct gttcgtaatg accaatcctc tcgattcgga tccaataata   4200
gaagcgcgtg gttctattct gtcggtggaa tgtttgacat atataataaa ttcattcaag   4260
aaagtaattg gctcagtgat cttcgactga aaatgagtta tggtacaacg ggtaactcgg   4320
agattggtaa ttacaaccac caagcactcg ttactgtgaa caattatact gaagatgcta   4380
tggggcttag catttctaca gcaggcaatc ccgacctctc gtgggaaaag cagtctcagt   4440
tcaacttcgg tttggctgca ggggctttca ataatcgctt atctgcagag gtagatttct   4500
atgtccgcac tacgaatgat atgttgattg atgtcccgat gccttatatc agtggttct   4560 tctcacagta tcagaatgta ggctctatga aaaatacggg tgtagacctt tctcttaagg   4620
ggacgatcta ccaaaataag gactggaatg tatatgcttc tgcgaatttc aactacaata   4680
gacaggaaat aacaaagctt ttcttcggtc tcaataagta catgttgcct aataccggta   4740
ctatatggga aattgggtac cccaattcgt tctatatggc tgaatatgct ggaatcgaca   4800
aaaaaaccgg taagcagttg tggtatgttc ctggtcaagt cgatgcggat ggtaataaag   4860
ttacaacaag ccagtactca gctgacttgg agacacgaat tgataagtct gttactcctc   4920
ctattacagg tggtttctcc ttaggtgctt cttggaaagg actttcttta gatgctgatt   4980
ttgcctacat cgttggtaaa tggatgatca ataatgaccg ttactttaca gagaatgsag   5040
gtggattgat gcaattaaat aaagataaaa tgctattgaa tgcctggaca gaggataata   5100
aagaaacaga tgttccaaaa ttgggacagt ctcctcagtt tgatacgcat ttgttggaga   5160
atgcttcttt cctgcgtttg aagaatctca aactcaccta tgtactcccc aatagtcttt   5220
ttgctgggca gaatgtgatt ggtggagctc gtgtctattt gatggcgcgc aatctgttaa   5280
ctgttacgaa gtataaaggc tttgaccctg aagcaggggg gaatgtggga aaaaatcaat   5340
atcctaattc taagcagtac gttgcgggta ttcagttgtc tttctaagat ttacttattc   5400
ttaagaaaca tttgatatga aaaaaataat ttattgggtt gcgacagttt tcttagcagc   5460
gagcgtatcc tcttgcgagc ttgaccgcga ccccgaagga aaagatttcc aacagccata   5520
tacttctttc gtgcagacga aacaaaacag agatggtctt tacgcacttt tgcgtaatac   5580
tgaaaatcca cgaatgcatt tttatcagga acttcaatcc gatatgtatt gcactaccat   5640
tactgatggt aactccttag ctccgttcgt gaattgggat ttaggcatac ttaacgacca   5700
tggacgtgct gatgaggacg aagtctccgg tatagctggc tactatttcg tatacaatcg   5760
actaaatcag caagcgaatg cttttgttaa caatacggaa gctgcgttgc agaatcaagt   5820
gtataaaaat tccaccgaga tcgccaatgc taagagcttt ttggcggaag gaaaagtttt   5880
```

```
acaagcattg gctatttggc gactgatgga tcgttttagc ttccatgaaa gcgtgacaga    5940
agttaattcc ggtgcgaaag atcttggcgt tattctgttg aaagaatata atcctggtta    6000
tatcggtccc cgtgcaacga aggcacaatg ttatgattac attttgtcac gtttgtctga    6060
ggctattgaa gttttgcccg aaaacaggga aagcgttctt tatgtgagcc gtgattacgc    6120
ctatgccctc cgagcaagaa tttacctcgc gttgggtgaa tatggaaaag ctgcagcaga    6180
tgctaagatg gttgttgata agtatccttt gattggtgca gcagatgctt ctgagtttga    6240
gaatatttat cgatcagatg ctaataatcc cgaaattatt tttcgtggtt ttgcttctgc    6300
gactcttggc tcgtttactg ctacgacact aaatggtgct cgccagcag gtaaggatat    6360 aaaatataat ccgagcgcag tcccttttcca atgggtagtg gatctttatg aaaacgaaga    6420
tttccgcaaa tccgtatata tcgcgaaagt tgtgaaaaag ataaggggg atttagtaaa    6480 taaattcctt gaggacaagg cttatcgtga tgttcaggat aagccaaacc ttaaagtcgg    6540
agctcgttat tttagcgttg ctgaggtcta cttaattttg gtagagtctg ctcttcagac    6600
tggagatacc ccaacagccg aaaaatatct caaggctttg agtaaagctc gtggagcaga    6660
agtttcagtc gttaatatgg aagcactgca agcagagcgt acgcgtgagc ttataggtga    6720
gggtagtcgt ttgcgtgata tggtccgctg gagtatccct aataatcatg atgcttttga    6780
gactcagcct ggtttagaag gttttgcaaa tactactcct ttgaaagctc aagctcctgt    6840
aggcttttat gcatatactt gggagttccc acagcgagat cgacaaacta atccgcagtt    6900 aataagaac tggccgatat aatttagttg tagatcttac tatgaaatat ggggctgcat    6960
caaaattttt tttgtcgcag cccctatctt ttcatactca taatacgagg aagccccaac    7020
tttcacaagc tagggctttg ttcgtttctc aatttttgga aaattggggg atatcaacaa    7080
attaatgggt gaaaagttgt gtttccctcc ttgtgtagtc gtcccttaaa aggactctta    7140
agggacgact aaatatgctt ttcaatacgc ccatgatctt tctctattgt ttcccaagaa    7200
tgaagcttat atttccctga aaacgcatct tggacatctt caaacaaata cttctgatta    7260
gctttgaggc taagaatata gtcggcctct gattgaataa tcacttcagc aatagctgtt    7320
tgtattccca ttgcatcaat actaacaact gatccactta atcaagact atccggtact    7380 tcgggaatag cttgtaattc attgtgtttg tctgtaactg tctcttgaca agacttaagc    7440
tcacttgatc aatccatgcc gagagtatat atgtacaccc agtcttcttt gggagctacg    7500
caaacgcttg ccatctatgg caatatgttt accctctaaa tcgctaatca agtcttttcc    7560
ataaacactg agacaagcgt aaagagcaat gaggttcaat gtgttggagt acacgctcaa    7620
acgtatctgc ggcaggacag ccgttaggaa gttcaaccaa tggacgaaag gattcttctc    7680
gctctaaacc cagttcgtgc attgactcat aatcctatcc accaaacaga taactcgcca    7740
aggcgataac taaaatgtcg cttaacttat acttacagcg acctacaaca cgaggatctt    7800
ttacctcctt gaaaaatctg ttacatgcat aatcccaaag atatccttat tttgatgcgg    7860
ttgccctgga tgcgatagcc tgcaattgtt acataagtcg gcagatatct tatctttgta    7920
cacaaaatta ttataggtat gtgcaagaaa catttcatcc gatatctctt ttggattttt    7980
atctcctttt gctcaggtat agctttggtc tcttgtaagg agtccaagtt agatctcgaa    8040
gacgtgaatg tggttgatct gcaaatccac cgattctacc tttctactaa gaagaatccg    8100
gatttagaaa aagtgttttt ctctatcgat catgcaaaag ggacaattgt taataagaaa    8160
tatatgcctt atggcacggt tttagattct gtcctaatga atctcgttac ggatctctct    8220 gcaaaaagt tgcaagtagc ggttaatgat ggggagtata aagattggca taataaagat    8280
```

```
tcgttgtggt tgcgcgattg tcataccttg catttaatgg ttttcgacga aagtggcgag    8340
aaaacg                                                               8346

<210> SEQ ID NO 4
<211> LENGTH: 7227
<212> TYPE: DNA
<213> ORGANISM: Porphyromonas gingivalis
<220> FEATURE:
<223> OTHER INFORMATION: The following sequence is named 381

<400> SEQUENCE: 4
tgtgaagaag atgatgctat tgcgactata ggactgttgt tcttccatac agtagctttc      60
agcatctgat atttctctca accaagtaa gggggagtcg cgagtatttc atttgcggct     120
cccccttgat ttttctcttg tggcaggaag tgagtcgaga tgccatggtt ttcctttttt     180
tgattcccga atccgttccc cgaaagagat gtttggggttg aggaaaattg acgaatcgtt     240
tttgctctta tgggaatccc tccgaatcac agttctcgag gagaaaagaa cattactcat     300
tgccggggat taatacctgc gatttatagc gagtctgccg gcattacaat cttcctcttt     360
aggatcttac atcacatgtc acgttgcaga aatttctgca tttgtggttt ctaaaaacgt     420
ggcgcgtaaa cttttttcatt ttggcgcgag aagtaaaaaa atctcgagcc aaaacgaaaa     480
aaatcctgcg ccactttatt ccataaaatc gaaccgaaat cgaagtgttt taggctcgta     540
ctccggaaac agtagttcac aagcatcagg agaatagcat tgatgtggaa tcaaggtatc     600
tcaatattga gagcgttcga tcggtcaaaa gaaacactct atcttccaaa attcaaattt     660
acatcggttt attgctgctc cttttgcaaa gtggatttga caaatcgtat ggtgagcaaa     720
ttgcttagat gaaaaaaagg ataataggat tagtctggtt gcattttttt atttagtttt     780
gtggctgtcc gtatcatagg acagttgtgg aagtttcgtg acttgtgtct aacgccggta     840
gcggcttttt gagacttccc ttggttaggg taaaaccgga gaagaaaga aaacaacata     900 acagtaataa ttttaagttt aacgcaaaag aaaagtctat gaaaagaatg acgctattct     960
tcctttgctt gctgacgagc attgggtggg ctatggccca gaatagaacc gtgaagggta    1020
cagttatctc ctccgaggat aatgagcccc tgatcggcgc gaatgtcgtg gttgtcggaa    1080
acaccacgat cggtgctgca accgacttgg atggcaactt cacgcttagc gtgcctgcca    1140
atgccaaaat gttgagagtg tcctattccg gtatgactac caaagaggtc gccatcgcta    1200
atgtgatgaa gatcgtactg gatccggact ctaaggttct ggagcaggta gttgtattgg    1260
attacggtac gggacagaaa ctcagcactg tttccggttc tgtggccaaa gtgtccagcg    1320
aaaagctcgc ggaaaagcct gttgccaaca tcatggatgc cctccaaggt caggtagccg    1380
gtatgcaggt tatgacctct tcgggagacc ctacgaaggt ggccaacgta accattcacg    1440
gtaccggatc tttgggcgca agctcttccc cactttatat cgttgatggt atgcagacgg    1500
atctgtcagt ggtggctacg atgaacccga atgattttga caacgtaaca gtcttgaagg    1560
atgcttctgc aacttctatt tacggtgcgc gtgctgccaa tggtgttgtg attatcacta    1620
ccaagagagg taaatgggt gaagccggcc gtattacatt caattacagc tacggtgttt    1680
cttctattat cagtaagaag cctatgagcc gaatgatgac tggagacgag cagcttaact    1740
atcagtttaa taatggttat tgggatacta ctaagccgga gtatgcaacg atcgaagcag    1800
tcaaagctac tttgatcaaa aatgcagagg atatgtatgc caaatacccg gagcttgctc    1860
ctcttgtgaa atccggatat ttaaagccaa ttgattttga taatgatacc gactggcttg    1920
agtatttcat tcgtcctacg gctccgacgc accaaggtga tatttctttc accggaggaa    1980
```

```
gtcagggac  ctcttatttt  gtttctttgg  gttatttcaa  tcaagaaggt  atttcccgtg   2040
agccttcttc  tttcaagcgc  tatagcggcc  gtatgaattt  ggaaagccgt  attaaggaat   2100
ggctgaaatt  aggtctgaat  ctttcgggtg  caatcgctga  aaagcaagca  tcatcgttct   2160
caggaaccaa  ttattataat  acaggaactt  ttggtgcatt  atctatgcct  aagtatctga   2220
atcctttaac  gagtgatggt  gagattgccg  acgtatacta  tatcatagga  accactcctc   2280
gccaaagtcc  attgcgaatt  gctaaatggt  accccgaaga  agattatact  tatcaagcaa   2340
atgttggtgg  atatttgcag  ttcaatccga  ttaagggact  tacaattaag  tcgcaagcgg   2400
gtttggactt  tacggacagc  cgtgctacag  taaagacact  tccgaataat  atttttctc   2460 ctaatcctct  gggcaacagg  acagagcgct  tctatggcgg  acggttgttt  acagtcacaa   2520
acaccggtga  gtataaaacc  aattttgaag  agttgcacga  tgtgaccatc  cttttgggac   2580
aagaatttat  tgatgcagat  gtggatgttt  tcagcgcaag  agcaaatggc  ttcgagaaca   2640
gcaaggtaat  gcttttgtct  caggaaaaga  ccggtaattt  ccttcagctt  cctgctcagc   2700
gaaaagaaga  atatgcttat  ttgtctttct  tcggtagggg  tagttatgga  tttgacaagt   2760
ggatgtatct  ggatgtttcg  ttgcgtaatg  accaatcatc  tcgttttggt  gacaacaatc   2820
gtagtgcttg  gttctattct  ttcggttcga  tgttcgacat  ctacaataag  ttcatcaagg   2880
aaagcgattg  gctgagtgac  ctccgattca  agctgagtta  cggaactacc  ggaaactctg   2940
agatcggaaa  ctacaaccac  caggctctcg  taggaagcaa  taattatacc  gatacagcat   3000
tgggccttac  tgtctctaca  attggtaacc  ccgatctttc  ttgggaaaag  caatctcagt   3060
tgaatgtggg  tattgcttcc  ggttttttgga  acaatcgttt  gactgctgaa  gttgatttct   3120
acgttcgtac  aacggatgat  atgttgatca  atgtgcctct  gcagtatata  agtggtttca   3180
ccaaccagtt  ccagaatgtc  ggctcaatgc  aaaatacggg  agttgatgtt  aacttgagag   3240
gaactatctt  ccaaaataaa  gattggaatg  tttatgctgc  tgcaaacttc  aactacaaca   3300
aacagaagat  taccaagctc  ttcttcgatt  tgaaagagta  tgtacttccc  aacaccggaa   3360
ctatctggca  gattggaaaa  cctaattcat  tctatatagc  tgagtatgca  ggtatttata   3420
agggtacgga  gccttatacc  gacccggatg  gaaatgttta  tcatggtggt  gatcagttgt   3480
ggtatgttcc  cggcaaaaca  tgggctgatg  gtactccggc  tacaacgaat  gtctattctg   3540
cggatttgga  gcaagcggta  gataaggcag  tcaatccccc  tattaccggt  ggtttctctt   3600
tgggggcttc  ttggaaaggt  ctttcattgg  atgctgattt  tgcttatatc  attggtaagt   3660
ggatgatcaa  caatgaccgc  tacttcactg  aaaacggttc  tggcgctgca  atgagaacca   3720
ataaggataa  aatcctttg  gatgcatgga  ctccgcagaa  tcctaactca  gatgttccaa   3780
gactgggtca  agacaatcag  ttcgatagcc  gtttgctgga  gaatgcctct  ttcttgcgtc   3840
tcaagaatct  gaaattgact  tatgtccttc  ctcaatctct  attcaagact  caaggtgttg   3900
tttctggagc  acgtgtttat  ttgatggctc  gtaacctcct  gaccgttacc  aagtacaaag   3960
gttttgaccc  cgaagccggt  ggtaatgtgg  cactgaatca  attcccgaat  acgaagcaat   4020
ttgtaggtgg  tattcagatt  tcttttctaaa  cattgagtac  taacgattaa  cagtaaatca   4080
ttatgaagaa  aatattttat  gcagtgctgt  ctgctttcct  gctgttgggg  cttttttcat   4140
gcgatctgca  gcgtgatccg  gatggaagtg  atgaacagaa  agatcatttc  gcttcttttg   4200
tggagacaaa  acatttaga  gatggtttgt  atgctacgtt  gcgaagtaca  gaaaacccta   4260
ctcgtttcgt  atggcaggat  cttcaatcag  acatgtatgc  agtaacaacg  aatgatggta   4320
atacaagctc  tcgtttatc  acatggagtt  tgggtgcact  ggagtcatcc  ggtgagattg   4380
```

```
cttcatatta tctcgcttat tatagcttgt tgcagcgcgc caattatttt gtgaccagaa    4440
tagaacgttc tatggagttg aatctttatc tggagaaaga actcaaagat gtaaagatct    4500
ttcaagcaga aggtaagact cttcaggcat tggccctctc tcgtttgatg gagcgttttg    4560
cttataagta tgatcctgcg gccactactc atccgtatga tttgggtatt gtacttgtta    4620
aggattacaa tcctatgatt gctgcacctc gtaatacgca gaaagagtgc tacgattata    4680
tccttgaatg cttaaatcag gcgattgatg ttttgccgaa caagagcaat gaaggtaata    4740
tcagagtttc caagcattat gctcatgctt tgcgtgcacg tgtaaatttt gcaatgggta    4800
attatgatgc ggcaaaagaa gatgctaaag ttctggtcga caattatcct cttattgatg    4860
tgacgacagc aaagaaattt gctgaggttt accgcgatga tgctaacaac cccgaaatcg    4920
tattccgtgt ttttgcttca ggaactatcg gtactgttgc agaaacgacc taagcggat    4980 tcttgtggca ttcaggtgct cagcttgtgg tttcaagtcc tatttcagct ccttttccaat    5040 gggttgttga cctatatgat gataccgatt atcgtaagtc ttgctatatc acgaaagatt    5100
tctacgttat tggtggtggt gttgataagg ttatgtagt tggaaaatat ctgggtaacc    5160
ccgcttatca gtctaatcct aacgtacccg actttaaggt gaccagccgc ttcttctcag    5220
ttgcagaggc ttatttgatc atggcagagt ctatggccaa gtccggtgat gcagccggtg    5280
caaaggatct gttgaagacg ctttgtgaga acgtggtgg ccagttggaa gatgcgata    5340 tcatggattt ggtaatggca gaacgtaccc gtgagctgat cggagaaggc tctcgtctga    5400
acgatatgat tcgttggaat ttgcctaata ccacgatga tatggaaaat cagccggtat    5460
tcctgcagat cggtcttgca aaagctgata agctgaagca gcccgtacct gccggtcact    5520
atgcgtttac ttgggagttc cctgttaggg atcgtcaggt gaatccgcag attatcaaaa    5580
actggccgaa ctaattcaat tagatgtttc gacgcgcttg gggttaatct ttataatccc    5640
aagtgcgttt gaaacctttc ttgactttta ggcgaaaaga ctttctgtg gtgtgtttgg    5700 aatcgtgcca agaaagtcca aaatataaac ggttccggtc aaacaaaaat caaattcaaa    5760
ttatgaagaa aattttctct ttgttgggtg ctatgttctt gatgggttca ctcagtgctc    5820
aaaacacaat cccccaatct ttctcttgtg aagtaagcgg atcagcacgt gctatcgagt    5880
gtttggatgg ctctgttttt tctcaggccc cggtagaatt cgatactgga tatccttcta    5940
attctgggat agaactgatg caggcgcaga atgtgaaagg tgtaagctct atttctgcta    6000
tccgtttctt tggtattcag ttggtttatg caggtggctg ggcagttcaa aacgattttg    6060
accctatgac ctttactgta aagatttgtg ctaacgagaa tggtttaccc ggtgcagaaa    6120
tctactcaca ggaagtcgct ttgaatcata acgatacagg tgaaactttt ggtaataatc    6180
ctatcagtat tttctattgg gactttgagc ctgctactcc tattaacaac ttgccggccg    6240
atttctggct tgtaatctct aattcagatt ccgaagcatg gttcctttgg attgatcaga    6300
aagatggtgt aggaccgatt gctacatttg aacgcagca aggtgagcct gagggtactc    6360
ccagccactg gttcctgaga gagggagctc caggcttagg tgtttgcatt aagggaacac    6420
cttcaggtgt tgatatgatc gaggctaata agccatattc gctttcagta agtggcaata    6480
caatttctgt agacgcagga gaggtaacca tttatgatat gaacgctcgt cgagtagcat    6540
atgctgaaaa gggaatttct tatactgctc aagccggaac atatgttctc cgtattgtag    6600
tagatggcat gacatatgtt gaaaaagcgg tggttaccaa gtaaggacac gttttgttta    6660
gatatatagt ctaatttaat gttgaggagg tatgtcttta tggcatacct cttctttttt    6720
attttttact ttgccacagc cacaagcgta ttgcccgtca tgcatatctc aaattgttcc    6780
```

```
tctccactat ctttaattgc gacataagtc ggcagatgtc ttatctttgt acactaaata    6840
tcagtaggta tgtgtaagaa acatttcatc cgatacttct tttggactat cattgtcttt    6900
tttgtgggtg cggctattca ctcttgtaaa gagtctaaga tagatcttga agaagttagc    6960
atagtcgatc tgcaaatcca ccgtttctac ctttccagta agaagaatcc ggatttggaa    7020
aaagtatttt tctctatcga tcatgcaaaa gggacaatta ttaataagaa atatatgccc    7080
tatggcacag ttttggattc tgtaatgatg aaactcgtta ctgatttctc tgcgaaaaaa    7140
ctgcgagtgg ccatcaatga tggagaatat aaggattggc ataataagga ttcattgtgg    7200
ttgcgcgatt gtcataccttt acattta                                        7227
```

<210> SEQ ID NO 5
<211> LENGTH: 1518
<212> TYPE: DNA
<213> ORGANISM: Porphyromonas gingivalis
<220> FEATURE:
<223> OTHER INFORMATION: The following sequence is named QMLragB, which
is a fragment of QML (reverse complemetary sequence from 595 to
2112)

<400> SEQUENCE: 5

```
atgaaaaaga tattatattg ggctgcggca gctctttttg ctgtgagtct cgtttcctgc      60
gatctgaata gagatccgga agataaggcc aagaaagagc ccttcaaaac aatagctcag     120
gctcgtcaga gcagagatgg cttgtattct ctgcttcgtg aatcggagca attagctttc     180
catgtttatg acgaggttca gtcggatatg tacactacta ccaagaacga tggcaaccag     240
tactatccat tcgtagcttg gcagttagga agcatggaaa ctcatggtcg tgctgatgag     300
gatcaagtat atggtattgc cggttattac ttcgagtata gccgtctgat tcagcaggca     360
aactcctata tcgaagatat ggaaaaagct cttgccaata atactgatat gagcattttc     420
atttcctccg aagaagtgga acgtgctaag agatatctcg cagaggtacg tgttgtacaa     480
gctttggcga attggcgttt gatggatcgt tttgcatata aatatgatgc cgcatccaat     540
caaagtcctc aaaaccttgg cattgttttg atcaaggaat tcaatcccgc ttatatcggc     600
ccccgtgcta ctcagaagga gtgttatgat cacatcctct cggctttgga ggctgctatt     660
acggtattgc ctgagaagaa ccctgacggc atcacatatg ccggacgtga ctacgctcat     720
gctttgcgag cacgtgtaca cctttctatg ggtaactatg ccgatgcact tgcagatgct     780
aagcagattg tggagaagta tcctttgatc aacgctaaca atgcagagga ttttgctaaa     840
atctatcgtt cagatgctaa caatcccgag atcgtattcc gtgcttttgc atctcctacg     900
accggtgctg ttggtgcaac ctctcttaat ggcgcatctg tggtgaataa gaagattaaa     960
tatgcgccgt ttatcgttcc cttgcagtgg gtagtcgatt tgtacgaaga tgcagattat    1020
cgcaagtcag tctatattga taagacagtt agtaacggca gtgaaaaggg atatttggtg    1080
aacaaattcc ttgaagatcc tgcctacaga gaaacagccg atatccccat tctgaaaata    1140
ggggtacgta tgttcagtat tgcagaagct tatctgatgg tagctgagtg tgctcacatg    1200
acaggagacg atgctacggc gattgcatac ctcaaaaagc tcagtgctgc tcgtggtggc    1260
aatattgaca ccggtgatgt aatgaaagct attcaagaag aacgtactcg tgagcttatc    1320
ggtgagggcg ctcgtttgcg cgatatgatt cgttggaatc ttccgaatat cgacaaaaca    1380
gaaatccaac ctgctcttac tggttatgct cgtgagatcg tattggagca acctgttccg    1440
gccggtcact atgcatttac atgggagttc cctaaccgag atcgtcaggt taatcctcat    1500
ttgatcaaga actggtaa                                                  1518
```

-continued

<210> SEQ ID NO 6
<211> LENGTH: 1506
<212> TYPE: DNA
<213> ORGANISM: Porphyromonas gingivalis
<220> FEATURE:
<223> OTHER INFORMATION: The following sequence is named ThairagB, which
      is a fragment of the Thai rag (from 5231 to 6736)

<400> SEQUENCE: 6

| | | | | | |
|---|---|---|---|---|---|
| atgaaaatga | aaaaaataat | taattatgct | gtggccggat | tgctactcgt | ttcaagcttt | 60 |
| gccgcttgtg | acttggatcg | cactcctcac | aattctgatg | tccaaaagcc | ttatgaagat | 120 |
| atggccacca | cagttcagta | tagagatgga | ttgtattctg | ttcttcgtgg | tgcagagaat | 180 |
| gccggacggt | atactttgtc | agaatatatg | tccgatatgt | attgtgtaat | gcaaggagat | 240 |
| ggtggccatg | ctacgcctta | tgttacatgg | acgattcctc | gcattgagat | tgctgaccac | 300 |
| gcatcgaatt | attactttgg | ttttaatcgg | ttaattcagc | aagccaatgc | ttttgtcgga | 360 |
| aatgttaagc | tggcaatcgc | aaatgggggtt | tataagacag | aagttgataa | aaccaatgct | 420 |
| caaatttatt | tggctgaggc | caagactttg | caggctttag | ctttgttccg | tcttatggag | 480 |
| cgctttgcct | atccctatga | tccaaacgaa | accacttctc | cgaaaaactt | gggggtggtt | 540 |
| ttgataaagg | aatatgatcc | ttgggctgtg | ggtgcacgag | ctacgcagac | ggaaacgtat | 600 |
| agctatatta | tgagccttct | tgatgaggcc | atctctgttt | tgcctgaaac | gaatgcgaac | 660 |
| aatatgtatg | tgagtcggga | ttatgcttta | ggcttgcgtg | ctcgcgtaca | catggcgatg | 720 |
| gataactatg | ctgaagccgc | caatgatatc | agagctttt | ataaaagta | caatctgatt | 780 |
| tctgctgcta | attccgatga | atttgaggag | gcttatagaa | agatgagctc | caatcctgag | 840 |
| cttatttccc | gcggatatgc | ttccgttact | aacggatacc | ttgtgtatca | ggatttgatg | 900 |
| ggagcaacag | cttctggaac | taatgtgaag | tacaaccctc | gtgttacccc | tctgcaatgg | 960 |
| gtttgcgacc | tttatgatgc | ggctgattat | cgtaagaaag | tgtacattgt | agacaaggtg | 1020 |
| aacggtgacg | gtggcaaagg | ttatgtcgta | aataagttcc | ttggagaccc | tgaacttcgt | 1080 |
| gaagaccccta | agaaggaaaa | tttcaaaacc | ggttgtcgtt | tcttctctct | cgcagaagcc | 1140 |
| tatcttatct | tggcagaagc | agatattatg | actggtaata | cagccgaggc | tatggaagtt | 1200 |
| ctgaaagagc | tgagtaagtc | tcgtggagca | gaggtttccg | gtgcagatta | tatgcaaatc | 1260 |
| ctcaaggatg | agcgtacacg | agaaatgatc | ggtgaaggtt | ctcgtctcaa | tgacatgatt | 1320 |
| cgctggaata | tggatttggt | ggtatctccc | gttcaggctg | ttcttcataa | aatagctgtc | 1380 |
| ccgactatcc | ttcagactga | tgacccgaca | cgtgttcctg | ccggcttcta | tgctttcacg | 1440 |
| tgggaaattc | ccaatcgtga | tcttgtagtt | attcccgagc | tggttcgcaa | ctggccaaaa | 1500 |
| cagtaa | | | | | 1506 |

<210> SEQ ID NO 7
<211> LENGTH: 1506
<212> TYPE: DNA
<213> ORGANISM: Porphyromonas gingivalis
<220> FEATURE:
<223> OTHER INFORMATION: The following sequence is named W50ragB, which
      is a fragment of the W50 rag (from 5417 to 6922)

<400> SEQUENCE: 7

| | | | | | |
|---|---|---|---|---|---|
| atgaaaaaaa | taatttattg | ggttgcgaca | gttttcttag | cagcgagcgt | atcctcttgc | 60 |
| gagcttgacc | gcgaccccga | aggaaaagat | ttccaacagc | catatacttc | tttcgtgcag | 120 |
| acgaaacaaa | acagagatgg | tctttacgca | cttttgcgta | atactgaaaa | tccacgaatg | 180 |

-continued

```
cattttatc aggaacttca atccgatatg tattgcacta ccattactga tggtaactcc      240
ttagctccgt tcgtgaattg ggatttaggc atacttaacg accatggacg tgctgatgag      300
gacgaagtct ccggtatagc tggctactat ttcgtataca atcgactaaa tcagcaagcg      360
aatgcttttg ttaacaatac ggaagctgcg ttgcagaatc aagtgtataa aaattccacc      420
gagatcgcca atgctaagag cttttggcg gaaggaaaag ttttacaagc attggctatt       480
tggcgactga tggatcgttt tagcttccat gaaagcgtga cagaagttaa ttccggtgcg      540
aaagatcttg gcgttattct gttgaaagaa tataatcctg ttatatcgg tccccgtgca       600 acgaaggcac aatgttatga ttacattttg tcacgtttgt ctgaggctat tgaagttttg      660
cccgaaaaca gggaaagcgt tctttatgtg agccgtgatt acgcctatgc cctccgagca     720
agaatttacc tcgcgttggg tgaatatgga aaagctgcag cagatgctaa gatggttgtt     780
gataagtatc ctttgattgg tgcagcagat gcttctgagt ttgagaatat ttatcgatca     840
gatgctaata atcccgaaat tattttcgt ggttttgctt ctgcgactct tggctcgttt      900
actgctacga cactaaatgg tgctgcgcca gcaggtaagg atataaaata taatccgagc     960
gcagtccctt tccaatgggt agtggatctt tatgaaaacg aagatttccg caaatccgta     1020
tatatcgcga agttgtgaa aaaggataag gggtatttag taaataaatt ccttgaggac      1080
aaggcttatc gtgatgttca ggataagcca aaccttaaag tcggagctcg ttattttagc    1140
gttgctgagg tctacttaat tttggtagag tctgctcttc agactggaga taccccaaca    1200
gccgaaaaat atctcaaggc tttgagtaaa gctcgtggag cagaagtttc agtcgttaat    1260
atggaagcac tgcaagcaga gcgtacgcgt gagcttatag gtgagggtag tcgtttgcgt    1320
gatatggtcc gctggagtat ccctaataat catgatgctt ttgagactca gcctggttta    1380
gaaggttttg caaatactac tcctttgaaa gctcaagctc ctgtaggctt ttatgcatat    1440
acttgggagt tcccacagcg agatcgacaa actaatccgc agttaataaa gaactggccg    1500
atataa                                                                 1506
```

<210> SEQ ID NO 8
<211> LENGTH: 1518
<212> TYPE: DNA
<213> ORGANISM: Porphyromonas gingivalis
<220> FEATURE:
<223> OTHER INFORMATION: The following sequence is named 381ragB, which
      is a fragment of 381 (from 4077 to 5594)

<400> SEQUENCE: 8

```
atcattatga agaaaatatt ttatgcagtg ctgtctgctt tcctgctgtt ggggcttttt       60
tcatgcgatc tgcagcgtga tccggatgga agtgatgaac agaaagatca tttcgcttct     120
tttgtggaga caaacattt tagagatggt ttgtatgcta cgttgcgaag tacagaaaac     180
cctactcgtt tcgtatggca ggatcttcaa tcagacatgt atgcagtaac aacgaatgat     240
ggtaatacaa gctctcgttt tatcacatgg agtttgggtg cactggagtc atccggtgag    300
attgcttcat attatctcgc ttattatagc ttgttgcagc gcgccaatta ttttgtgacc     360
agaatagaac gttctatgga gttgaatctt tatctggaga agaactcaa agatgtaaag     420 atctttcaag cagaaggtaa gactcttcag gcattggccc tctctcgttt gatggagcgt    480
tttgcttata agtatgatcc tgcggccact actcatccgt atgatttggg tattgtactt     540
gttaaggatt acaatcctat gattgctgca cctcgtaata cgcagaaaga gtgctacgat     600
tatatccttg aatgcttaaa tcaggcgatt gatgttttgc cgaacaagag caatgaaggt     660
aatatcagag tttccaagca ttatgctcat gcttttgcgtg cacgtgtaaa ttttgcaatg     720
```

```
ggtaattatg atgcggcaaa agaagatgct aaagttctgg tcgacaatta tcctcttatt    780
gatgtgacga cagcaaagaa atttgctgag gtttaccgcg atgatgctaa caaccccgaa    840
atcgtattcc gtgcttttgc ttcaggaact atcggtactg ttgcagaaac gaccctaagc    900
ggattcttgt ggcattcagg tgctcagctt gtggtttcaa gtcctatttc agctcctttc    960
caatggggtg ttgacctata tgatgatacc gattatcgta agtcttgcta tatcacgaaa   1020
gatttctacg ttattggtgg tggtgttgat aagggttatg tagttggaaa atatctgggt   1080
aaccccgctt atcagtctaa tcctaacgta cccgacttta aggtgaccag ccgcttcttc   1140
tcagttgcag aggcttattt gatcatggca gagtctatgg ccaagtccgg tgatgcagcc   1200
ggtgcaaagg atctgttgaa gacgctttgt gagaaacgtg gtggccagtt ggaagatggc   1260
gatatcatgg atttggtaat ggcagaacgt acccgtgagc tgatcggaga aggctctcgt   1320
ctgaacgata tgattcgttg gaatttgcct aataaccacg atgatatgga aaatcagccg   1380
gtattcctgc agatcggtct tgcaaaagct gataagctga agcagcccgt acctgccggt   1440
cactatgcgt ttacttggga gttccctgtt agggatcgtc aggtgaatcc gcagattatc   1500
aaaaactggc cgaactaa                                                 1518
```

<210> SEQ ID NO 9
<211> LENGTH: 505
<212> TYPE: PRT
<213> ORGANISM: Artificial Sequence
<220> FEATURE:
<223> OTHER INFORMATION: The following sequence is named QMLRagB, which is converted from QMLragB

<400> SEQUENCE: 9

Met Lys Lys Ile Leu Tyr Trp Ala Ala Ala Leu Phe Ala Val Ser
1               5                   10                  15

Leu Val Ser Cys Asp Leu Asn Arg Asp Pro Glu Asp Lys Ala Lys Lys
            20                  25                  30

Glu Pro Phe Lys Thr Ile Ala Gln Ala Arg Gln Ser Arg Asp Gly Leu
        35                  40                  45

Tyr Ser Leu Leu Arg Glu Ser Glu Gln Leu Ala Phe His Val Tyr Asp
    50                  55                  60

Glu Val Gln Ser Asp Met Tyr Thr Thr Thr Lys Asn Asp Gly Asn Gln
65                  70                  75                  80

Tyr Tyr Pro Phe Val Ala Trp Gln Leu Gly Ser Met Glu Thr His Gly
                85                  90                  95

Arg Ala Asp Glu Asp Gln Val Tyr Gly Ile Ala Gly Tyr Tyr Phe Glu
            100                 105                 110

Tyr Ser Arg Leu Ile Gln Gln Ala Asn Ser Tyr Ile Glu Asp Met Glu
        115                 120                 125

Lys Ala Leu Ala Asn Asn Thr Asp Met Ser Ile Phe Ile Ser Ser Glu
    130                 135                 140

Glu Val Glu Arg Ala Lys Arg Tyr Leu Ala Glu Val Arg Val Val Gln
145                 150                 155                 160

Ala Leu Ala Asn Trp Arg Leu Met Asp Arg Phe Ala Tyr Lys Tyr Asp
                165                 170                 175

Ala Ala Ser Asn Gln Ser Pro Gln Asn Leu Gly Ile Val Leu Ile Lys
            180                 185                 190

Glu Phe Asn Pro Ala Tyr Ile Gly Pro Arg Ala Thr Gln Lys Glu Cys
        195                 200                 205

Tyr Asp His Ile Leu Ser Ala Leu Glu Ala Ala Ile Thr Val Leu Pro

```
              210                 215                 220
Glu Lys Asn Pro Asp Gly Ile Thr Tyr Ala Gly Arg Asp Tyr Ala His
225                 230                 235                 240

Ala Leu Arg Ala Arg Val His Leu Ser Met Gly Asn Tyr Ala Asp Ala
                245                 250                 255

Leu Ala Asp Ala Lys Gln Ile Val Glu Lys Tyr Pro Leu Ile Asn Ala
            260                 265                 270

Asn Asn Ala Glu Asp Phe Ala Lys Ile Tyr Arg Ser Asp Ala Asn Asn
        275                 280                 285

Pro Glu Ile Val Phe Arg Ala Phe Ala Ser Pro Thr Thr Gly Ala Val
    290                 295                 300

Gly Ala Thr Ser Leu Asn Gly Ala Ser Val Val Asn Lys Lys Ile Lys
305                 310                 315                 320

Tyr Ala Pro Phe Ile Val Pro Leu Gln Trp Val Val Asp Leu Tyr Glu
                325                 330                 335

Asp Ala Asp Tyr Arg Lys Ser Val Tyr Ile Asp Lys Thr Val Ser Asn
            340                 345                 350

Gly Ser Glu Lys Gly Tyr Leu Val Asn Lys Phe Leu Glu Asp Pro Ala
        355                 360                 365

Tyr Arg Glu Thr Ala Asp Ile Pro Ile Leu Lys Ile Gly Val Arg Met
    370                 375                 380

Phe Ser Ile Ala Glu Ala Tyr Leu Met Val Ala Glu Cys Ala His Met
385                 390                 395                 400

Thr Gly Asp Asp Ala Thr Ala Ile Ala Tyr Leu Lys Lys Leu Ser Ala
                405                 410                 415

Ala Arg Gly Gly Asn Ile Asp Thr Gly Asp Val Met Lys Ala Ile Gln
            420                 425                 430

Glu Glu Arg Thr Arg Glu Leu Ile Gly Glu Gly Ala Arg Leu Arg Asp
        435                 440                 445

Met Ile Arg Trp Asn Leu Pro Asn Ile Asp Lys Thr Glu Ile Gln Pro
    450                 455                 460

Ala Leu Thr Gly Tyr Ala Arg Glu Ile Val Leu Glu Gln Pro Val Pro
465                 470                 475                 480

Ala Gly His Tyr Ala Phe Thr Trp Glu Phe Pro Asn Arg Asp Arg Gln
                485                 490                 495

Val Asn Pro His Leu Ile Lys Asn Trp
            500                 505

<210> SEQ ID NO 10
<211> LENGTH: 501
<212> TYPE: PRT
<213> ORGANISM: Artificial Sequence
<220> FEATURE:
<223> OTHER INFORMATION: The following sequence is named ThaiRagB, which
      is converted from ThairagB

<400> SEQUENCE: 10

Met Lys Met Lys Lys Ile Ile Asn Tyr Ala Val Ala Gly Leu Leu Leu
1               5                   10                  15

Val Ser Ser Phe Ala Ala Cys Asp Leu Asp Arg Thr Pro His Asn Ser
            20                  25                  30

Asp Val Gln Lys Pro Tyr Glu Asp Met Ala Thr Thr Val Gln Tyr Arg
        35                  40                  45

Asp Gly Leu Tyr Ser Val Leu Arg Gly Ala Glu Asn Ala Gly Arg Tyr
    50                  55                  60

Thr Leu Ser Glu Tyr Met Ser Asp Met Tyr Cys Val Met Gln Gly Asp
```

```
                65                  70                  75                  80
Gly Gly His Ala Thr Pro Tyr Val Thr Trp Thr Ile Pro Arg Ile Glu
                    85                  90                  95
Ile Ala Asp His Ala Ser Asn Tyr Tyr Phe Gly Phe Asn Arg Leu Ile
                    100                 105                 110
Gln Gln Ala Asn Ala Phe Val Gly Asn Val Lys Leu Ala Ile Ala Asn
                    115                 120                 125
Gly Val Tyr Lys Thr Glu Val Asp Lys Thr Asn Ala Gln Ile Tyr Leu
                    130                 135                 140
Ala Glu Ala Lys Thr Leu Gln Ala Leu Ala Leu Phe Arg Leu Met Glu
145                 150                 155                 160
Arg Phe Ala Tyr Pro Tyr Asp Pro Asn Glu Thr Thr Ser Pro Lys Asn
                    165                 170                 175
Leu Gly Val Val Leu Ile Lys Glu Tyr Asp Pro Trp Ala Val Gly Ala
                    180                 185                 190
Arg Ala Thr Gln Thr Glu Thr Tyr Ser Tyr Ile Met Ser Leu Leu Asp
                    195                 200                 205
Glu Ala Ile Ser Val Leu Pro Glu Thr Asn Ala Asn Asn Met Tyr Val
210                 215                 220
Ser Arg Asp Tyr Ala Leu Gly Leu Arg Ala Arg Val His Met Ala Met
225                 230                 235                 240
Asp Asn Tyr Ala Glu Ala Ala Asn Asp Ile Arg Ala Phe Tyr Lys Lys
                    245                 250                 255
Tyr Asn Leu Ile Ser Ala Ala Asn Ser Asp Glu Phe Glu Glu Ala Tyr
                    260                 265                 270
Arg Lys Met Ser Ser Asn Pro Glu Leu Ile Phe Arg Gly Tyr Ala Ser
                    275                 280                 285
Val Thr Asn Gly Tyr Leu Val Tyr Gln Asp Leu Met Gly Ala Thr Ala
                    290                 295                 300
Ser Gly Thr Asn Val Lys Tyr Asn Pro Arg Val Thr Pro Leu Gln Trp
305                 310                 315                 320
Val Cys Asp Leu Tyr Asp Ala Ala Asp Tyr Arg Lys Lys Val Tyr Ile
                    325                 330                 335
Val Asp Lys Val Asn Gly Asp Gly Lys Gly Tyr Val Val Asn Lys
                    340                 345                 350
Phe Leu Gly Asp Pro Glu Leu Arg Glu Asp Pro Lys Lys Glu Asn Phe
                    355                 360                 365
Lys Thr Gly Cys Arg Phe Phe Ser Leu Ala Glu Ala Tyr Leu Ile Leu
                    370                 375                 380
Ala Glu Ala Asp Ile Met Thr Gly Asn Thr Ala Glu Ala Met Glu Val
385                 390                 395                 400
Leu Lys Glu Leu Ser Lys Ser Arg Gly Ala Glu Val Ser Gly Ala Asp
                    405                 410                 415
Tyr Met Gln Ile Leu Lys Asp Glu Arg Thr Arg Glu Met Ile Gly Glu
                    420                 425                 430
Gly Ser Arg Leu Asn Asp Met Ile Arg Trp Asn Met Asp Leu Val Val
                    435                 440                 445
Ser Pro Val Gln Ala Val Leu His Lys Ile Ala Val Pro Thr Ile Leu
450                 455                 460
Gln Thr Asp Asp Pro Thr Arg Val Pro Ala Gly Phe Tyr Ala Phe Thr
465                 470                 475                 480
Trp Glu Ile Pro Asn Arg Asp Leu Val Val Ile Pro Glu Leu Val Arg
                    485                 490                 495
```

```
Asn Trp Pro Lys Gln
            500

<210> SEQ ID NO 11
<211> LENGTH: 501
<212> TYPE: PRT
<213> ORGANISM: Artificial Sequence
<220> FEATURE:
<223> OTHER INFORMATION: The following sequence is named W50RagB, which
      is converted from W50ragB

<400> SEQUENCE: 11

Met Lys Lys Ile Ile Tyr Trp Val Ala Thr Val Phe Leu Ala Ala Ser
1               5                   10                  15

Val Ser Ser Cys Glu Leu Asp Arg Asp Pro Glu Gly Lys Asp Phe Gln
            20                  25                  30

Gln Pro Tyr Thr Ser Phe Val Gln Thr Lys Gln Asn Arg Asp Gly Leu
        35                  40                  45

Tyr Ala Leu Leu Arg Asn Thr Glu Asn Pro Arg Met His Phe Tyr Gln
    50                  55                  60

Glu Leu Gln Ser Asp Met Tyr Cys Thr Thr Ile Thr Asp Gly Asn Ser
65                  70                  75                  80

Leu Ala Pro Phe Val Asn Trp Asp Leu Gly Ile Leu Asn Asp His Gly
                85                  90                  95

Arg Ala Asp Glu Asp Glu Val Ser Gly Ile Ala Gly Tyr Tyr Phe Val
            100                 105                 110

Tyr Asn Arg Leu Asn Gln Gln Ala Asn Ala Phe Val Asn Asn Thr Glu
        115                 120                 125

Ala Ala Leu Gln Asn Gln Val Tyr Lys Asn Ser Thr Glu Ile Ala Asn
    130                 135                 140

Ala Lys Ser Phe Leu Ala Glu Gly Lys Val Leu Gln Ala Leu Ala Ile
145                 150                 155                 160

Trp Arg Leu Met Asp Arg Phe Ser Phe His Glu Ser Val Thr Glu Val
                165                 170                 175

Asn Ser Gly Ala Lys Asp Leu Gly Val Ile Leu Leu Lys Glu Tyr Asn
            180                 185                 190

Pro Gly Tyr Ile Gly Pro Arg Ala Thr Lys Ala Gln Cys Tyr Asp Tyr
        195                 200                 205

Ile Leu Ser Arg Leu Ser Glu Ala Ile Glu Val Leu Pro Glu Asn Arg
    210                 215                 220

Glu Ser Val Leu Tyr Val Ser Arg Asp Tyr Ala Tyr Ala Leu Arg Ala
225                 230                 235                 240

Arg Ile Tyr Leu Ala Leu Gly Glu Tyr Gly Lys Ala Ala Ala Asp Ala
                245                 250                 255

Lys Met Val Val Asp Lys Tyr Pro Leu Ile Gly Ala Ala Asp Ala Ser
            260                 265                 270

Glu Phe Glu Asn Ile Tyr Arg Ser Asp Ala Asn Asn Pro Glu Ile Ile
        275                 280                 285

Phe Arg Gly Phe Ala Ser Ala Thr Leu Gly Ser Phe Thr Ala Thr Thr
    290                 295                 300

Leu Asn Gly Ala Ala Pro Ala Gly Lys Asp Ile Lys Tyr Asn Pro Ser
305                 310                 315                 320

Ala Val Pro Phe Gln Trp Val Asp Leu Tyr Glu Asn Glu Asp Phe
                325                 330                 335

Arg Lys Ser Val Tyr Ile Ala Lys Val Val Lys Asp Lys Gly Tyr
            340                 345                 350
```

```
Leu Val Asn Lys Phe Leu Glu Asp Lys Ala Tyr Arg Asp Val Gln Asp
            355                 360                 365

Lys Pro Asn Leu Lys Val Gly Ala Arg Tyr Phe Ser Val Ala Glu Val
        370                 375                 380

Tyr Leu Ile Leu Val Glu Ser Ala Leu Gln Thr Gly Asp Thr Pro Thr
385                 390                 395                 400

Ala Glu Lys Tyr Leu Lys Ala Leu Ser Lys Ala Arg Gly Ala Glu Val
                405                 410                 415

Ser Val Val Asn Met Glu Ala Leu Gln Ala Glu Arg Thr Arg Glu Leu
                420                 425                 430

Ile Gly Glu Gly Ser Arg Leu Arg Asp Met Val Arg Trp Ser Ile Pro
            435                 440                 445

Asn Asn His Asp Ala Phe Glu Thr Gln Pro Gly Leu Glu Gly Phe Ala
            450                 455                 460

Asn Thr Thr Pro Leu Lys Ala Gln Ala Pro Val Gly Phe Tyr Ala Tyr
465                 470                 475                 480

Thr Trp Glu Phe Pro Gln Arg Asp Arg Gln Thr Asn Pro Gln Leu Ile
                485                 490                 495

Lys Asn Trp Pro Ile
            500

<210> SEQ ID NO 12
<211> LENGTH: 505
<212> TYPE: PRT
<213> ORGANISM: Artificial Sequence
<220> FEATURE:
<223> OTHER INFORMATION: The following sequence is named 381RagB, which
      is converted from 381ragB

<400> SEQUENCE: 12

Ile Ile Met Lys Lys Ile Phe Tyr Ala Val Leu Ser Ala Phe Leu Leu
1               5                   10                  15

Leu Gly Leu Phe Ser Cys Asp Leu Gln Arg Asp Pro Asp Gly Ser Asp
            20                  25                  30

Glu Gln Lys Asp His Phe Ala Ser Phe Val Glu Thr Lys His Phe Arg
        35                  40                  45

Asp Gly Leu Tyr Ala Thr Leu Arg Ser Thr Glu Asn Pro Thr Arg Phe
    50                  55                  60

Val Trp Gln Asp Leu Gln Ser Asp Met Tyr Ala Val Thr Thr Asn Asp
65                  70                  75                  80

Gly Asn Thr Ser Ser Arg Phe Ile Thr Trp Ser Leu Gly Ala Leu Glu
                85                  90                  95

Ser Ser Gly Glu Ile Ala Ser Tyr Tyr Leu Ala Tyr Tyr Ser Leu Leu
            100                 105                 110

Gln Arg Ala Asn Tyr Phe Val Thr Arg Ile Glu Arg Ser Met Glu Leu
        115                 120                 125

Asn Leu Tyr Leu Glu Lys Glu Leu Lys Asp Val Lys Ile Phe Gln Ala
    130                 135                 140

Glu Gly Lys Thr Leu Gln Ala Leu Ala Leu Ser Arg Leu Met Glu Arg
145                 150                 155                 160

Phe Ala Tyr Lys Tyr Asp Pro Ala Ala Thr Thr His Pro Tyr Asp Leu
                165                 170                 175

Gly Ile Val Leu Val Lys Asp Tyr Asn Pro Met Ile Ala Ala Pro Arg
            180                 185                 190

Asn Thr Gln Lys Glu Cys Tyr Asp Tyr Ile Leu Glu Cys Leu Asn Gln
        195                 200                 205
```

-continued

```
Ala Ile Asp Val Leu Pro Asn Lys Ser Asn Glu Gly Asn Ile Arg Val
    210                 215                 220

Ser Lys His Tyr Ala His Ala Leu Arg Ala Arg Val Asn Phe Ala Met
225                 230                 235                 240

Gly Asn Tyr Asp Ala Ala Lys Glu Asp Ala Lys Val Leu Val Asp Asn
                245                 250                 255

Tyr Pro Leu Ile Asp Val Thr Thr Ala Lys Lys Phe Ala Glu Val Tyr
            260                 265                 270

Arg Asp Asp Ala Asn Asn Pro Glu Ile Val Phe Arg Ala Phe Ala Ser
        275                 280                 285

Gly Thr Ile Gly Thr Val Ala Glu Thr Thr Leu Ser Gly Phe Leu Trp
    290                 295                 300

His Ser Gly Ala Gln Leu Val Val Ser Ser Pro Ile Ser Ala Pro Phe
305                 310                 315                 320

Gln Trp Val Val Asp Leu Tyr Asp Thr Asp Tyr Arg Lys Ser Cys
                325                 330                 335

Tyr Ile Thr Lys Asp Phe Tyr Val Ile Gly Gly Val Asp Lys Gly
            340                 345                 350

Tyr Val Val Gly Lys Tyr Leu Gly Asn Pro Ala Tyr Gln Ser Asn Pro
        355                 360                 365

Asn Val Pro Asp Phe Lys Val Thr Ser Arg Phe Phe Ser Val Ala Glu
    370                 375                 380

Ala Tyr Leu Ile Met Ala Glu Ser Met Ala Lys Ser Gly Asp Ala Ala
385                 390                 395                 400

Gly Ala Lys Asp Leu Leu Lys Thr Leu Cys Glu Lys Arg Gly Gly Gln
                405                 410                 415

Leu Glu Asp Gly Asp Ile Met Asp Leu Val Met Ala Gly Arg Thr Arg
            420                 425                 430

Glu Leu Ile Gly Glu Gly Ser Arg Leu Asn Asp Met Ile Arg Trp Asn
        435                 440                 445

Leu Pro Asn Asn His Asp Asp Met Glu Asn Gln Pro Val Phe Leu Gln
    450                 455                 460

Ile Gly Leu Ala Lys Ala Asp Lys Leu Lys Gln Pro Val Pro Ala Gly
465                 470                 475                 480

His Tyr Ala Phe Thr Trp Glu Phe Pro Val Arg Asp Arg Gln Val Asn
                485                 490                 495

Pro Gln Ile Ile Lys Asn Trp Pro Asn
            500                 505
```

<210> SEQ ID NO 13
<211> LENGTH: 20
<212> TYPE: DNA
<213> ORGANISM: Porphyromonas gingivalis
<220> FEATURE:
<223> OTHER INFORMATION: The following sequence is a forward primer of
      the 16s rRNA of P. gingivalis

<400> SEQUENCE: 13
aggcagcttg ccatactgcg                                                 20

<210> SEQ ID NO 14
<211> LENGTH: 21
<212> TYPE: DNA
<213> ORGANISM: Porphyromonas gingivalis
<220> FEATURE:
<223> OTHER INFORMATION: The following sequence is a reverse primer of
      the 16s rRNA of P. gingivalis

<400> SEQUENCE: 14

```
actgttagca actaccgatg t                                              21
```

<210> SEQ ID NO 15
<211> LENGTH: 21
<212> TYPE: DNA
<213> ORGANISM: Porphyromonas gingivalis
<220> FEATURE:
<223> OTHER INFORMATION: The following sequence is a forward primer of
      the rag locus of P. gingivalis

<400> SEQUENCE: 15

```
caaagtcctg ccacgagtag c                                              21
```

<210> SEQ ID NO 16
<211> LENGTH: 21
<212> TYPE: DNA
<213> ORGANISM: Porphyromonas gingivalis
<220> FEATURE:
<223> OTHER INFORMATION: The following sequence is a reverse primer of
      the rag locus of P. gingivalis

<400> SEQUENCE: 16

```
cgttttctcg ccactttcgt c                                              21
```

<210> SEQ ID NO 17
<211> LENGTH: 22
<212> TYPE: DNA
<213> ORGANISM: Porphyromonas gingivalis
<220> FEATURE:
<223> OTHER INFORMATION: The following sequence is a forward primer of
      rag1 (W50) of P. gingivalis

<400> SEQUENCE: 17

```
cgcgaccccg aaggaaaaga tt                                             22
```

<210> SEQ ID NO 18
<211> LENGTH: 22
<212> TYPE: DNA
<213> ORGANISM: Porphyromonas gingivalis
<220> FEATURE:
<223> OTHER INFORMATION: The following sequence is a reverse primer of
      rag1 (W50) of P. gingivalis

<400> SEQUENCE: 18

```
cacggctcac ataaagaacg ct                                             22
```

<210> SEQ ID NO 19
<211> LENGTH: 21
<212> TYPE: DNA
<213> ORGANISM: Porphyromonas gingivalis
<220> FEATURE:
<223> OTHER INFORMATION: The following sequence is a forward primer of
      rag2 (Thai) of P. gingivalis

<400> SEQUENCE: 19

```
gctttgccgc ttgtgacttg g                                              21
```

<210> SEQ ID NO 20
<211> LENGTH: 21
<212> TYPE: DNA
<213> ORGANISM: Porphyromonas gingivalis
<220> FEATURE:
<223> OTHER INFORMATION: The following sequence is a reverse primer of
      rag2 (Thai) of P. gingivalis

<400> SEQUENCE: 20

```
ccaccgtcac cgttcacctt g                                              21
```

<210> SEQ ID NO 21
<211> LENGTH: 23
<212> TYPE: DNA
<213> ORGANISM: Porphyromonas gingivalis
<220> FEATURE:
<223> OTHER INFORMATION: The following sequence is a forward primer of
      rag3 (QML) of P. gingivalis

<400> SEQUENCE: 21
ccggaagata aggccaagaa aga                                           23

<210> SEQ ID NO 22
<211> LENGTH: 19
<212> TYPE: DNA
<213> ORGANISM: Porphyromonas gingivalis
<220> FEATURE:
<223> OTHER INFORMATION: The following sequence is a reverse primer of
      rag3 (QML) of P. gingivalis

<400> SEQUENCE: 22
acgccaattc gccaaagct                                                19

<210> SEQ ID NO 23
<211> LENGTH: 22
<212> TYPE: DNA
<213> ORGANISM: Porphyromonas gingivalis
<220> FEATURE:
<223> OTHER INFORMATION: The following sequence is a forward primer of
      rag4 (381) of P. gingivalis

<400> SEQUENCE: 23
ccggatggaa gtgatgaaca ga                                            22

<210> SEQ ID NO 24
<211> LENGTH: 21
<212> TYPE: DNA
<213> ORGANISM: Porphyromonas gingivalis
<220> FEATURE:
<223> OTHER INFORMATION: The following sequence is a reverse primer of
      rag4 (381) of P. gingivalis

<400> SEQUENCE: 24
cgcggtaaac ctcagcaaat t                                             21

<210> SEQ ID NO 25
<211> LENGTH: 22
<212> TYPE: DNA
<213> ORGANISM: Porphyromonas gingivalis
<220> FEATURE:
<223> OTHER INFORMATION: The following sequence is a forward primer of
      ragA of P. gingivalis

<400> SEQUENCE: 25
cgctattctt cctttgcttg ct                                            22

<210> SEQ ID NO 26
<211> LENGTH: 21
<212> TYPE: DNA
<213> ORGANISM: Porphyromonas gingivalis
<220> FEATURE:
<223> OTHER INFORMATION: The following sequence is a reverse primer of
      ragA of P. gingivalis

<400> SEQUENCE: 26
ttaccatccg catcgacttg a                                             21

```
<210> SEQ ID NO 27
<211> LENGTH: 31
<212> TYPE: DNA
<213> ORGANISM: Artificial Sequence
<220> FEATURE:
<223> OTHER INFORMATION: The following sequence is a forward primer of
      ragB of P. gingivalis

<400> SEQUENCE: 27
atatatgagc tccgcgaccc cgaaggaaaa g                                    31

<210> SEQ ID NO 28
<211> LENGTH: 32
<212> TYPE: DNA
<213> ORGANISM: Artificial Sequence
<220> FEATURE:
<223> OTHER INFORMATION: The following sequence is a reverse primer of
      ragB of P. gingivalis

<400> SEQUENCE: 28
tatatagtcg acgaaaagat aggggctgcg ac                                   32
```